(12) United States Patent
Heneghan

(10) Patent No.: US 10,159,421 B2
(45) Date of Patent: Dec. 25, 2018

(54) DETECTION OF PERIODIC BREATHING

(71) Applicant: ResMed Sensor Technologies Limited, Dublin (IE)

(72) Inventor: Conor Heneghan, San Diego, CA (US)

(73) Assignee: ResMed Sensor Technologies Limited (AU)

(*) Notice: Subject to any disclaimer, the term of this patent is extended or adjusted under 35 U.S.C. 154(b) by 236 days.

(21) Appl. No.: 15/079,339

(22) Filed: Mar. 24, 2016

(65) Prior Publication Data

US 2016/0287122 A1 Oct. 6, 2016

Related U.S. Application Data

(60) Provisional application No. 62/140,001, filed on Mar. 30, 2015.

(51) Int. Cl.
*A61B 5/0456* (2006.01)
*A61B 5/04* (2006.01)
*A61B 5/00* (2006.01)
*A61B 5/0402* (2006.01)
(Continued)

(52) U.S. Cl.
CPC ........ *A61B 5/04017* (2013.01); *A61B 5/0402* (2013.01); *A61B 5/0452* (2013.01); *A61B 5/113* (2013.01); *A61B 5/4818* (2013.01); *A61B 5/7264* (2013.01); *A61B 5/7278* (2013.01); *A61B 2562/0219* (2013.01)

(58) Field of Classification Search
CPC ....... A61B 5/08; A61B 5/0402; A61B 5/0456; A61B 5/1135; A61B 5/4806; A61B 5/4809; A61B 5/4818; A61B 7/003

USPC .......................................... 600/484, 521, 534
See application file for complete search history.

(56) References Cited

U.S. PATENT DOCUMENTS

| 4,782,832 A | 11/1988 | Trimble et al. |
| 4,944,310 A | 7/1990 | Sullivan |
| 6,532,959 B1 | 3/2003 | Berthon-Jones |

(Continued)

FOREIGN PATENT DOCUMENTS

| WO | 1998/004310 A1 | 2/1998 |
| WO | 1998/034665 A1 | 8/1998 |

(Continued)

*Primary Examiner* — Carl H Layno
*Assistant Examiner* — Jon Eric C Morales
(74) *Attorney, Agent, or Firm* — Botos Churchill IP Law LLP

(57) ABSTRACT

Methods and apparatus perform periodic breathing detection, such as Cheyne-Stokes respiration detection. The detection may be performed by one or more processors, such as by analysis of data from one or more sensors. In some cases, the detection may be based on an electrocardiogram (ECG) signal, such as from ECG electrodes and/or an accelerometer signal, such as from an accelerometer. An occurrence of periodic breathing may be detected based on features derived from the signal(s). For example, detection may be based on deriving a respiration signal from the sensed signal(s) and/or analysis of RR interval times or relative QRS amplitude values, which may be evaluated on a segment-by-segment basis. The detection may provide monitoring and reporting of the occurrence of periodic breathing by a monitoring device and/or provide a basis for controlling changes to a provided respiratory treatment or therapy, such as by a respiratory pressure therapy device.

66 Claims, 36 Drawing Sheets

(51) Int. Cl.
*A61B 5/0452* (2006.01)
*A61B 5/113* (2006.01)

(56) References Cited

U.S. PATENT DOCUMENTS

| | | | |
|---|---|---|---|
| 6,581,594 | B1 | 6/2003 | Drew et al. |
| 8,066,647 | B2 | 11/2011 | Armitstead |
| 2006/0041201 | A1* | 2/2006 | Behbehani ........... A61B 5/0456 600/521 |
| 2009/0044808 | A1 | 2/2009 | Guney et al. |
| 2009/0050156 | A1 | 2/2009 | Ng et al. |
| 2010/0000534 | A1 | 1/2010 | Kooij et al. |
| 2011/0105915 | A1* | 5/2011 | Bauer ................... A61B 5/0456 600/484 |
| 2012/0016218 | A1 | 1/2012 | Lau et al. |

FOREIGN PATENT DOCUMENTS

| | | |
|---|---|---|
| WO | 00078381 A1 | 12/2000 |
| WO | 2004/073778 A1 | 9/2004 |
| WO | 2005/063328 A1 | 7/2005 |
| WO | 2006074513 A1 | 7/2006 |
| WO | 2006130903 A1 | 12/2006 |
| WO | 2009/052560 A1 | 4/2009 |
| WO | 2010135785 A1 | 12/2010 |
| WO | 2013110136 A1 | 8/2013 |

\* cited by examiner

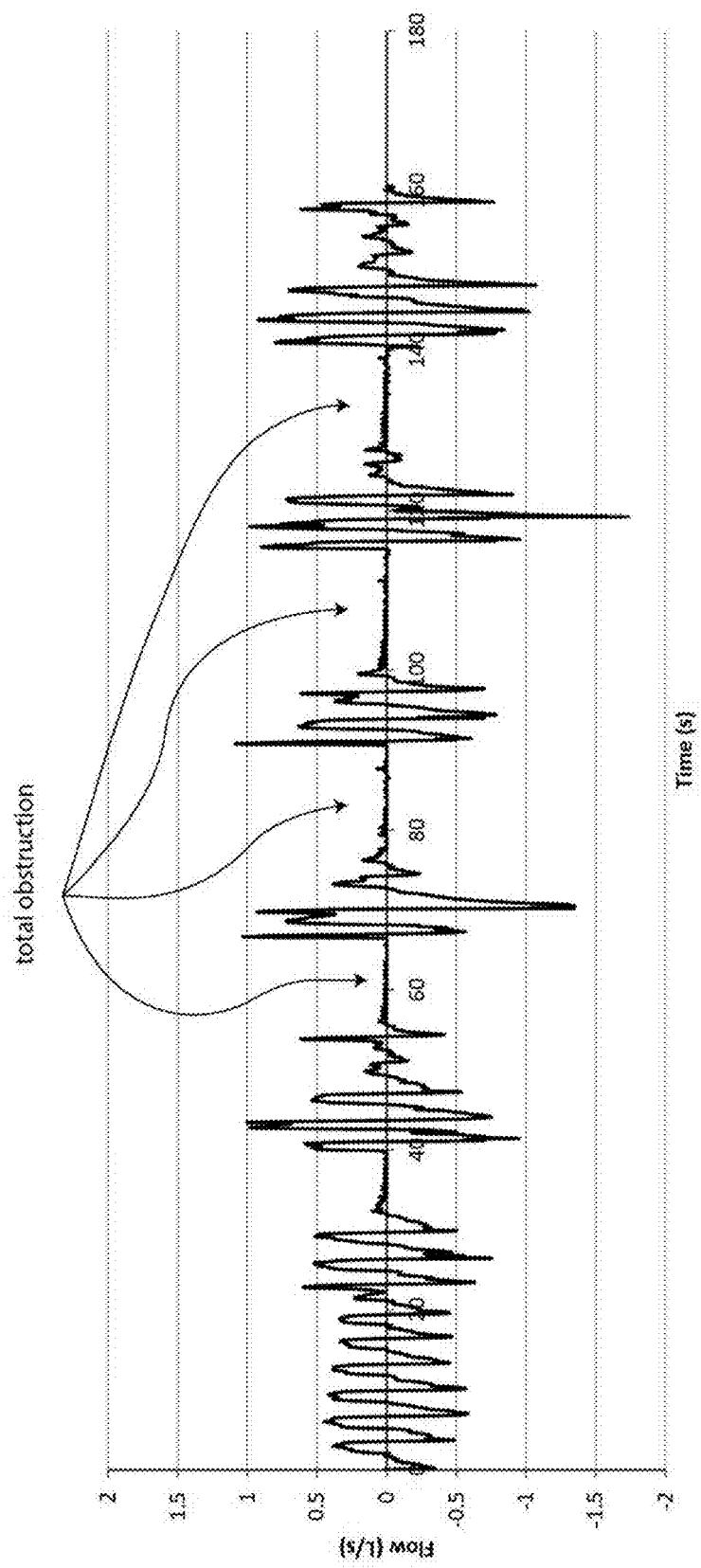

DETECTION OF PERIODIC BREATHING

CROSS-REFERENCE TO RELATED APPLICATIONS

This application claims the benefit of the filing date of U.S. Provisional Patent Application No. 62/140,001 filed Mar. 30, 2015, the disclosure of which is hereby incorporated herein by reference.

BACKGROUND OF THE TECHNOLOGY 1.1 Field of the Technology

The present technology relates to detecting periodic breathing such as Cheyne-Stokes respiration. In particular, the present technology relates to medical devices, apparatus or systems that detect periodic breathing such as by analyzing an electrocardiogram signal.

1.2 Description of the Related Art 1.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

1.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall. Treatment of OSA by nasal CPAP therapy may be voluntary, and hence patients may elect not to comply with therapy if they find devices used to provide such therapy one or more of uncomfortable, difficult to use, expensive or aesthetically unappealing.

Non-invasive ventilation (NIV) provides ventilatory support to a patient through the upper airways to assist the patient in taking a full breath and/or maintain adequate oxygen levels in the body by doing some or all of the work of breathing. The ventilatory support is provided via a patient interface. NIV has been used to treat CSR, OHS, COPD, MD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

1.2.3 Diagnosis and Treatment Systems

These therapies may be provided by a treatment system or device. Systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

1.2.3.1 Patient Interface

A patient interface may be used to interface respiratory equipment to its user, for example by providing a flow of air. The flow of air may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cmH2O. For other forms of therapy, such as the delivery of oxygen, the patient interface may not include a seal sufficient to facilitate delivery to the airways of a supply of gas at a positive pressure of about 10 cmH2O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, mask designed as part of personal protection equipment (e.g. filter masks), SCUBA masks, or for the administration of anaesthetics may be tolerable for their original application, but nevertheless be undesirably uncomfortable to be worn for extended periods of time, e.g. several hours. This discomfort may lead to a reduction in patient compliance with therapy. This is even more so if the mask is to be worn during sleep.

Nasal CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g. difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of nasal CPAP during sleep form a distinct field.

1.2.3.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may unintentionally leak. Furthermore, if the shape of the seal-forming portion does not match that of the patient, it may crease or buckle in use, giving rise to unintentional leaks.

Another type of seal-forming portion may comprise a friction-fit element, e.g. for insertion into a naris, however some patients find these uncomfortable.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063,328 and WO 2006/130,903 (describing amongst other things aspects of ResMed LIBERTY full-face mask); International Patent Application WO 2009/052,560 (describing amongst other things aspects of ResMed SWIFT FX nasal pillows).

1.2.3.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534. However these may be uncomfortable for some.

Another technique is the use of one or more straps and stabilising harnesses. Many such harnesses suffer from being one or more of ill-fitting, bulky, uncomfortable and awkward to use.

1.2.3.1.3 Vent Technologies

Some forms of patient interface systems may include a vent to allow the washout of exhaled carbon dioxide. The vent may allow a flow of gas from an interior space of the patient interface, e.g. the plenum chamber, to an exterior of the patient interface, e.g. to ambient. The vent may comprise an orifice and gas may flow through the orifice in use of the mask. Many such vents are noisy. Others may block in use and provide insufficient washout. Some vents may be disruptive of the sleep of a bed-partner 1100 of the patient 1000, e.g. through noise or focused airflow.

ResMed Limited has developed a number of improved mask vent technologies. See WO 1998/034,665; WO 2000/078,381; U.S. Pat. No. 6,581,594; US patent application; US 2009/0050156; US Patent Application 2009/0044808.

Table of noise of prior masks (ISO 17510-2:2007, 10 cmH$_2$O pressure at 1$m$)

| Mask name | Mask type | A-weighted sound power level dB (A) (uncertainty) | A-weighted sound pressure dB (A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift (*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |

(* one specimen only, measured using test method specified in ISO3744 in CPAP mode at 10 cmH$_2$O)

Sound Pressure Values of a Variety of Objects are Listed Below

| Object | A-weighted sound pressure dB (A) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

1.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, including one or more of comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO3744 in CPAP mode at 10 cmH$_2$O).

| RPT Device name | A-weighted sound power level dB (A) | Year (approx.) |
|---|---|---|
| C-Series Tango | 31.9 | 2007 |
| C-Series Tango with Humidifier | 33.1 | 2007 |
| S8 Escape II | 30.5 | 2005 |
| S8 Escape II with H4i Humidifier | 31.1 | 2005 |
| S9 AutoSet | 26.5 | 2010 |
| S9 AutoSet with H5i Humidifier | 28.6 | 2010 |

One known RPT device used for treating sleep disordered breathing is the S9 Sleep Therapy System, manufactured by ResMed. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

1.2.3.3 Humidifier

Delivery of a flow of air without humidification may cause drying of airways. The use of a humidifier with a RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). As a result, a medical humidifier is preferably small for bedside placement, and it is preferably configured to only humidify and/or heat the flow of air delivered to the patient without humidifying and/or heating the patient's surroundings. Room-based systems (e.g. a sauna, an air conditioner, an evaporative cooler), for example, may also humidify air that is breathed in by the patient, however they would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

1.2.3.4 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a user's mouth the mandible is held in an advanced position. The length of the connecting rods may be adjusted to change the level of protrusion of the mandible. A dentist may determine a preferred level of protrusion for the mandible that will determine the length of the connecting rods Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

1.2.4 Monitoring Systems

Polysomnography (PSG) is a conventional system for diagnosis and prognosis of cardio-pulmonary disorders. PSG typically involves the placement of 15 to 20 contact sensors on a person in order to record various bodily signals such as electroencephalography (EEG), electrocardiography (ECG), electrooculograpy (EOG), etc. However, while they may be suitable for their usual application in a clinical setting, such systems are complicated and potentially expensive, and/or may be uncomfortable or impractical for a patient at home trying to sleep.

The designer of a device may be presented with an infinite number of choices to make to design a product or system. Design criteria often conflict, meaning that certain design choices are far from routine or inevitable. Furthermore, the comfort and efficacy of certain aspects may be highly sensitive to small, subtle changes in one or more parameters.

1.2.5 Detection of Periodic Breathing

Periodic breathing may refer to periodic increases and decreases in an amplitude of respiratory effort, for a period approximately between 50 and 100 seconds. According to the American Academy of Sleep Medicine (AASM) guidelines, an instance of periodic breathing may be deemed to have occurred when there are at least three complete cycles of waxing and waning within a 10-minute period. Periodic breathing may be a common manifestation of central sleep apnea, often seen in heart failure patients.

One example of periodic breathing is CSR. The CSR patient may have heart failure or have suffered a brain stem lesion (i.e., stroke). Breathing in a CSR patient may be characterized by a "waxing and waning" tidal volume as respiration alternates between repetitive episodes of apnea/hypopnea and hyperpnea. This pattern may be caused by a combination of (i) excessive delay of the signals from the blood gas receptors to the respiratory center and (ii) excessive 'loop' gain, a combination of plant gain and controller gain.

Current techniques for detecting period breathing typically rely on either full lab polysomnography or reduced polygraphy systems. Such systems include, for example, a Philips Respironics Alice system and a ResMed's ApneaLink system, among other possibilities. Such systems may measure airflow and respiratory efforts at a patient's abdomen and thorax. For instance, the ResMed's ApneaLink system may measure a nasal flow signal, classify it as unambiguously CSR or nearly so, and display a likely record to a clinician for expert confirmation. The clinician may determine patterns of increased and reduced airflow and estimate the time of periodic breathing through visual inspection or by analysis of an envelope of the airflow and respiratory effort signals.

While the examination by a clinician is the most comprehensive method, it is a costly process and depends heavily upon clinical experience and understanding. As such, it will be appreciated that there may be a need for improved techniques to diagnosis and screen for periodic breathing.

2. BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

Some versions of the present technology may include an apparatus configured as a detector to detect periodic breathing, such as with one or more processors.

Some versions of the present technology may include an apparatus configured to control a respiratory treatment based on detection of periodic breathing, such as with one or more a processors.

In some cases, the detection may be based on an electrocardiogram (ECG) signal, such as from ECG electrodes and/or an accelerometer signal, such as from an accelerometer.

Some versions of the present technology may include an apparatus for detecting periodic breathing in a patient. The apparatus may include a processor. The processor may be configured to receive an electrocardiogram (ECG) signal of the patient. The processor may be configured to derive a feature from the ECG signal. The processor may be configured to analyze the feature to determine an occurrence of periodic breathing. The apparatus may also include a memory for storing the ECG signal and/or a sensor to measure the ECG signal from the patient. The sensor may be a Holter monitor, a 12-lead ECG or a patch type ECG. In some cases, the processor may be configured to perform a time-domain analysis of the ECG signal. The processor may be configured to perform a frequency-domain analysis of the ECG signal. The processor may be configured to divide the ECG signal into a plurality of time segments of equal time length. The processor may be configured to determine whether each time segment of the plurality exhibits a characteristic of periodic breathing. The processor may be configured to determine a likelihood of the patient having periodic breathing. The processor may be configured to derive a respiratory signal from the ECG signal. The processor may be configured to analyze an envelope of the derived respiratory signal.

Optionally, the feature may be a power spectral density of RR intervals in the ECG signal. The feature may be a power spectral density of ECG-derived respiration (EDR) numbers. An EDR number may be a magnitude of a QRS peak in the ECG signal. An EDR number may be an integral of an area around a QRS peak in the ECG signal. The processor may be configured to determine the occurrence of periodic breathing by comparing the feature in a respiration frequency range to a predetermined threshold. The processor may be configured to perform baseline correction on the ECG signal.

In some cases, the processor may be configured to receive an accelerometer signal indicative of the patient's position, derive a feature from the accelerometer signal, and analyze the feature derived from the accelerometer signal to determine an or said occurrence of periodic breathing. The apparatus may include a sensor to measure the accelerometer signal and/or generate the accelerometer signal. The apparatus may include a sensing device configured to measure the accelerometer signal and the ECG signal. The sensing device may be a patch type ECG. The feature derived from the accelerometer signal may be a respiratory effort feature. The feature derived from the accelerometer signal may be a power spectral density of a demodulated envelope signal of the accelerometer signal. The processor may be configured to remove a movement artefact from the accelerometer signal. The apparatus may include a filter, such as a band-pass filter, to filter the accelerometer signal. The occurrence of the periodic breathing may be Cheyne-Stokes respiration.

Optionally, the processor may be configured to combine features from the accelerometer signal and the ECG signal, in order to determine the occurrence of periodic breathing. The combined features may include RR-interval, EDR and Respiratory Effort extracted features. In some cases, the processor may be configured to determine power spectrum of RR interval times or relative QRS amplitude values on a segment-by-segment basis. The processor may be configured to integrate the power spectrum in a predetermined range to output a CSR band power value. The processor may be configured to compare CSR band power values to a predetermined threshold to detect significant CSR band power values. The processor may be configured to count significant CSR band power values. The processor may be configured to present a ratio of the count of significant CSR band power values and a number of segments. The processor may be configured to determine an average CSR frequency or average cycle length from segments selected according to significant CSR band power values.

Some versions of the present technology may include a method for detection of periodic breathing, such as with one or more processors.

Some versions of the present technology may include a method of control of a respiratory treatment based on detection of periodic breathing, such as with one or more a processors.

In some cases, the method of detection may be based on an electrocardiogram (ECG) signal, such as from ECG electrodes and/or an accelerometer signal, such as from an accelerometer.

Some versions of the present technology may involve a method for detecting periodic breathing in a patient. The method may include receiving, by a processor, an electrocardiogram (ECG) signal of the patient. The method may include deriving, by the processor, a feature from the ECG signal. The method may include analyzing, by the processor, the feature to determine an occurrence of periodic breathing.

In some cases, the method may include retrieving the ECG signal from a memory. The ECG signal may be provided by a sensor. The method may involve performing a time-domain analysis of the ECG signal. The method may include performing a frequency-domain analysis of the ECG signal. The method may include dividing the ECG signal into a plurality of time segments of equal time length. The method may include determining whether each time segment of the plurality exhibits a characteristic of periodic breathing. The method may include determining a likelihood of the patient having periodic breathing. The method may include deriving a respiratory signal from the ECG signal. The method may include analyzing an envelope of the derived respiratory signal. The feature may be a power spectral density of RR intervals in the ECG signal. The feature may be a power spectral density of ECG-derived respiration (EDR) numbers. An EDR number may be a magnitude of a QRS peak in the ECG signal. An EDR number may be an integral of an area around a QRS peak in the ECG signal.

The method may involve a processor determining the occurrence of periodic breathing by comparing the feature in a respiration frequency range to a predetermined threshold. The method may include performing baseline correction on the ECG signal. The method may also include receiving an accelerometer signal indicative of the patient's position, deriving a feature from the accelerometer signal, and analyzing the feature derived from the accelerometer signal to determine an occurrence of periodic breathing. The feature derived from the accelerometer signal may be a respiratory effort feature. The feature derived from the accelerometer signal may be a power spectral density of a demodulated envelope signal of the accelerometer signal. The method may involve removing a movement artefact from the accelerometer signal. The method may involve filtering the accelerometer signal by a filter, such as a band-pass filter. The occurrence of periodic breathing may be Cheyne-Stokes respiration.

The method may include combining features from the accelerometer signal and the ECG signal, in order to determine the occurrence of periodic breathing. The combined features may include RR-interval, EDR and/or Respiratory Effort extracted features. The analyzing may include determining power spectrum of RR interval times or relative QRS amplitude values on a segment-by-segment basis. The method may also include integrating the power spectrum in a predetermined range to output a CSR band power value. The method may include comparing CSR band power values to a predetermined threshold to detect significant CSR band power values. The method may include counting significant CSR band power values. The method may include presenting a ratio of the count of significant CSR band power values and a number of segments. The method may include determining an average CSR frequency or average cycle length from segments selected according to significant CSR band power values.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3. BRIEF DESCRIPTION OF THE DRAWINGS

The present technology is illustrated by way of example, and not by way of limitation, in the figures of the accompanying drawings, in which like reference numerals refer to similar elements including:

3.1 Treatment Systems

FIG. 1A shows a system including a patient 1000 wearing a patient interface 3000, in the form of a nasal pillows, receives a supply of air at positive pressure from a RPT device 4000. Air from the RPT device is humidified in a humidifier 5000, and passes along an air circuit 4170 to the patient 1000. A bed partner 1100 is also shown.

3.2 Respiratory System and Facial Anatomy

Figure 1A:
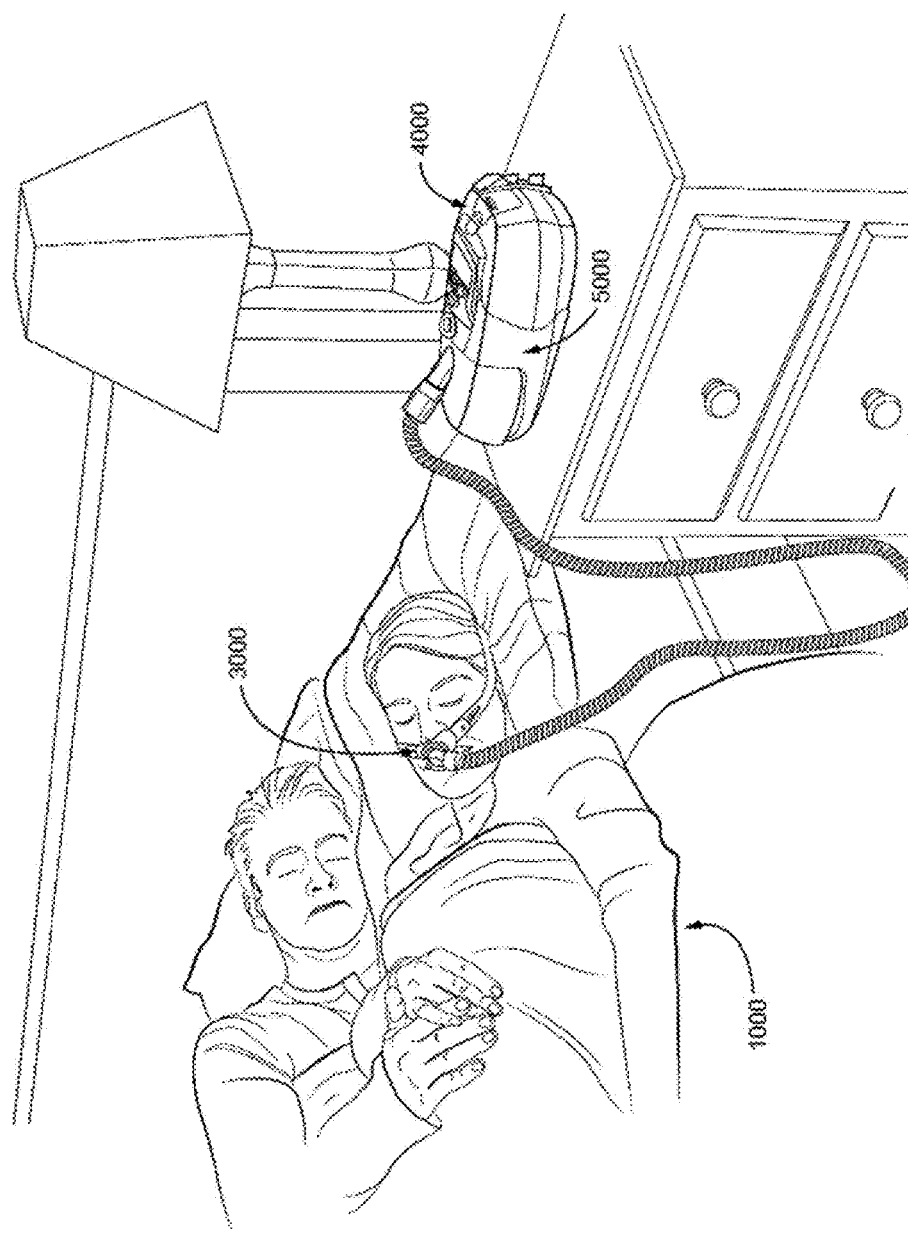
FIG. 1B shows a system including a patient 1000 wearing a patient interface 3000, in the form of a nasal mask, receives a supply of air at positive pressure from a RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receives a supply of air at positive pressure from a RPT device 4000. Air from the RPT device is humidified in a humidifier 5000, and passes along an air circuit 4170 to the patient 1000.
FIG. 1D shows a patient 1000 undergoing polysomnography (PSG).
Figure 1B:
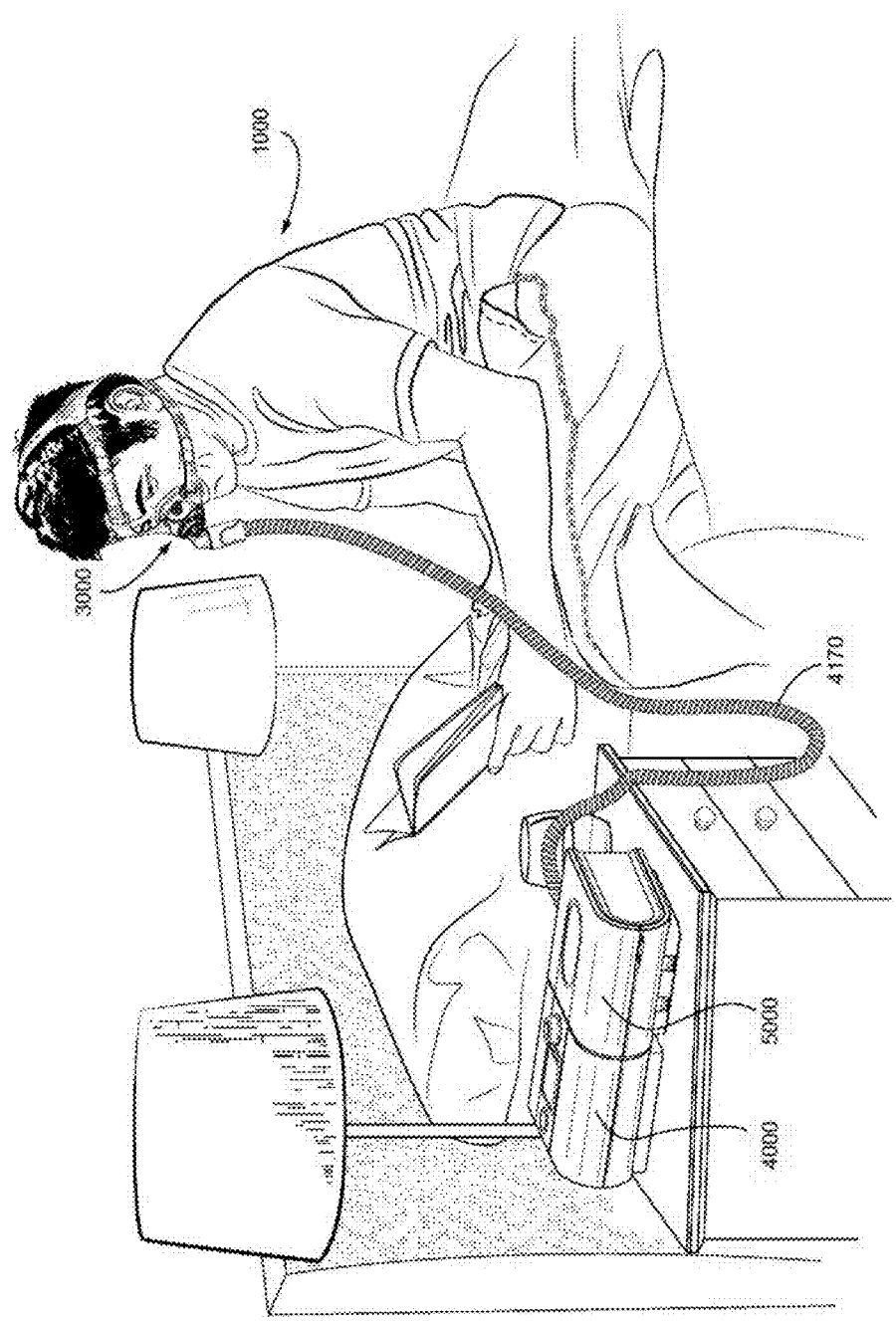
Figure 1C:
Figure 1D:
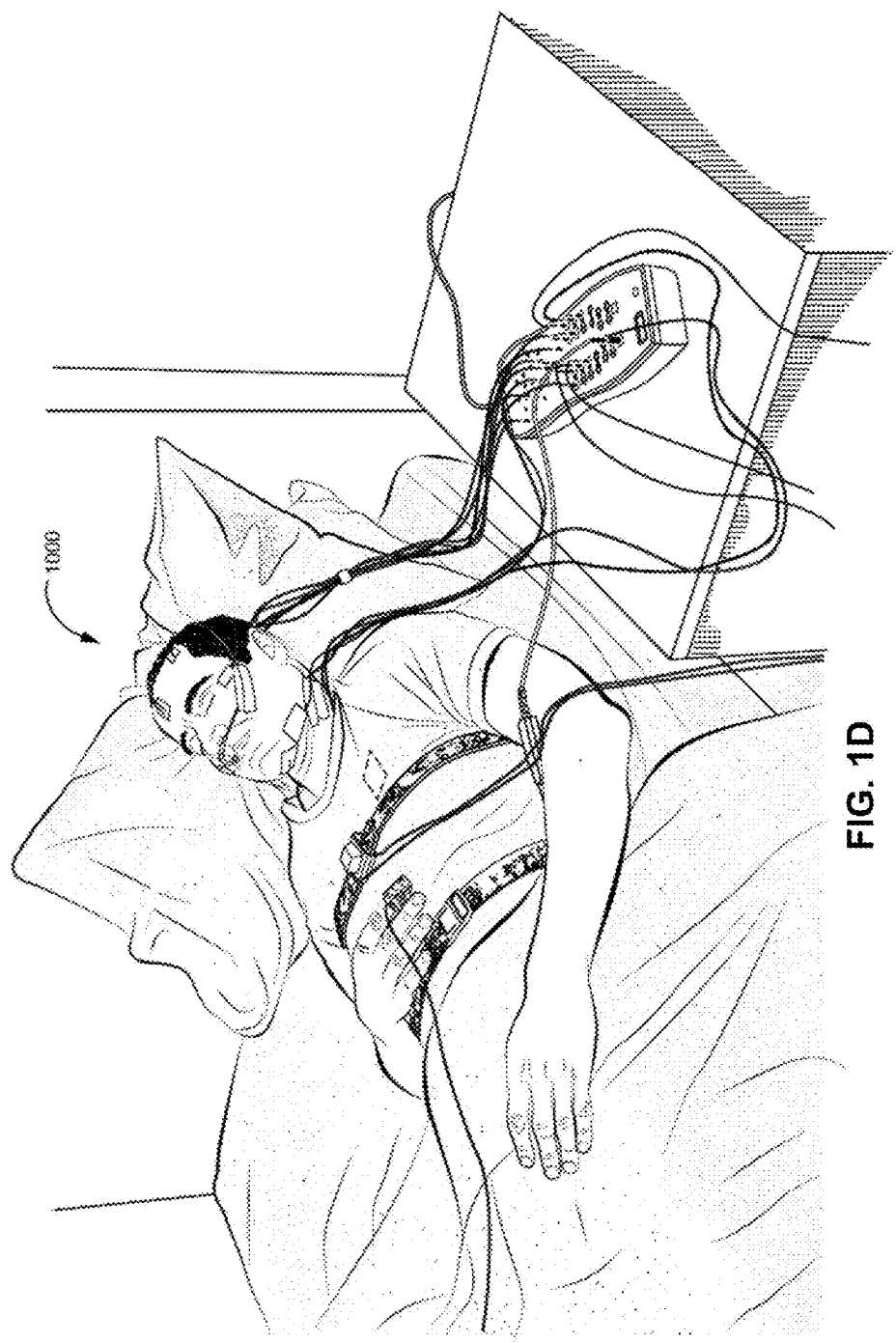
Figure 2A:
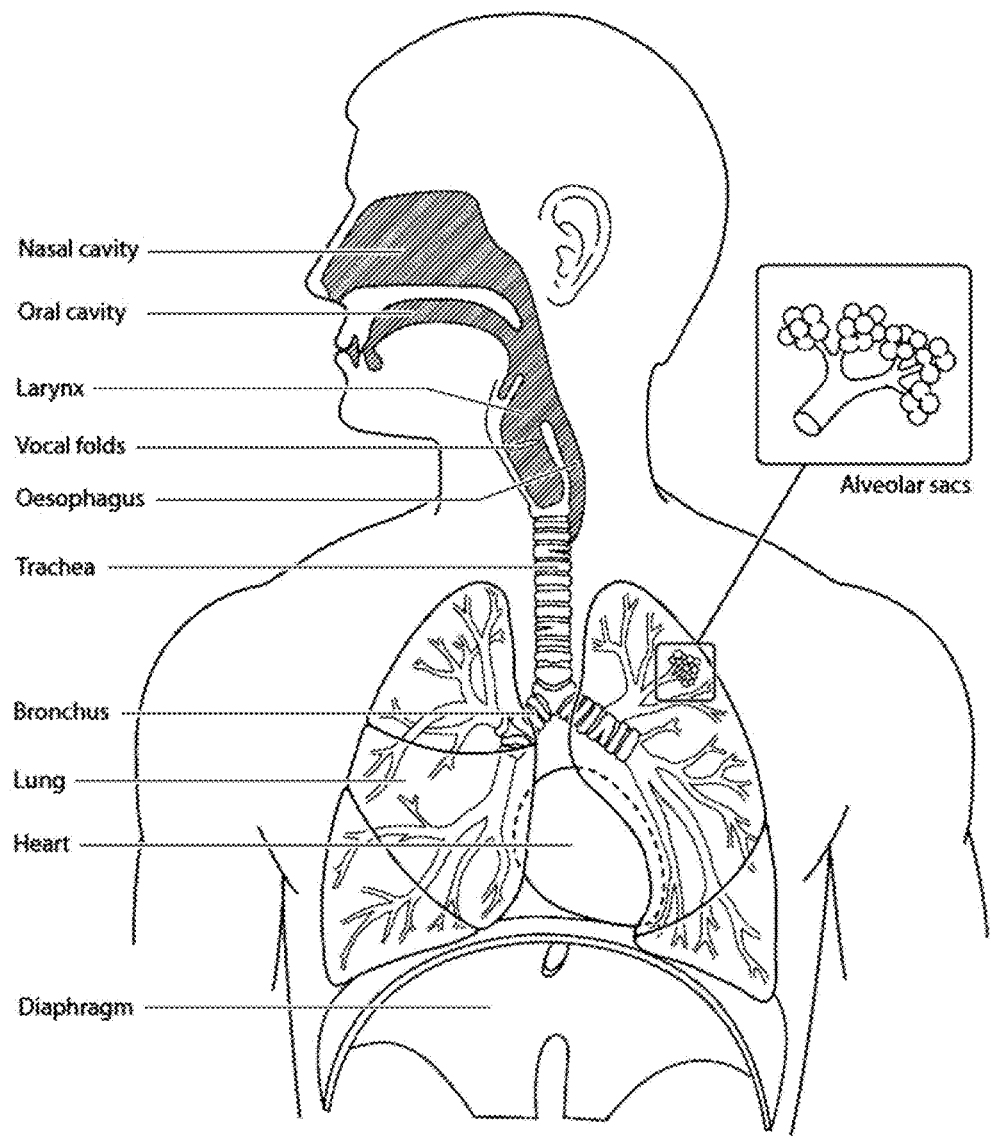

FIG. 2A shows an overview of a human respiratory system including the nasal and oral cavities, the larynx, vocal folds, oesophagus, trachea, bronchus, lung, alveolar sacs, heart and diaphragm.

Figure 2B:
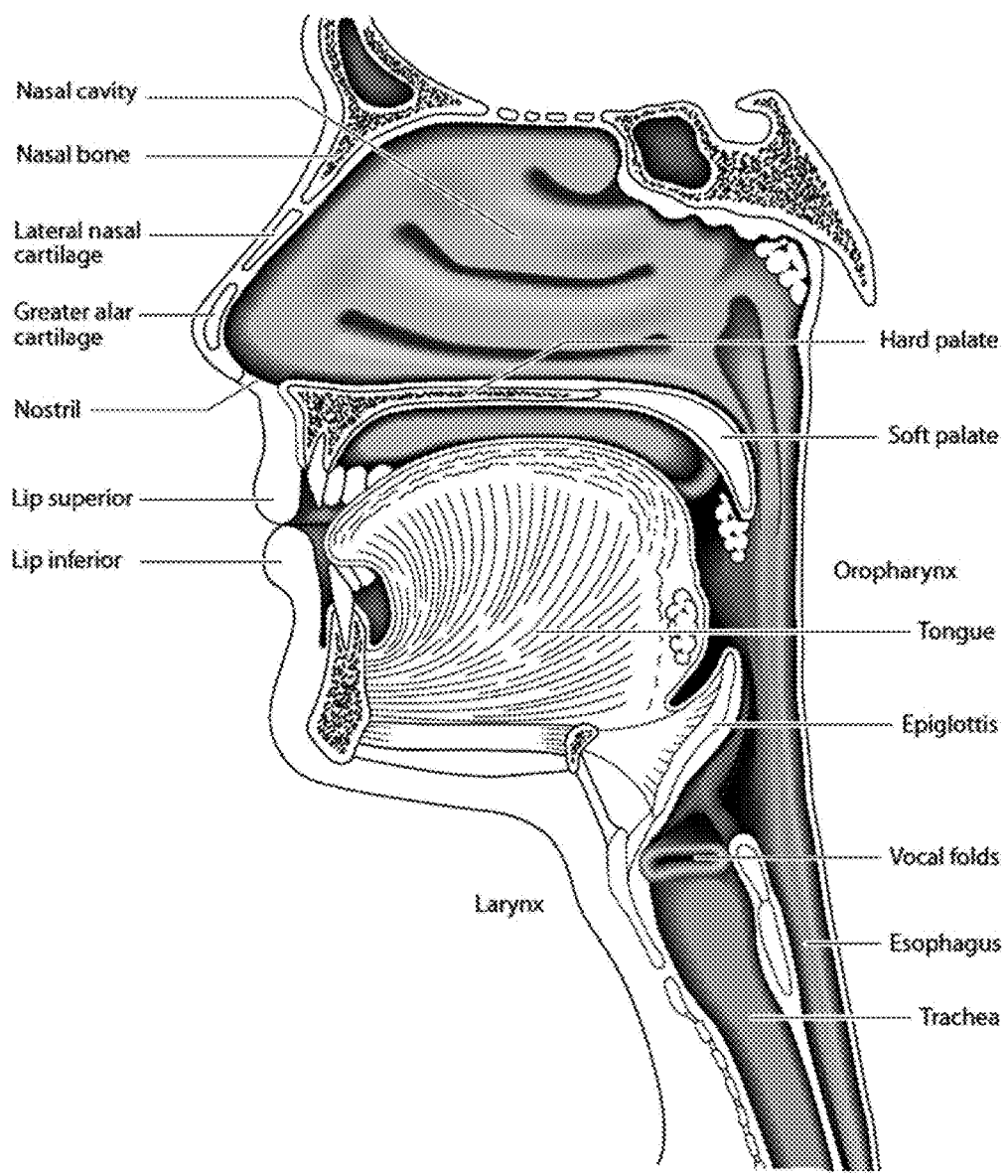

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

3.3 Patient Interface

Figure 3:
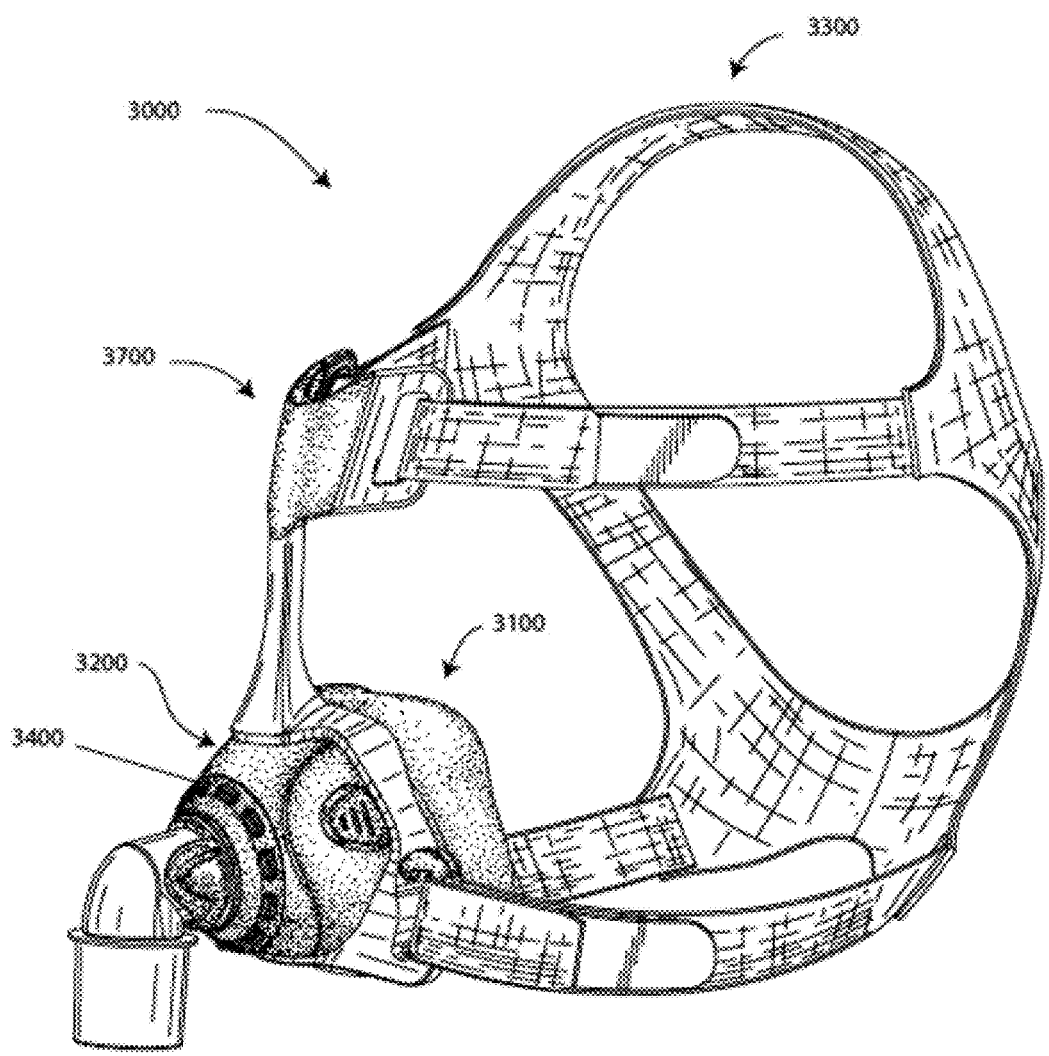

FIG. 3 shows a patient interface in the form of a nasal mask in accordance with one form of the respective technology.

3.4 RPT Device

Figure 4A:
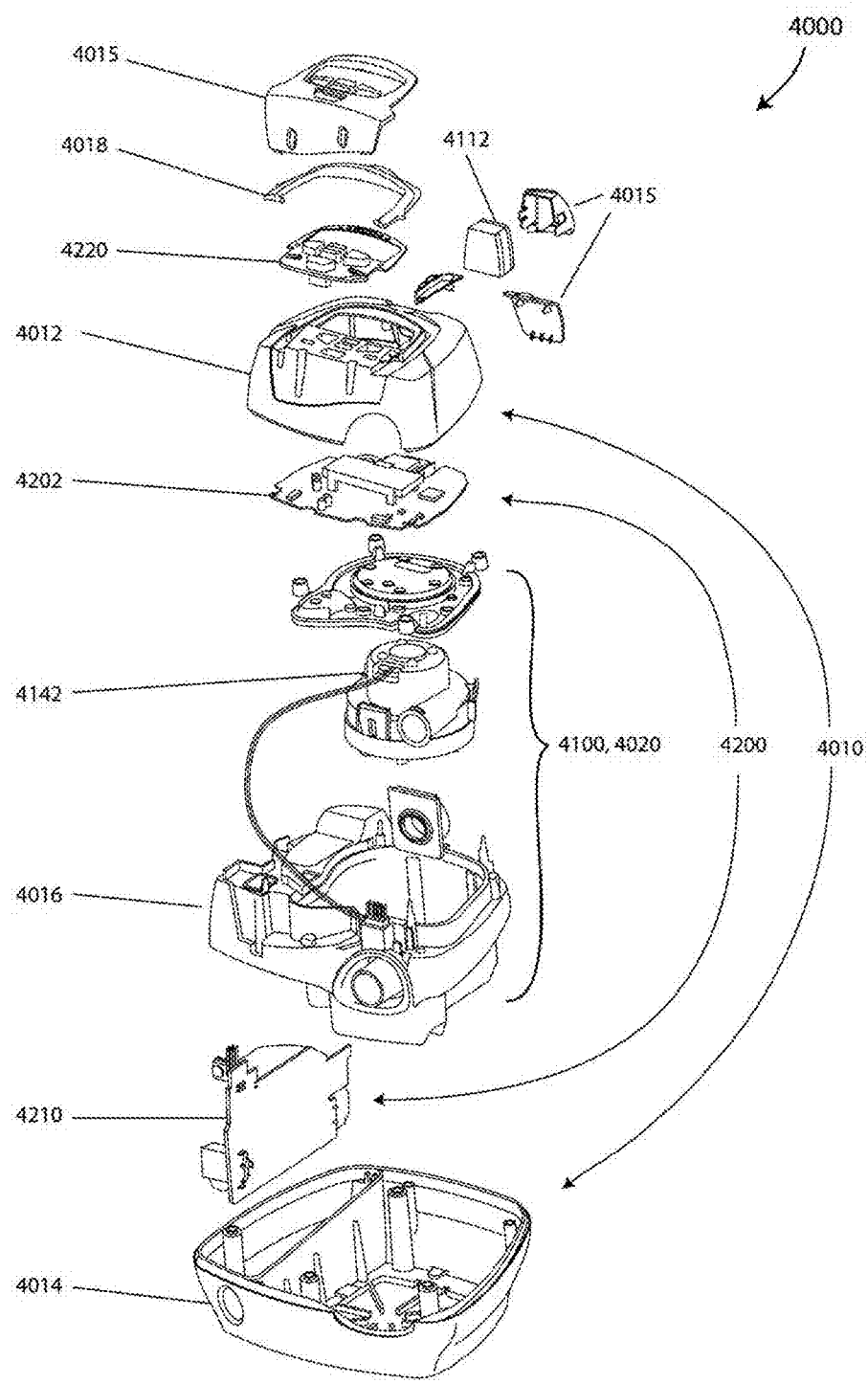

FIG. 4A shows a RPT device in accordance with one form of the respective technology.

Figure 4B:
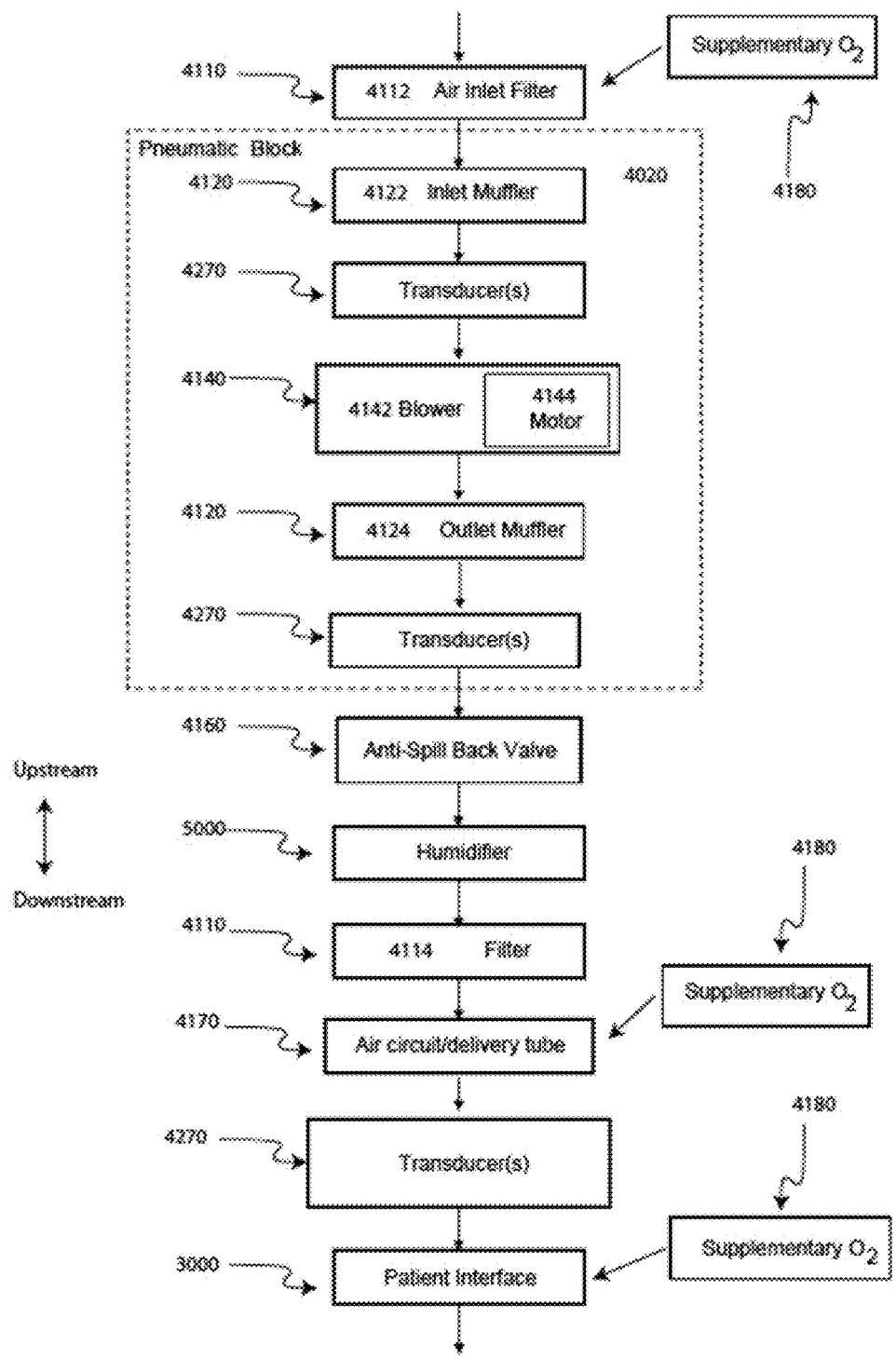

FIG. 4B shows a schematic diagram of the pneumatic path of a RPT device in accordance with one form of the respective technology. The directions of upstream and downstream are indicated.

Figure 4C:
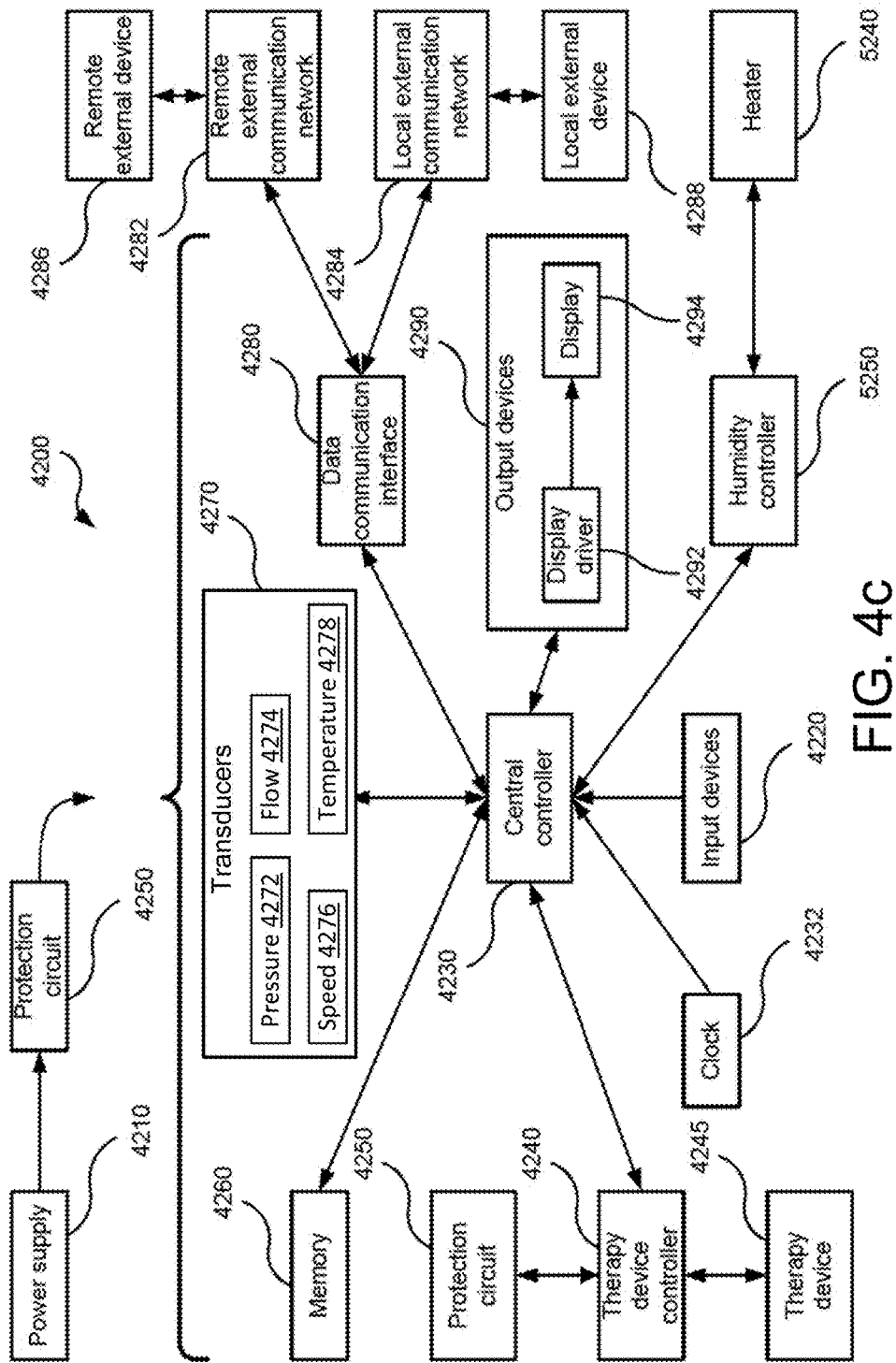

FIG. 4C shows a schematic diagram of the electrical components of a RPT device in accordance with one aspect of the respective technology.

Figure 4D:
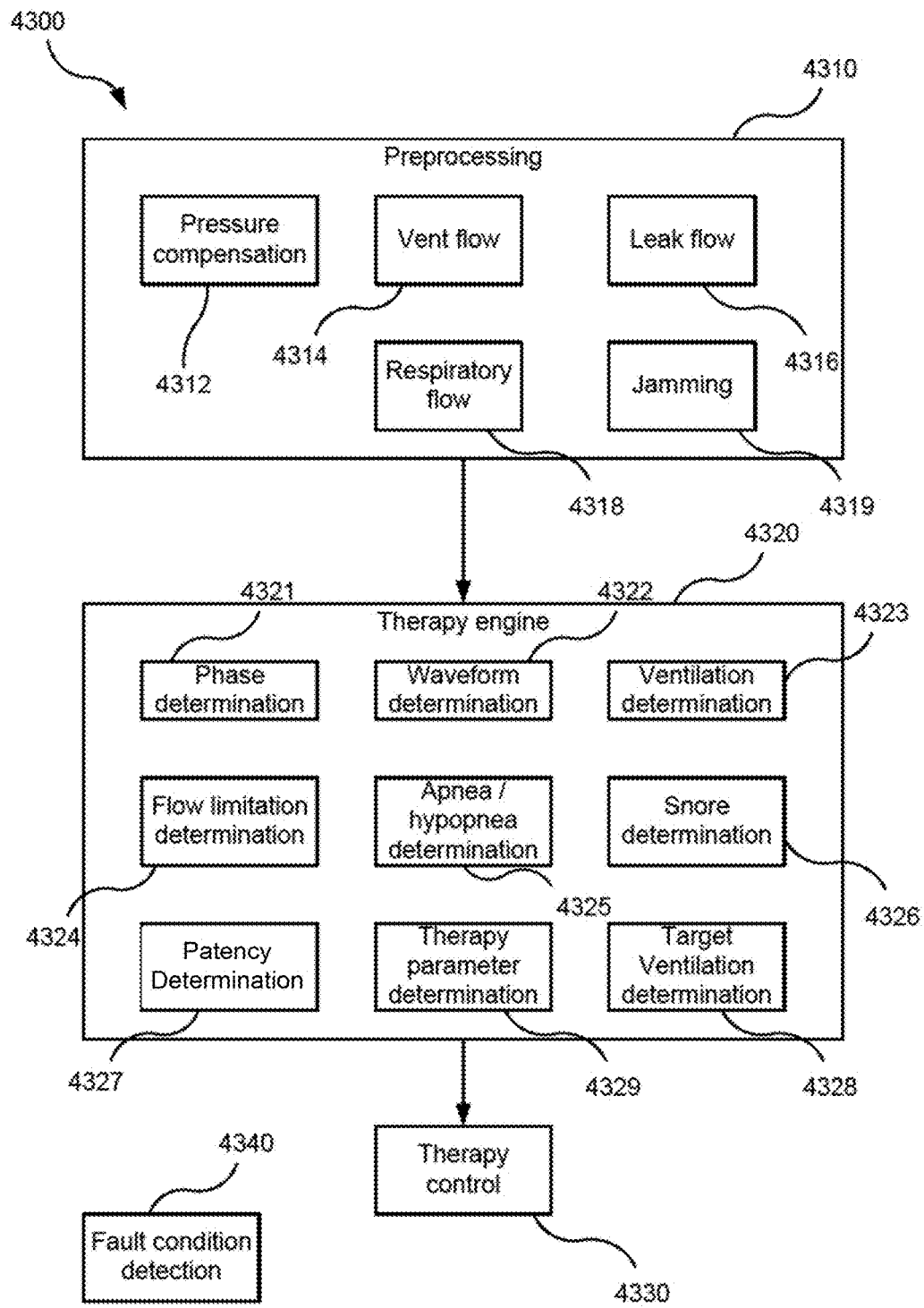

FIG. 4D shows a schematic diagram of the algorithms implemented in a RPT device in accordance with an aspect of the respective technology. In this figure, arrows with solid lines indicate an actual flow of information, for example via an electronic signal.

3.5 Humidifier

Figure 5:
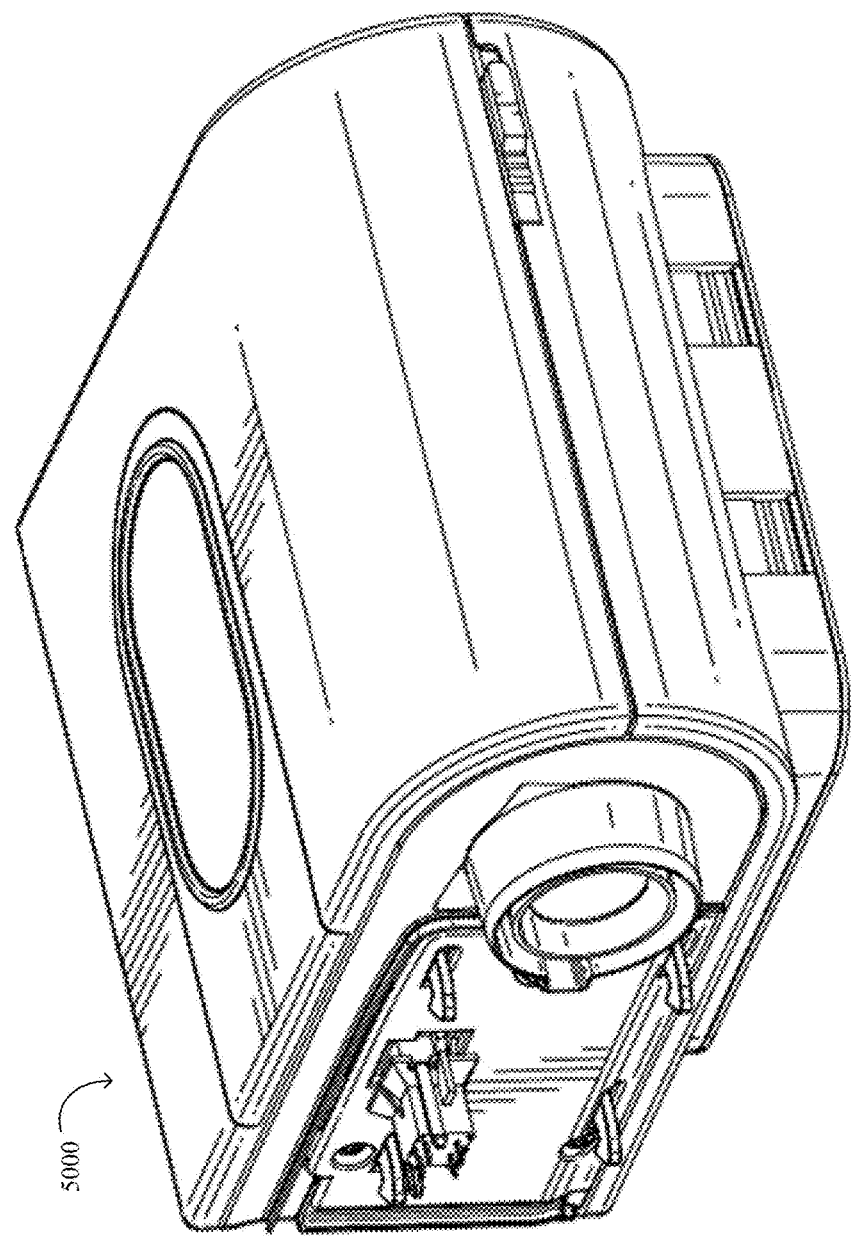

FIG. 5 shows an isometric view of a humidifier in accordance with one aspect of the respective technology.

3.6 Breathing Waveforms

Figure 6A:
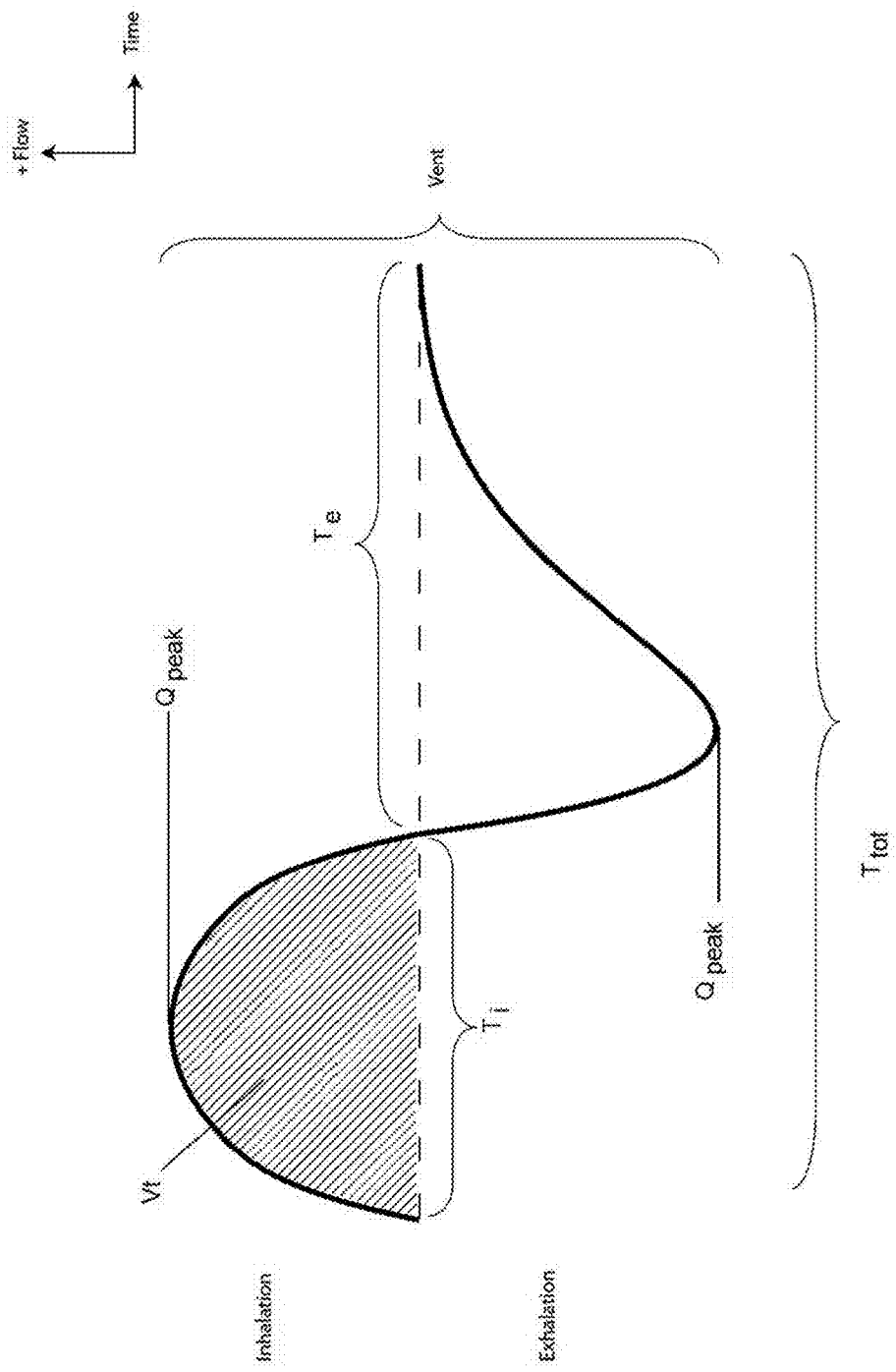

FIG. 6A shows a model typical breath waveform of a person while sleeping.

Figure 6B:
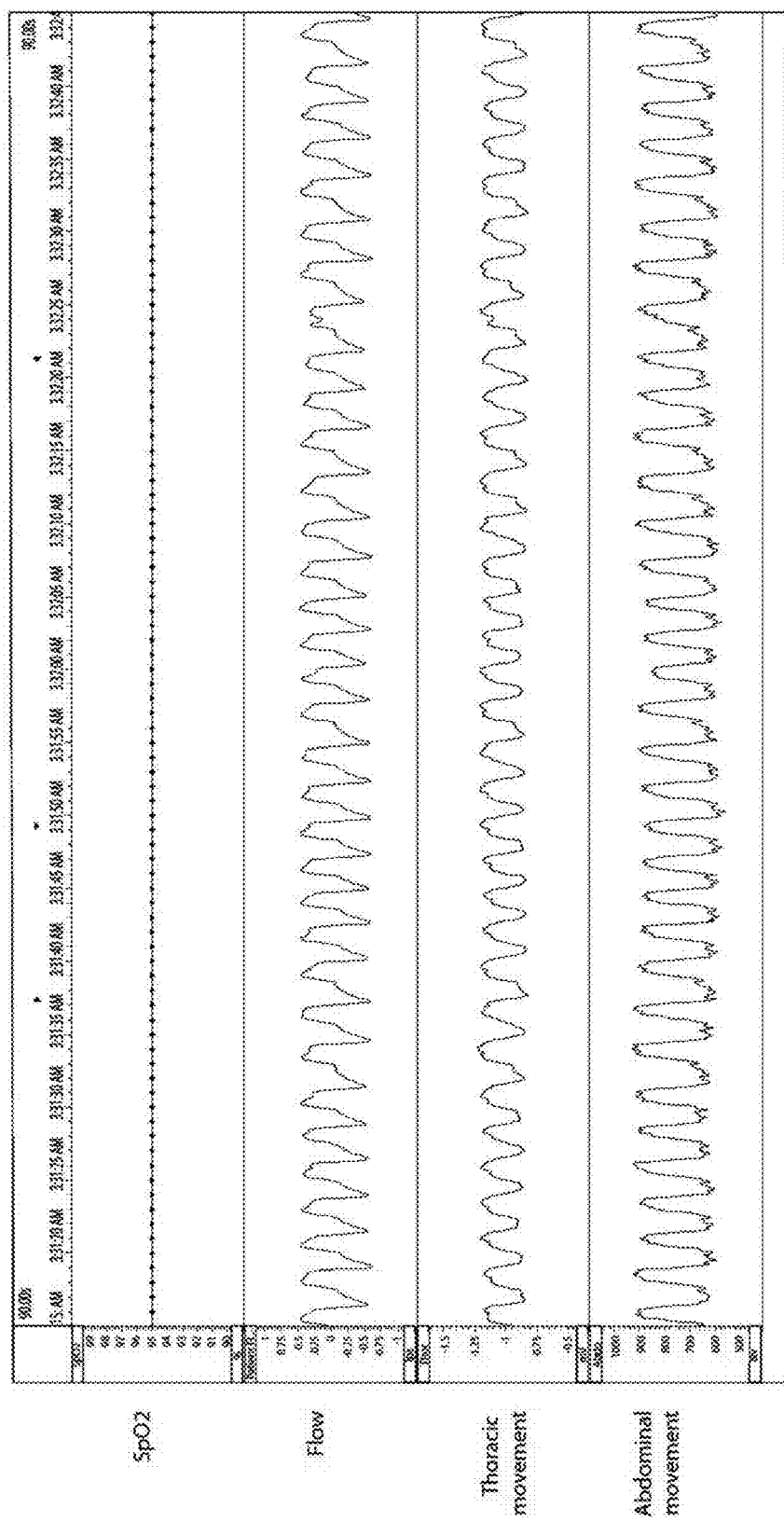

FIG. 6B shows a patient during Non-REM sleep breathing normally over a period of about ninety seconds.

Figure 6C:
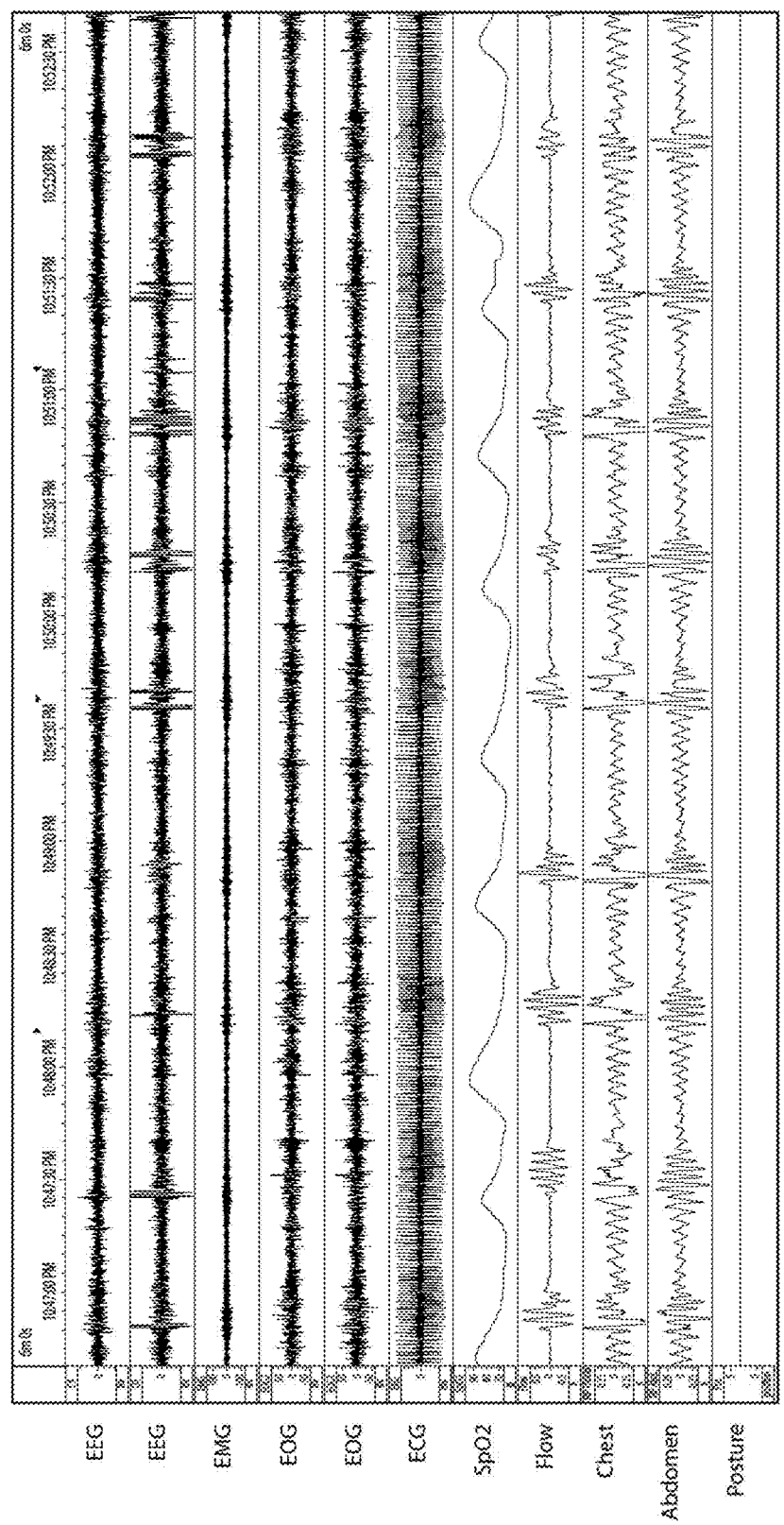

FIG. 6C shows polysomnography of a patient before treatment.

FIG. 6D shows patient flow data where the patient is experiencing a series of total obstructive apneas.

Figure 6E:
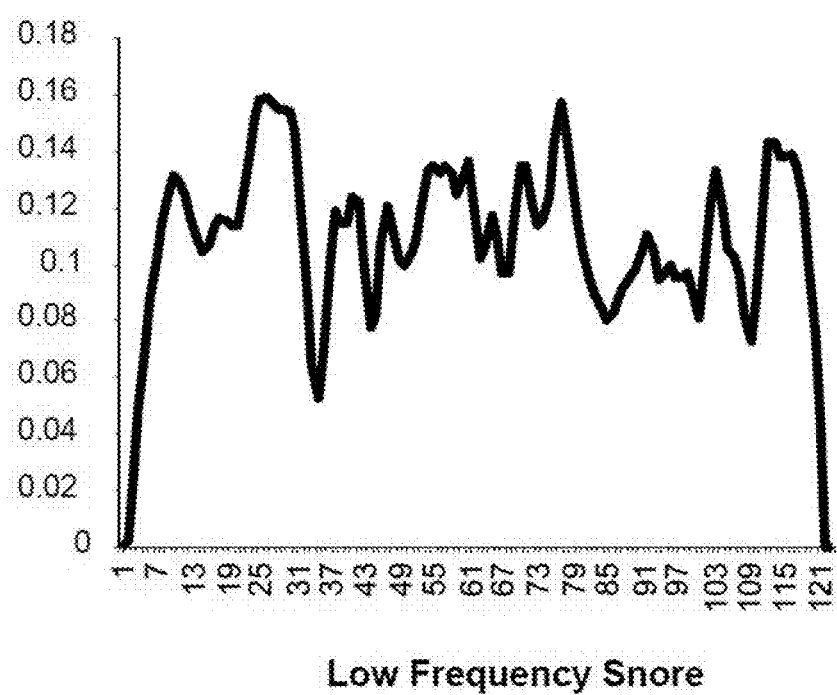

FIG. 6E shows a scaled inspiratory portion of a breath where the patient is experiencing low frequency inspiratory snore.

Figure 6F:
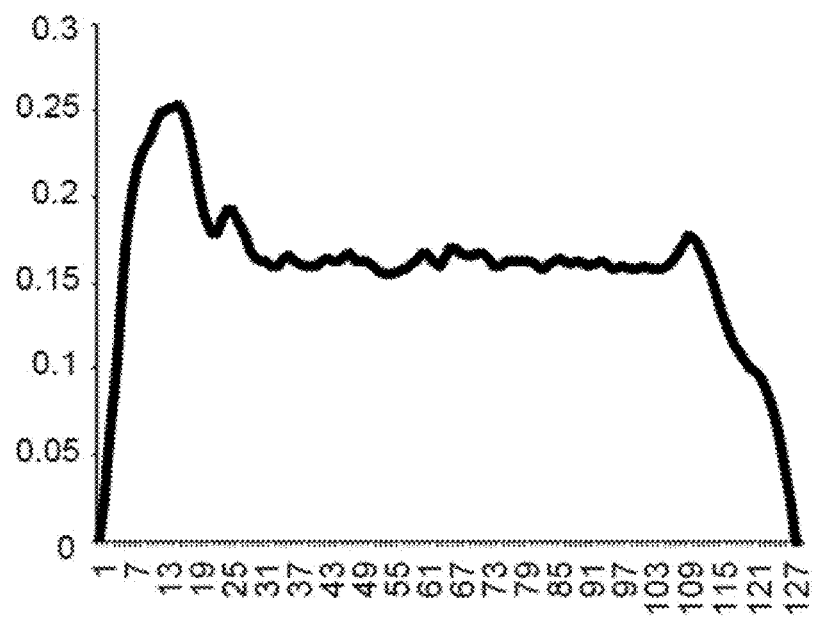

FIG. 6F shows a scaled inspiratory portion of a breath where the patient is experiencing an example of flattened inspiratory flow limitation.

Figure 6G:
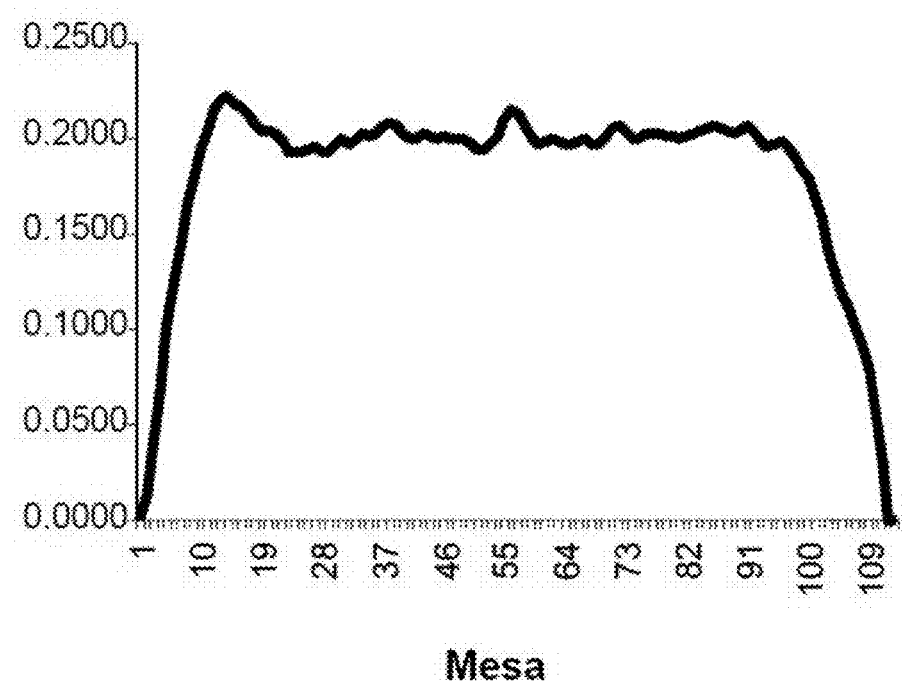

FIG. 6G shows a scaled inspiratory portion of a breath where the patient is experiencing an example of "mesa" flattened inspiratory flow limitation.

Figure 6H:
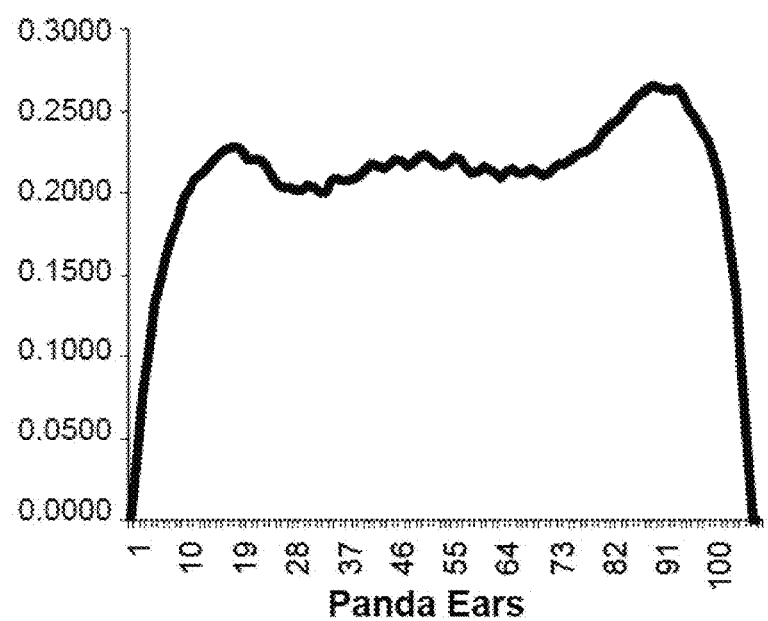

FIG. 6H shows a scaled inspiratory portion of a breath where the patient is experiencing an example of "panda ears" inspiratory flow limitation.

Figure 6I:
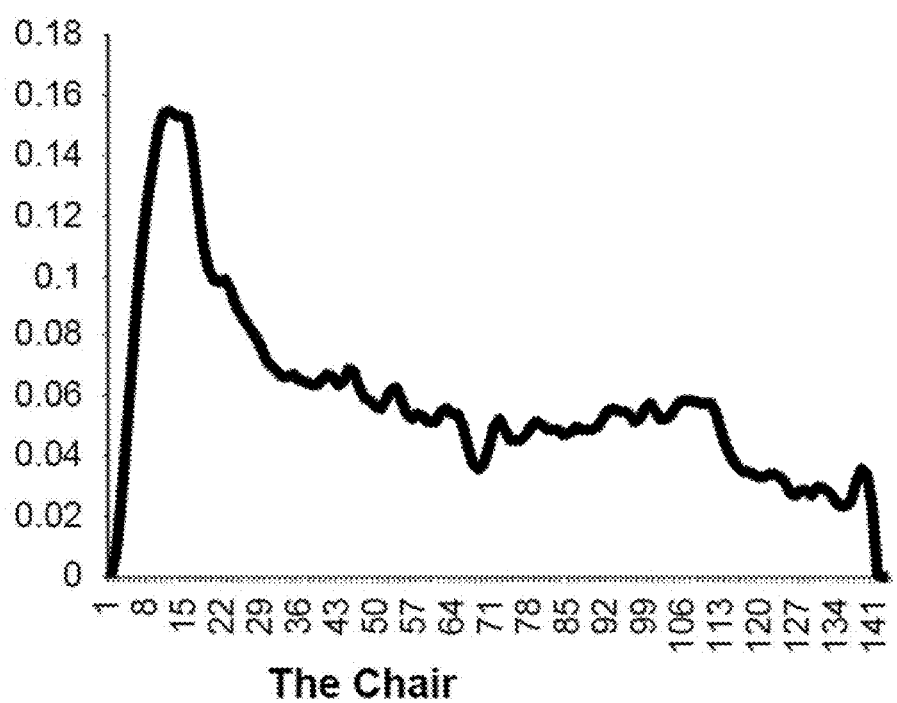

FIG. 6I shows a scaled inspiratory portion of a breath where the patient is experiencing an example of "chair" inspiratory flow limitation.

Figure 6J:
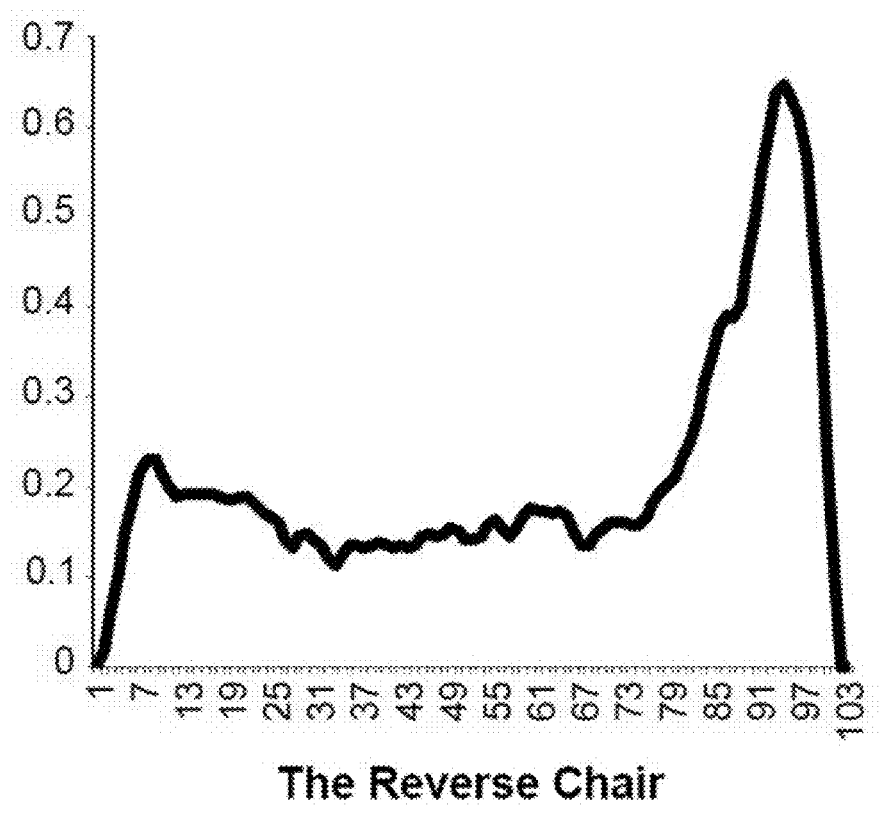

FIG. 6J shows a scaled inspiratory portion of a breath where the patient is experiencing an example of "reverse chair" inspiratory flow limitation.

Figure 6K:
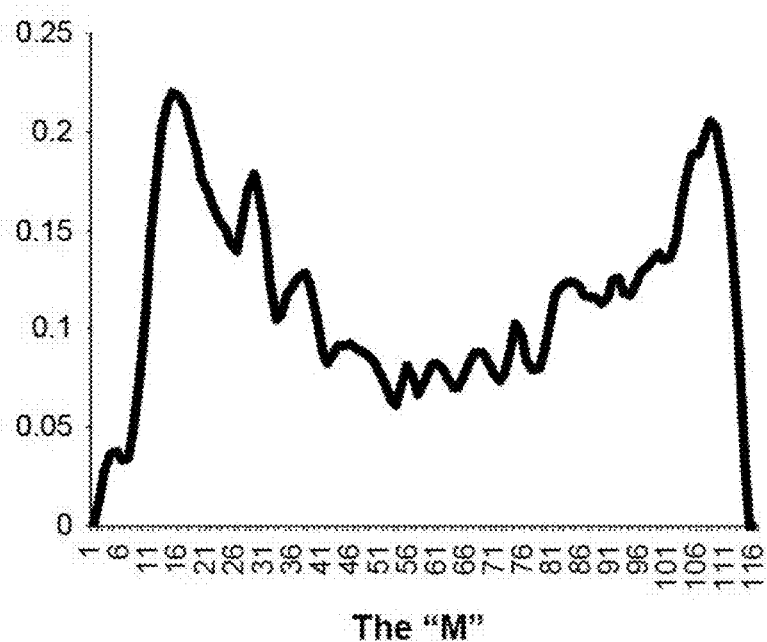
Figure 6I:
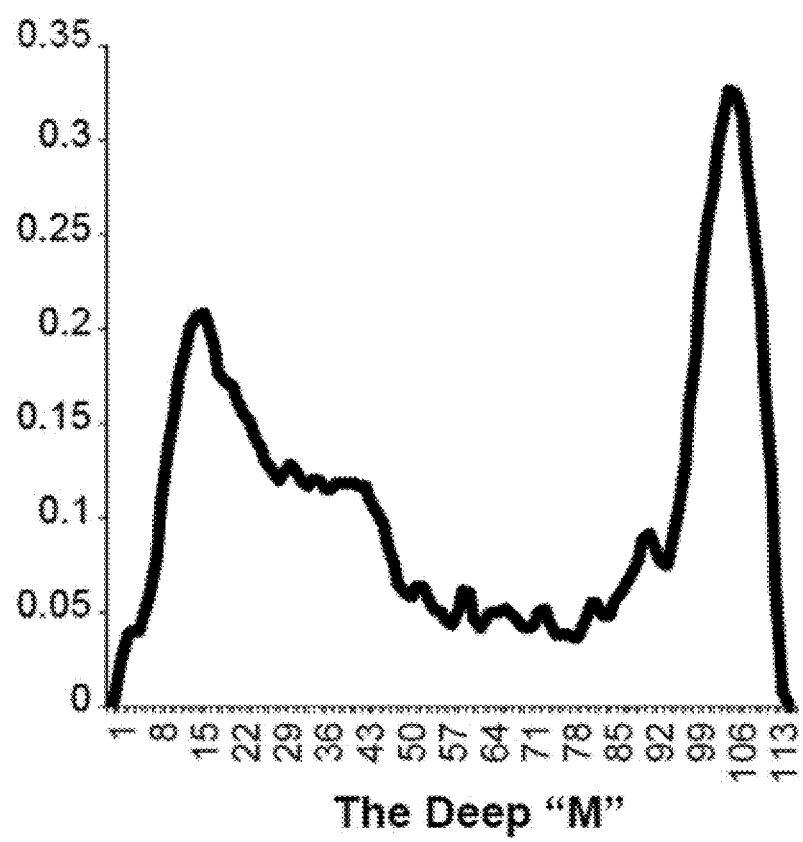

FIG. 6K shows a scaled inspiratory portion of a breath where the patient is experiencing an example of "M-shaped" inspiratory flow limitation.

FIG. 6L shows a scaled inspiratory portion of a breath where the patient is experiencing an example of severely "M-shaped" inspiratory flow limitation.

Figure 6M:
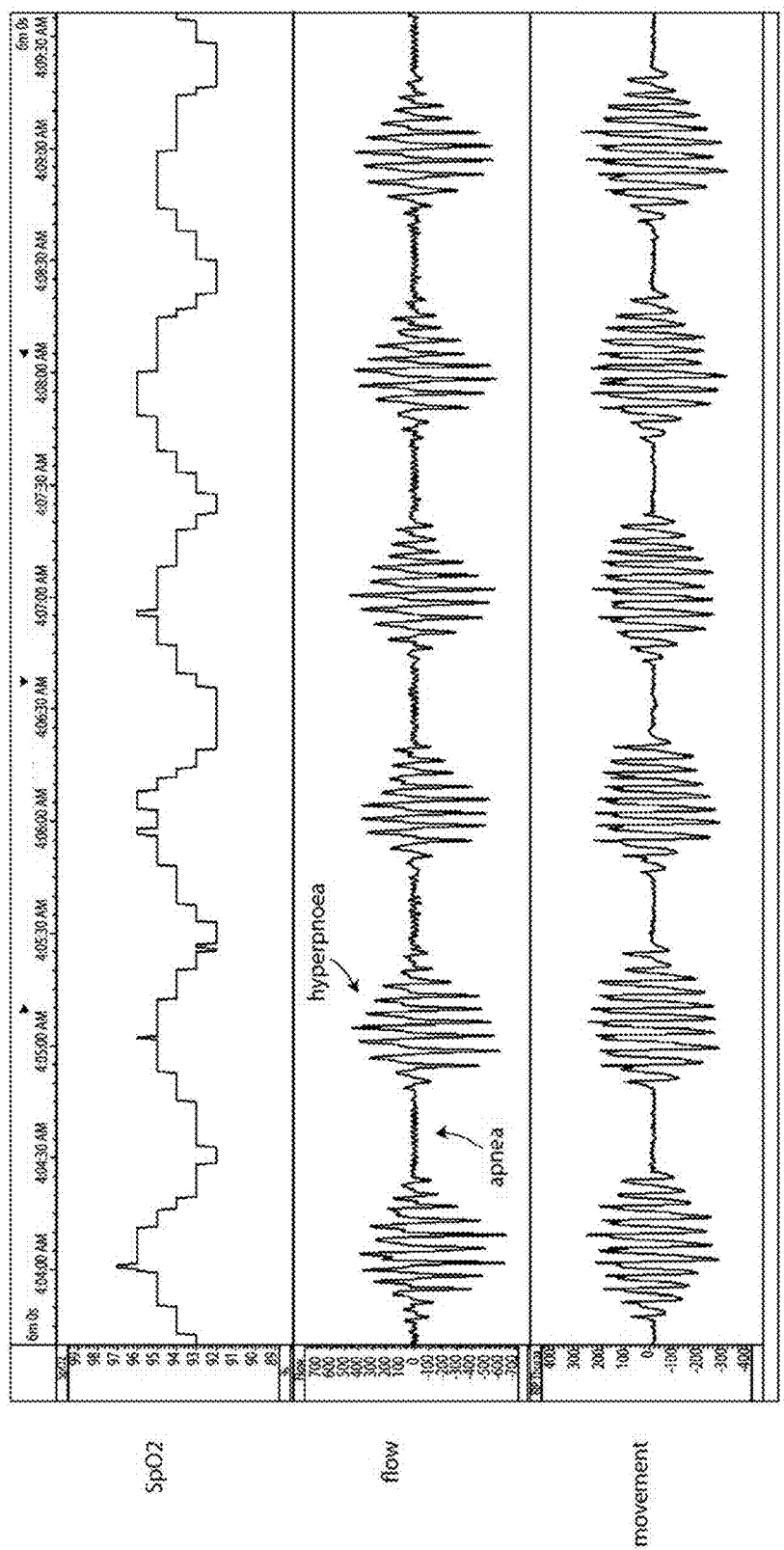

FIG. 6M shows patient data from a patient with Cheyne-Stokes respiration.

Figure 6N:
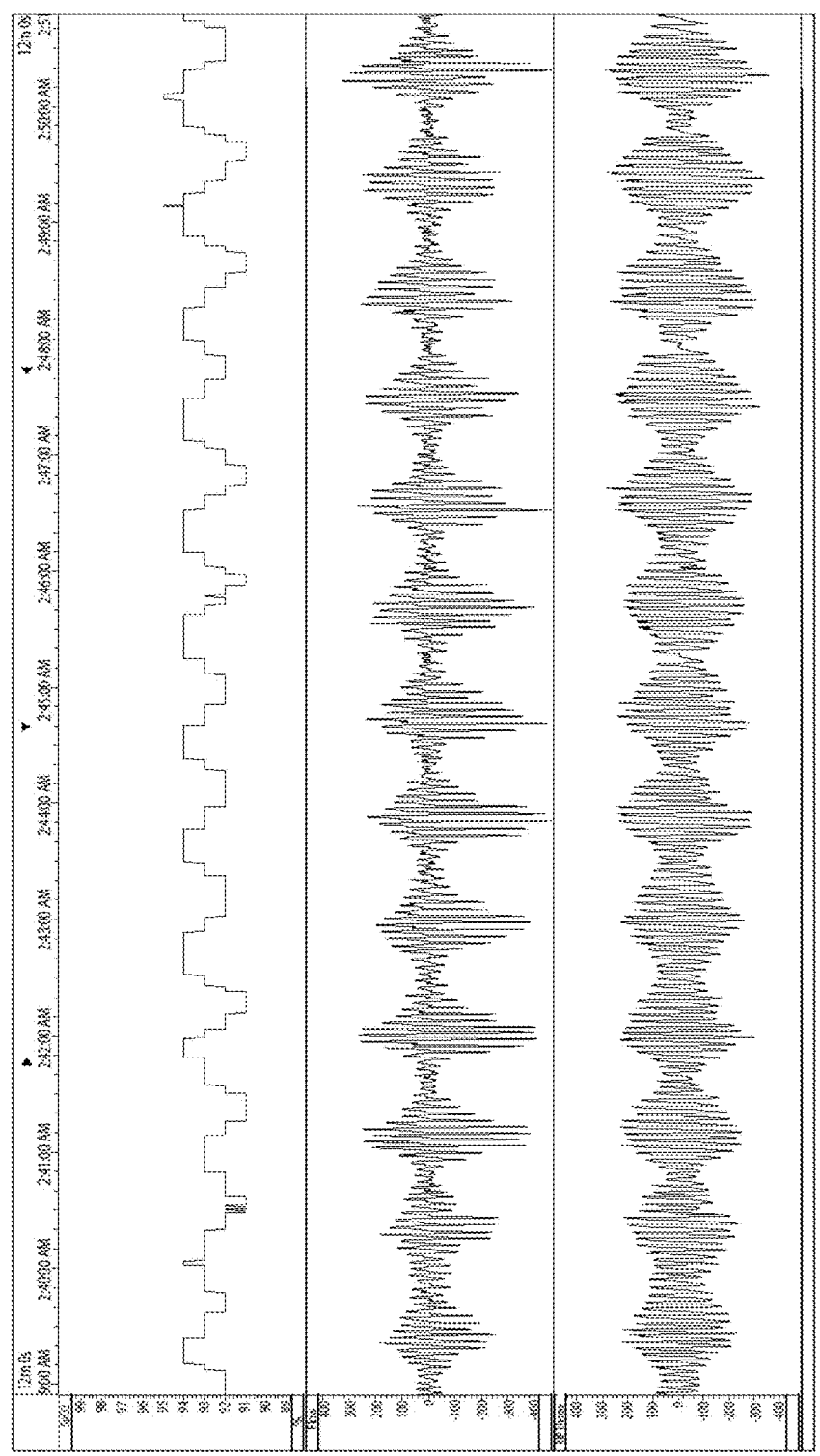
Figure 60:
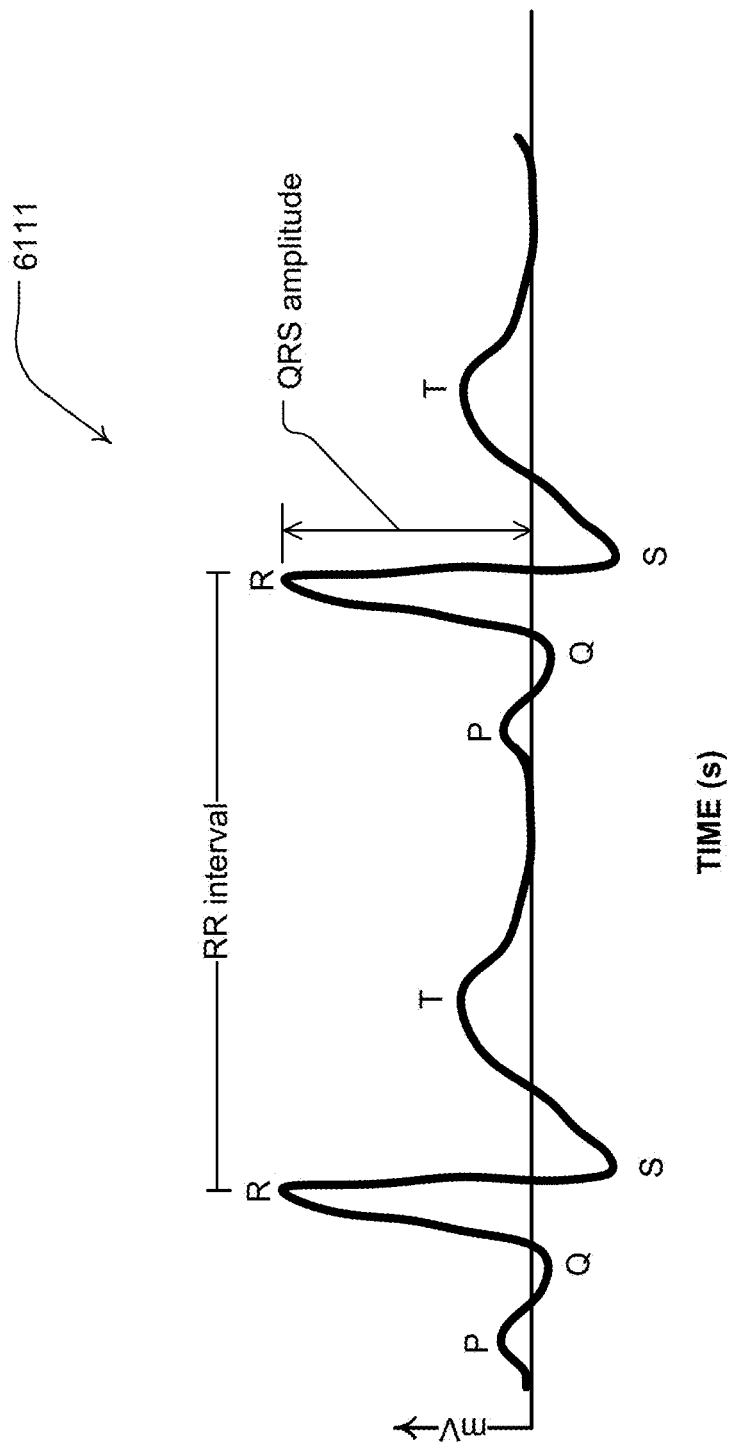

FIG. 6N shows patient data from a patient with another example of Cheyne-Stokes respiration, using the same three channels as in FIG. 6m.

3.7 Cardiac Waveforms

FIG. 6O illustrates a typical ECG signal that could be recorded using either a surface electrode or an internal sensing lead. The exact shape of the QRS complex can vary depending on lead position; the diagram shows a typical shape for a Lead II configuration. The QRS amplitude is the amplitude of the signal above a nominal baseline. The RR interval is the time between sequential heart beats.

3.8 Detection of Periodic Breathing from Electrocardiogram

Figure 7:
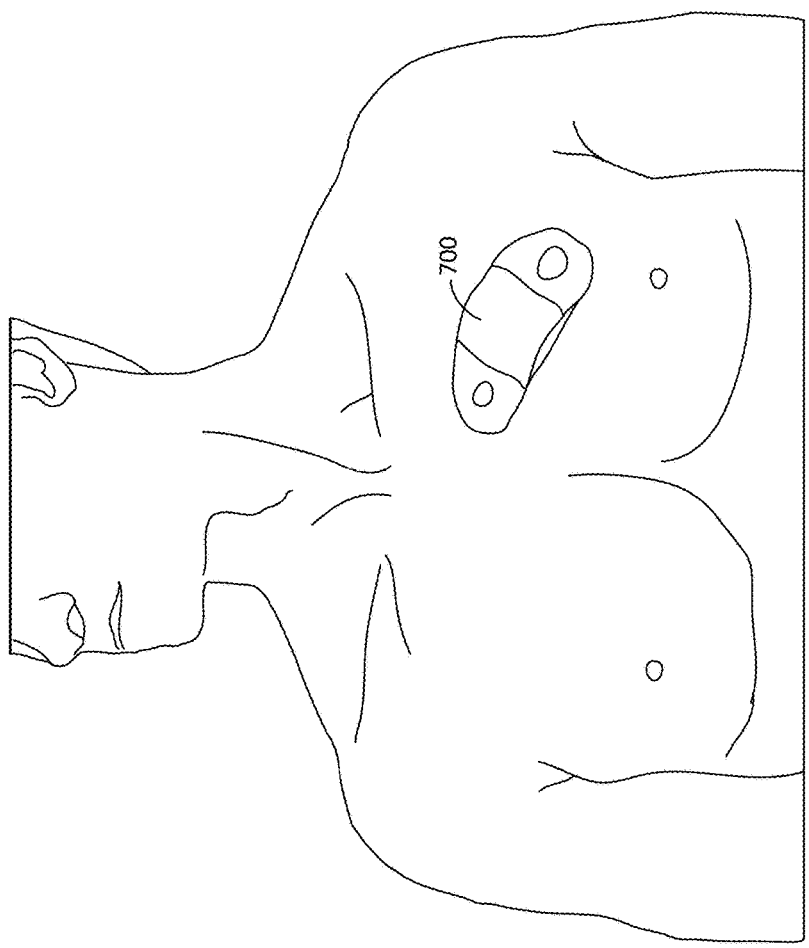

FIG. 7 shows an example of a surface ECG patch.

Figure 8:
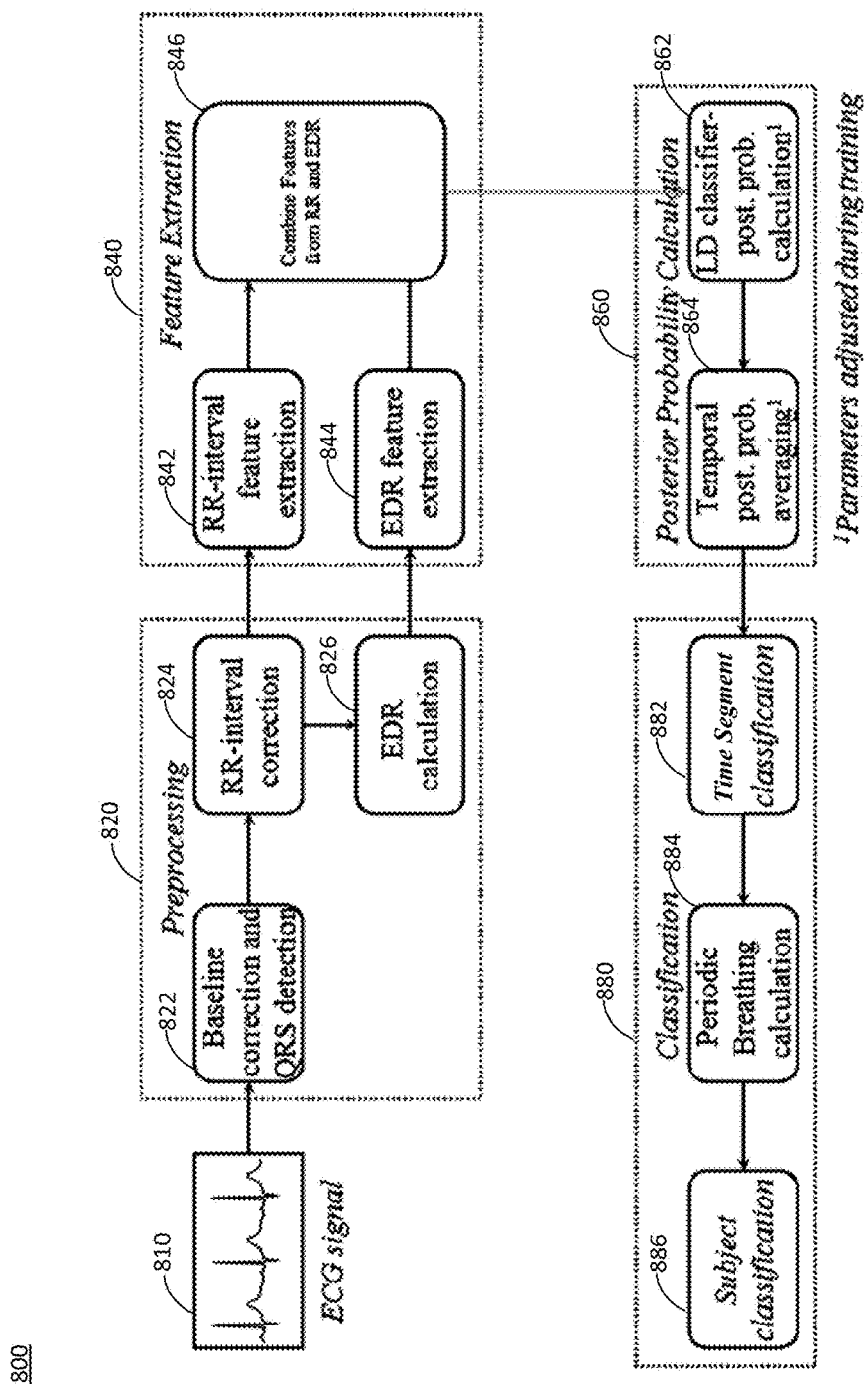

FIG. 8 illustrates a block diagram of a system configured to detect periodic breathing based on an ECG signal.

Figure 8A:
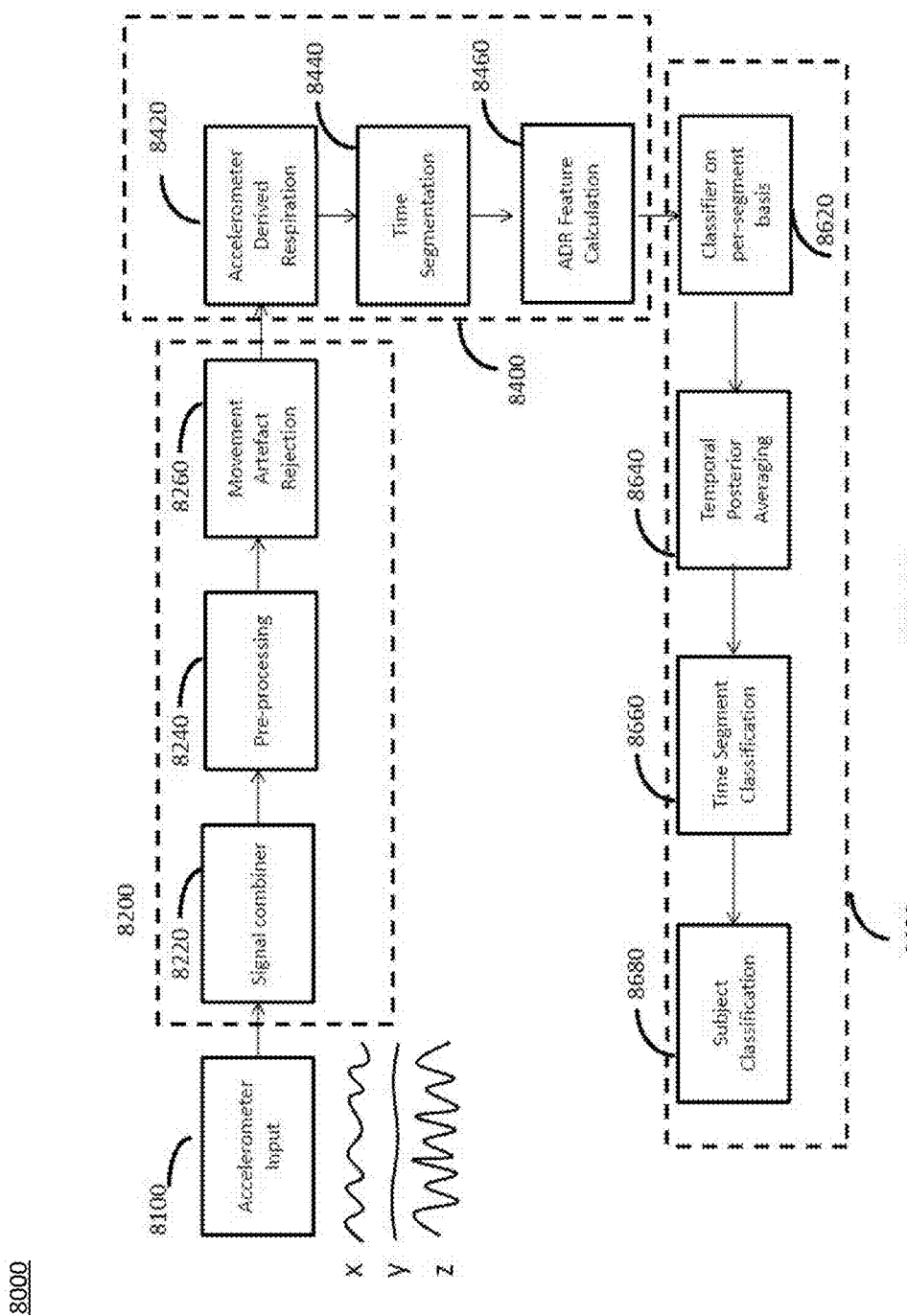

FIG. 8A illustrates a block diagram of a system configured to detect periodic breathing based on an accelerometer signal.

Figure 9:
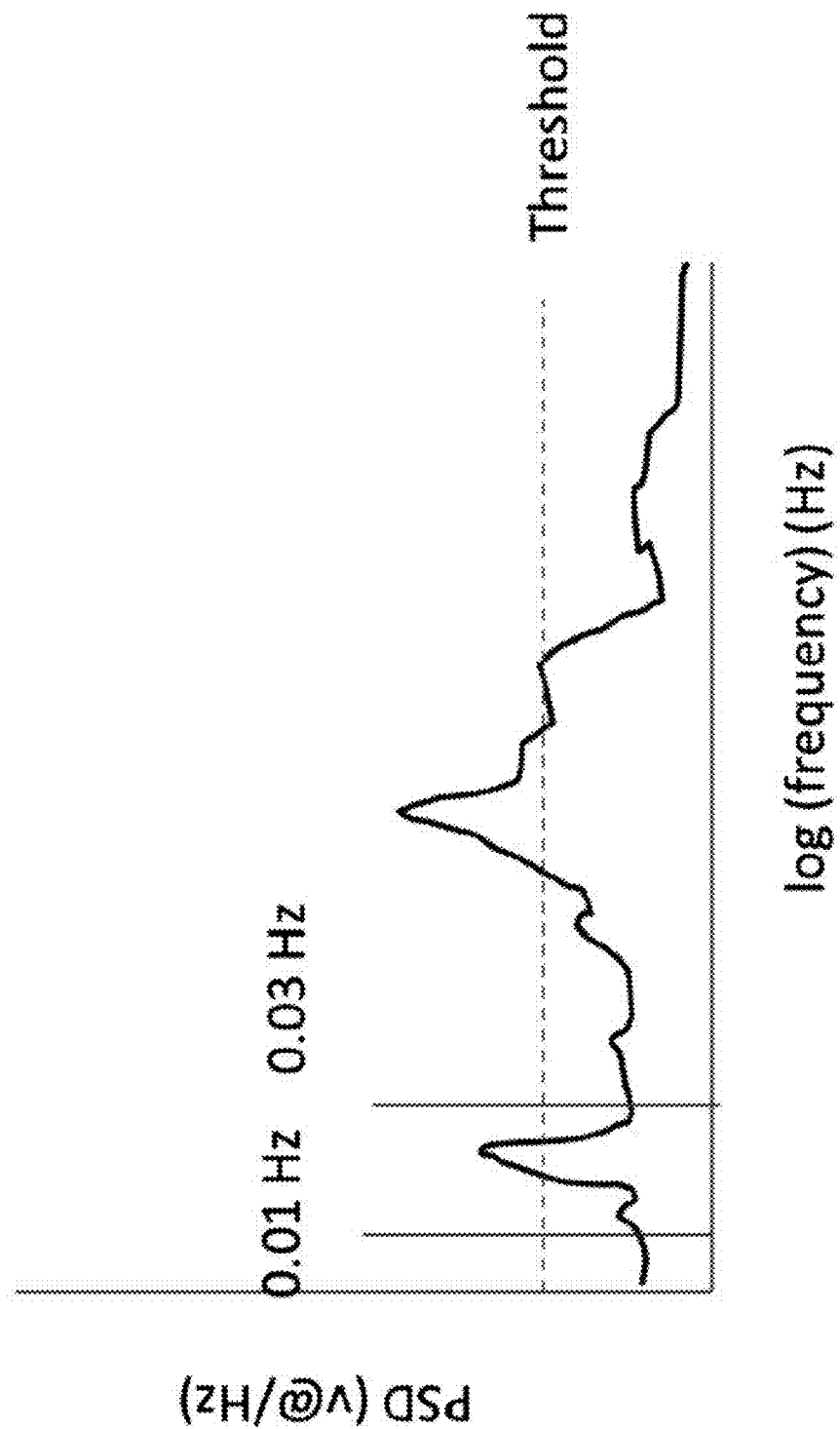

FIG. 9 illustrates a graph of a power spectral density as a function of frequency.

Figure 10:
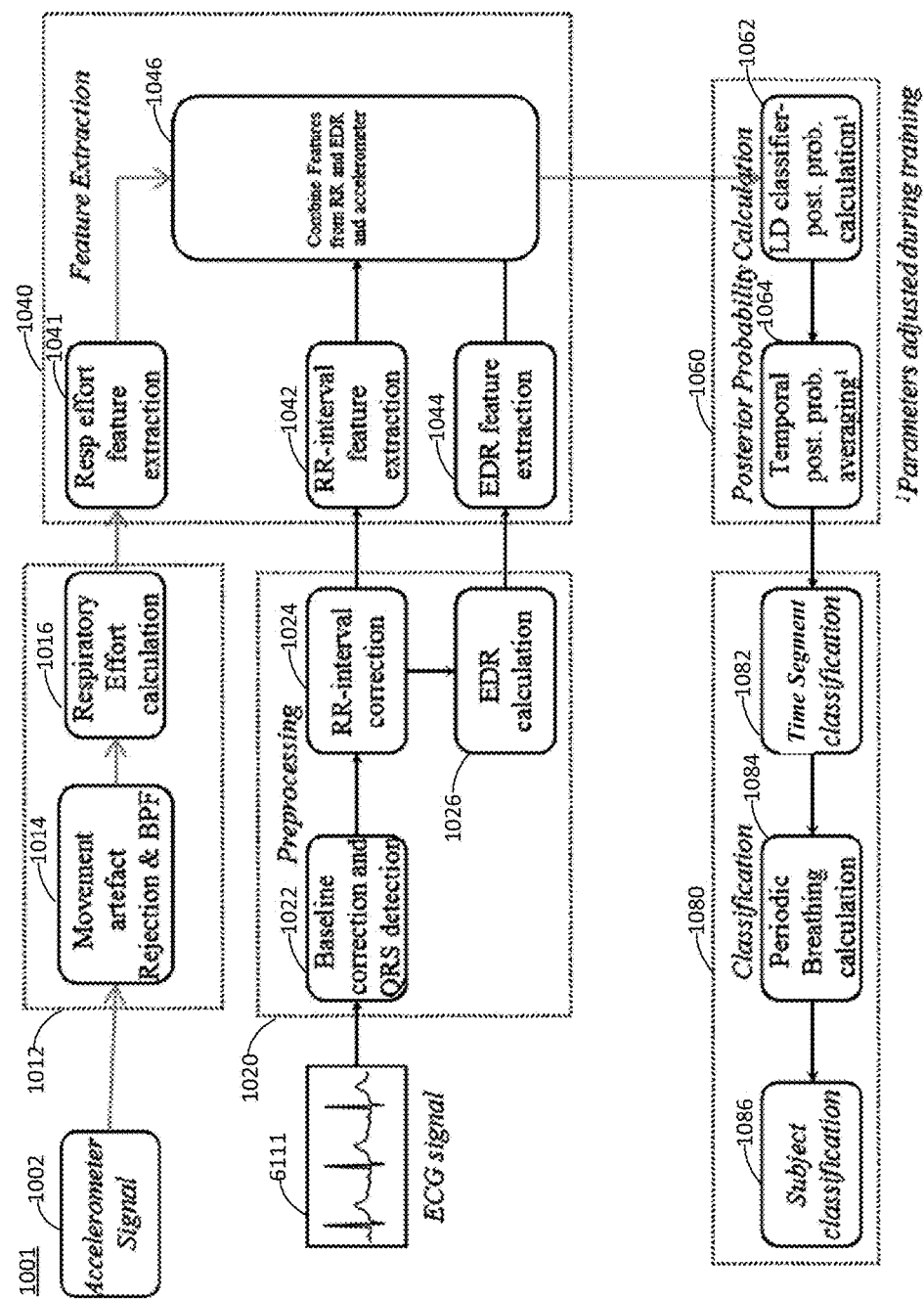

FIG. 10 shows a block diagram of another system configured to detect periodic breathing based on an ECG signal and an accelerometer signal.

Figure 11:
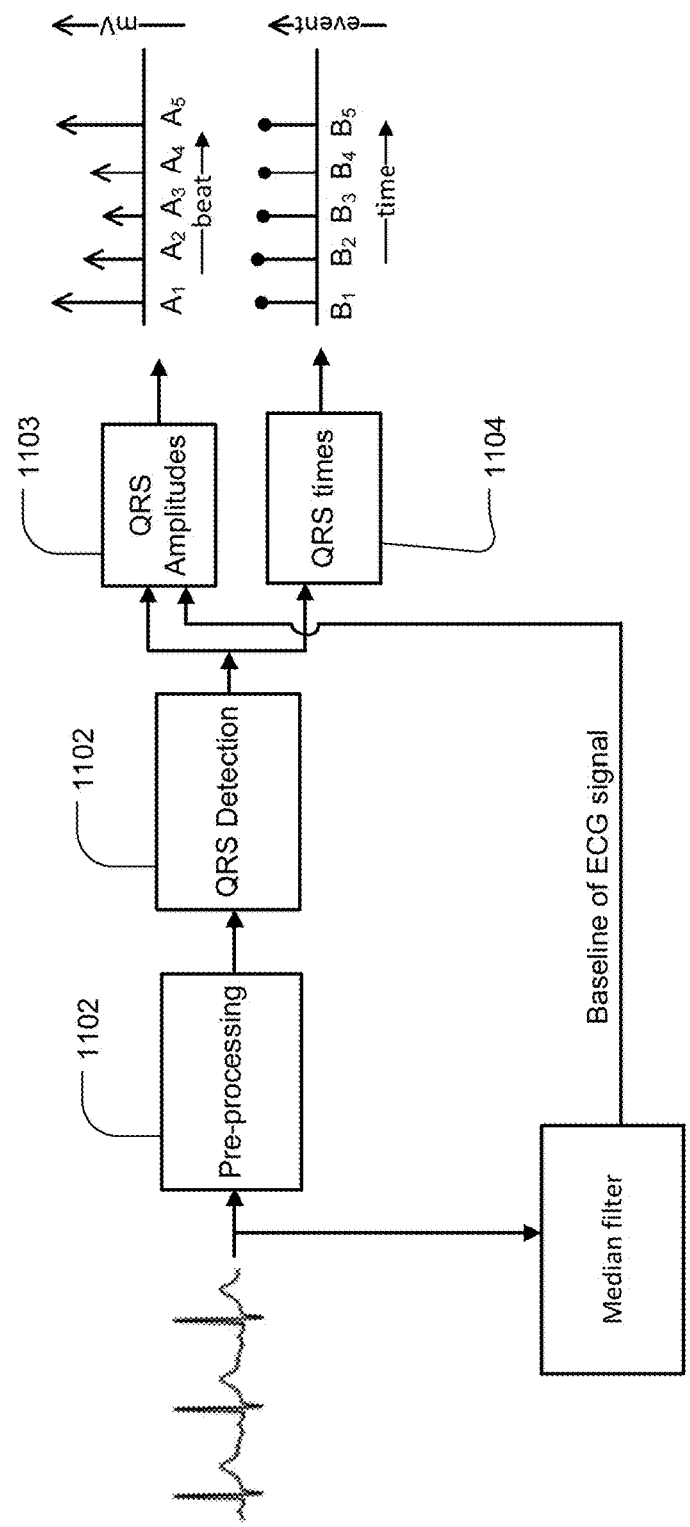

FIG. 11 also illustrates a high level schematic with example processing that may be implemented in some versions that obtain QRS amplitudes and timings.

Figure 12:
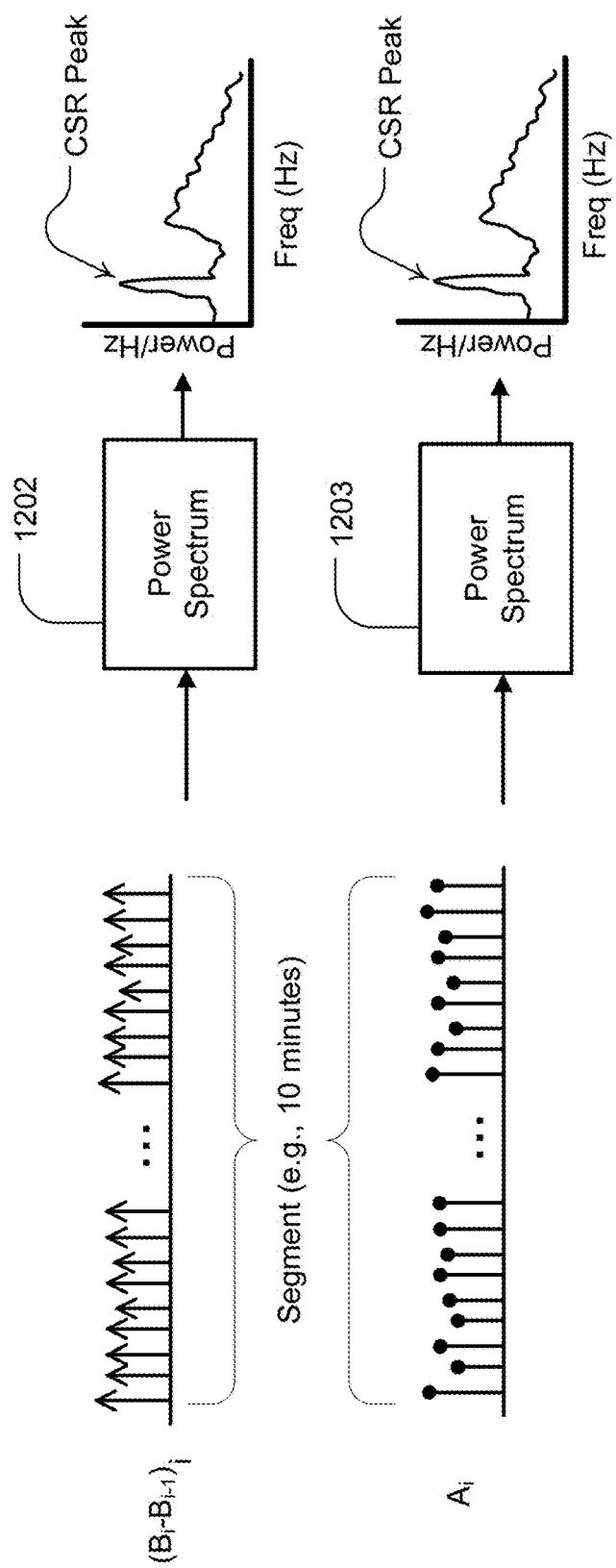

FIG. 12 illustrates processing that may be applied to a sequence of QRS amplitude values, and/or a sequence of the RR values. In an example, the sequences A, and B, may be assigned into segments (e.g., 10 minutes). A power spectral density estimate is then applied to each sequence. The power spectral density estimate may have a peak at very low frequencies (e.g., 0.01 to 0.02 Hz). By comparison with a threshold value, it can be implemented to determine whether CSR is present in that sequence.

Figure 13:
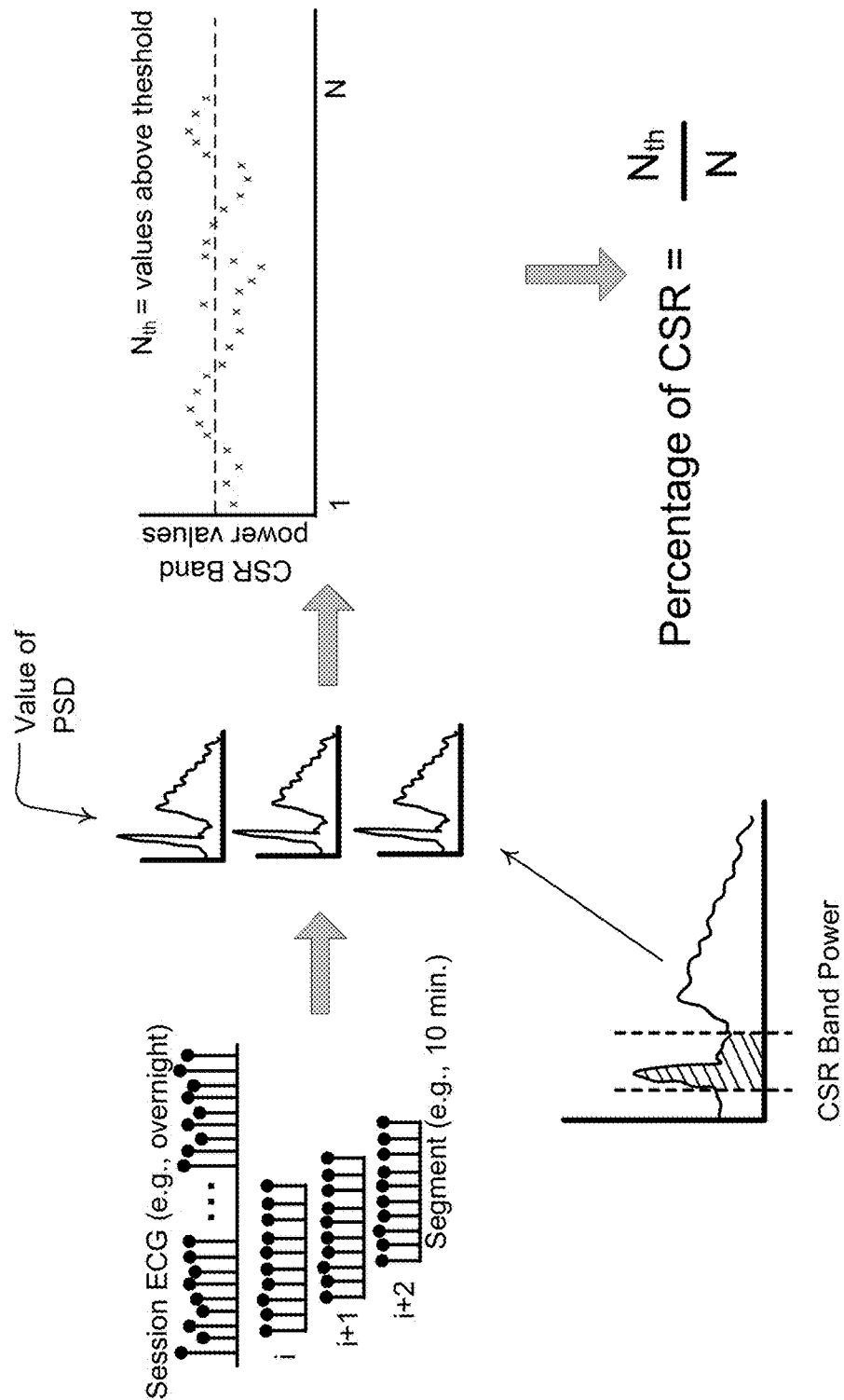

FIG. 13 illustrates processing by which a detection period of ECG data (e.g., a night's sleep session) may be parsed into a set of shorter segments. A power spectral density estimate can be formed for each segment, and the power within a frequency band likely to be associated with CSR may be calculated. These values can then be created for each segment over the time course of the complete ECG recording. The number of values above a certain fixed threshold may then be counted. An overall percentage of segments with evidence of CSR can be reported, for example, based on the count and the total number of segments.

Figure 14A:
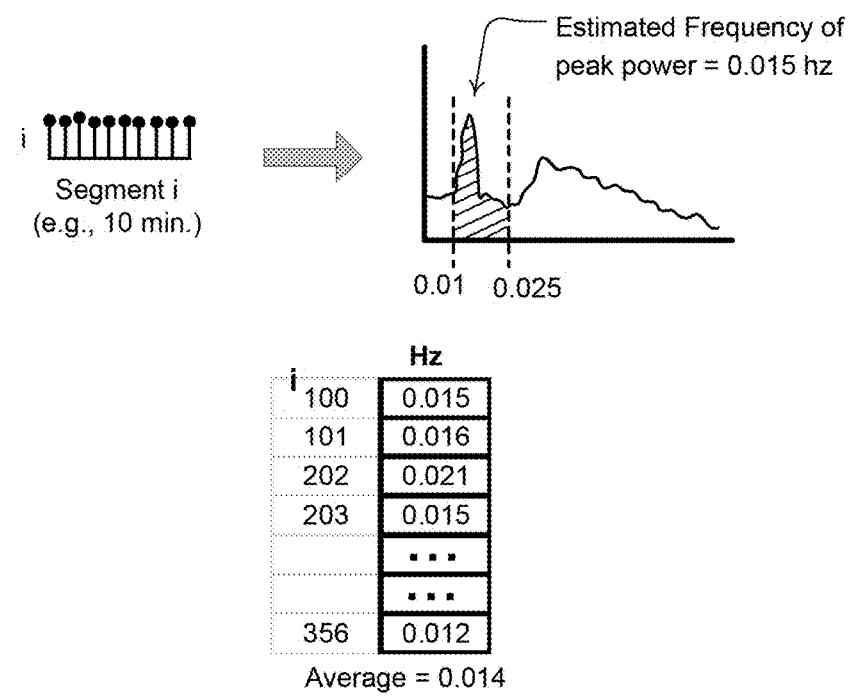
Figure 14B:
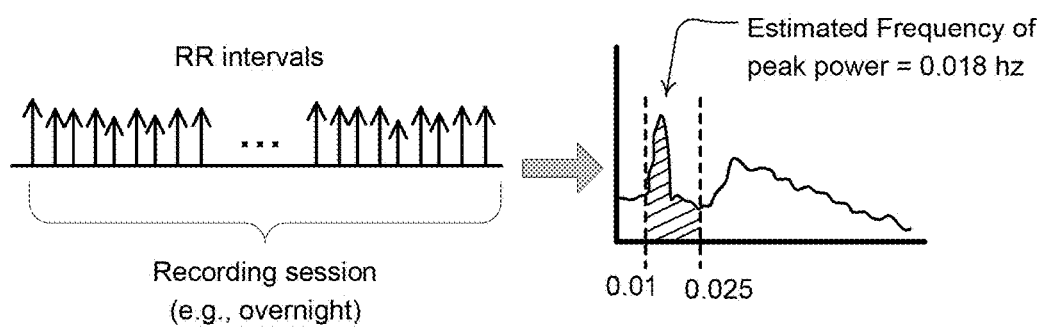

FIGS. 14A and 14B illustrate processing by which the cycle length of the Cheyne-Stokes respiration can be estimated. In FIG. 14A, a process calculates an estimate of the CSR frequency on a per segment basis, and then combines the segment estimates to form an overall value. In FIG. 14B the spectral density estimate of the more complete detection session (e.g., overnight) ECG signal is calculated, rather than in discrete segments, and the frequency at which the spectral power is maximum is used as the estimate of the CSR frequency.

4. DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

4.1 Therapy

In one form, the respective technology comprises a method for treating a respiratory disorder comprising the step of applying positive pressure to the entrance of the airways of a patient 1000.

In certain embodiments of the respective technology, a supply of air at positive pressure is provided to the nasal passages of the patient via one or both nares.

In certain embodiments of the respective technology, mouth breathing is limited, restricted or prevented.

4.2 Treatment Systems

In one form, the respective technology comprises an apparatus or device for treating a respiratory disorder. The apparatus or device may comprise a RPT device 4000 for supplying pressurised respiratory gas, such as air, to the patient 1000 via an air circuit 4170 to a patient interface 3000.

4.3 Patient Interface 3000

A non-invasive patient interface 3000 in accordance with one aspect of the respective technology comprises the following functional aspects: a seal-forming structure 3100, a plenum chamber 3200, a positioning and stabilising structure 3300 and one form of connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

4.3.1 Seal-Forming Structure 3100

In one form of the respective technology, a seal-forming structure 3100 provides a seal-forming surface, and may additionally provide a cushioning function.

A seal-forming structure 3100 in accordance with the respective technology may be constructed from a soft, flexible, resilient material such as silicone.

In one form, the seal-forming structure 3100 comprises a sealing flange 3110 and a support flange 3120. Preferably the sealing flange 3110 comprises a relatively thin member with a thickness of less than about 1 mm, for example about 0.25 mm to about 0.45 mm, that extends around the perimeter 3210 of the plenum chamber 3200. Support flange 3120 may be relatively thicker than the sealing flange 3110. The support flange 3120 is disposed between the sealing flange 3110 and the marginal edge 3220 of the plenum chamber 3200, and extends at least part of the way around the perimeter 3210. The support flange 3120 is or includes a spring-like element and functions to support the sealing flange 3110 from buckling in use. In use the sealing flange 3110 can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the respective technology include: a frusto-cone, at least a portion of which forms a seal on an underside of the patient's nose; a stalk, a flexible region on the underside of the frusto-cone and connecting the frusto-cone to the stalk. In addition, the structure to which the nasal pillow of the respective technology is connected includes a flexible region adjacent the base of the stalk. The flexible regions can act in concert to facilitate a universal joint structure that is accommodating of relative movement—both displacement and angular—of the frusto-cone and the structure to which the nasal pillow is connected. For example, the frusto-cone may be axially displaced towards the structure to which the stalk is connected.

In one form the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

4.3.2 Plenum Chamber 3200

Preferably the plenum chamber 3200 has a perimeter 3210 that is shaped to be complementary to the surface contour of the face of an average person in the region where a seal will form in use. In use, a marginal edge 3220 of the plenum chamber 3200 is positioned in close proximity to an adjacent surface of the face. Actual contact with the face is provided by the seal-forming structure 3100. Preferably the seal-forming structure 3100 extends in use about the entire perimeter 3210 of the plenum chamber 3200.

4.3.3 Positioning and Stabilising Structure 3300

Preferably the seal-forming structure 3100 of the patient interface 3000 of the respective technology is held in sealing position in use by the positioning and stabilising structure 3300.

4.3.4 Vent 3400

In one form, the patient interface 3000 includes a vent 3400 constructed and arranged to allow for the washout of exhaled carbon dioxide.

One form of vent 3400 in accordance with the respective technology comprises a plurality of holes, for example, about 20 to about 80 holes, or about 40 to about 60 holes, or about 45 to about 55 holes.

Preferably the vent 3400 is located in the plenum chamber 3200. Alternatively, the vent 3400 is located in a decoupling structure 3500, e.g. a swivel 3510.

4.3.5 Decoupling Structure(s) 3500

In one form the patient interface 3000 includes at least one decoupling structure 3500, for example a swivel 3510 or a ball and socket 3520.

4.3.6 Connection Port 3600

Connection port 3600 allows for connection to the air circuit 4170.

4.3.7 Forehead Support 3700

In one form, the patient interface 3000 includes a forehead support 3700.

4.3.8 Anti-Asphyxia Valve 3800

In one form, the patient interface 3000 includes an anti-asphyxia valve 3800.

4.3.9 Ports 3900

In one form of the respective technology, a patient interface 3000 includes one or more ports, that allow access to the volume within the plenum chamber 3200. In one form this allows a clinician to supply supplemental oxygen. In one form this allows for the direct measurement of a property of gases within the plenum chamber 3200, such as the pressure.

4.4 RPT Device 4000

A preferred RPT device 4000 in accordance with one aspect of the respective technology comprises mechanical and pneumatic components 4100, electrical components 4200 and is configured to execute one or more algorithms 4300. The RPT device preferably has an external housing 4010, preferably formed in two parts, an upper portion 4012 and a lower portion 4014. Furthermore, the external housing 4010 may include one or more panel(s) 4015. Preferably the RPT device 4000 comprises a chassis 4016 that supports one or more internal components of the RPT device 4000. The RPT device 4000 may include a handle 4018.

The pneumatic path of the RPT device 4000 preferably comprises one or more air path items, e.g. an inlet air filter 4112, an inlet muffler 4122, a pressure generator 4140 capable of supplying air at positive pressure (preferably a blower 4142), an outlet muffler 4124 and one or more transducers 4270, such as pressure transducer 4272 and flow transducer 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 preferably has an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

4.4.1 RPT Device Mechanical & Pneumatic Components 4100

An RPT device may comprise one or more of the following components in an integral unit. In an alternative form, one or more of the following components may be located as respective separate units.

4.4.1.1 Air Filter(s) 4110

A RPT device in accordance with one form of the respective technology may include an air filter 4110, or a plurality of air filters 4110.

In one form, an inlet air filter 4112 is located at the beginning of the pneumatic path upstream of a pressure generator 4140. See FIG. 4b.

In one form, an outlet air filter 4114, for example an antibacterial filter, is located between an outlet of the pneumatic block 4020 and a patient interface 3000. See FIG. 4b.

4.4.1.2 Muffler(s) 4120

In one form of the respective technology, an inlet muffler 4122 is located in the pneumatic path upstream of a pressure generator 4140. See FIG. 4b.

In one form of the respective technology, an outlet muffler 4124 is located in the pneumatic path between the pressure generator 4140 and a patient interface 3000. See FIG. 4b.

4.4.1.3 Pressure Generator 4140

In one form of the respective technology, a pressure generator 4140 for producing a flow, or a supply, of air at positive pressure is a controllable blower 4142. For example the blower 4142 may include a brushless DC motor 4144 with one or more impellers housed in a volute. The blower may be preferably capable of delivering a supply of air, for example at a rate of up to about 120 liters/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein in their entirety: U.S. Pat. No. 7,866,944; U.S. Pat. No. 8,638,014; U.S. Pat. No. 8,636,479; and PCT patent application publication number WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

4.4.1.4 Transducer(s) 4270

Transducers may be internal of the RPT device, or external of the RPT device. External transducers may be located for example on or form part of the air circuit, e.g. the patient interface. External transducers may be in the form of non-contact sensors such as a Doppler radar movement sensor that transmit or transfer data to the RPT device.

In one form of the respective technology, one or more transducers 4270 are located upstream and/or downstream of the pressure generator 4140. The one or more transducers 4270 may be constructed and arranged to measure properties such as a flow rate, a pressure or a temperature at that point in the pneumatic path.

In one form of the respective technology, one or more transducers 4270 may be located proximate to the patient interface 3000.

In one form, a signal from a transducer 4270 may be filtered, such as by low-pass, high-pass or band-pass filtering.

4.4.1.4.1 Flow Transducer 4274

A flow transducer 4274 in accordance with the respective technology may be based on a differential pressure transducer, for example, an SDP600 Series differential pressure transducer from SENSIRION.

In one form, a signal representing a flow rate such as a total flow Qt from the flow transducer 4274 is received by the central controller 4230.

4.4.1.4.2 Pressure Transducer 4272

A pressure transducer 4272 in accordance with the respective technology is located in fluid communication with the pneumatic path. An example of a suitable pressure transducer is a sensor from the HONEYWELL ASDX series. An alternative suitable pressure transducer is a sensor from the NPA Series from GENERAL ELECTRIC.

In one form, a signal from the pressure transducer 4272 is received by the central controller 4230.

4.4.1.4.3 Motor Speed Transducer 4276

In one form of the respective technology a motor speed transducer 4276 is used to determine a rotational velocity of the motor 4144 and/or the blower 4142. A motor speed signal from the motor speed transducer 4276 is preferably provided to the therapy device controller 4240. The motor speed transducer 4276 may, for example, be a speed sensor, such as a Hall effect sensor.

4.4.1.5 Anti-Spill Back Valve 4160

In one form of the respective technology, an anti-spill back valve is located between the humidifier 5000 and the pneumatic block 4020. The anti-spill back valve is constructed and arranged to reduce the risk that water will flow upstream from the humidifier 5000, for example to the motor 4144.

4.4.1.6 Air Circuit 4170

An air circuit 4170 in accordance with an aspect of the respective technology is a conduit or a tube constructed and arranged in use to allow a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

4.4.1.7 Oxygen Delivery 4180

In one form of the respective technology, supplemental oxygen 4180 is delivered to one or more points in the pneumatic path, such as upstream of the pneumatic block 4020, to the air circuit 4170 and/or to the patient interface 3000.

4.4.2 RPT Device Electrical Components 4200

4.4.2.1 Power Supply 4210

A power supply 4210 may be located internal or external of the external housing 4010 of the RPT device 4000.

In one form of the respective technology power supply 4210 provides electrical power to the RPT device 4000 only. In another form of the respective technology, power supply 4210 provides electrical power to both RPT device 4000 and humidifier 5000.

4.4.2.2 Input Devices 4220

In one form of the respective technology, a RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

4.4.2.3 Central Controller 4230

In one form of the respective technology, the central controller 4230 is one or a plurality of processors suitable to control a RPT device 4000.

Suitable processors may include an x86 INTEL processor, a processor based on ARM Cortex-M processor from ARM Holdings such as an STM32 series microcontroller from ST MICROELECTRONIC. In certain alternative forms of the respective technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the respective technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, and one or more input devices 4220.

The central controller 4230 may be configured to provide output signal(s) to one or more of an output device 4290, a therapy device controller 4240, a data communication interface 4280 and humidifier controller 5250.

In some forms of the respective technology, the central controller 4230 is configured to implement the one or more methodologies described herein, such as the one or more algorithms 4300 expressed as computer programs stored in a non-transitory computer readable storage medium, such as memory 4260. In some forms of the respective technology, the central controller 4230 may be integrated with a RPT device 4000. However, in some forms of the respective technology, some methodologies may be performed by a remotely located device. For example, the remotely located device may determine control settings for a ventilator or detect respiratory related events by analysis of stored data such as from any of the sensors described herein.

4.4.2.4 Clock 4232

Preferably RPT device 4000 includes a clock 4232 that is connected to the central controller 4230.

4.4.2.5 Therapy Device Controller 4240

In one form of the respective technology, therapy device controller 4240 is a control module 4330 that forms part of the algorithms 4300 executed by the central controller 4230.

In one form of the respective technology, therapy device controller 4240 is a dedicated motor control integrated circuit. For example, in one form a MC33035 brushless DC motor controller, manufactured by ONSEMI is used.

4.4.2.6 Protection Circuits 4250

The one or more protection circuits 4250 in accordance with the respective technology may comprise an electrical protection circuit, a temperature and/or pressure safety circuit.

4.4.2.7 Memory 4260

In accordance with one form of the respective technology the RPT device 4000 includes memory 4260, preferably non-volatile memory. In some forms, memory 4260 may include battery powered static RAM. In some forms, memory 4260 may include volatile RAM.

Preferably memory 4260 is located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the respective technology, the memory 4260 acts as a non-transitory computer readable storage medium on which are stored computer program instructions expressing the one or more methodologies described herein, such as the one or more algorithms 4300.

4.4.2.8 Data Communication Systems

In one preferred form of the respective technology, a data communication interface 4280 is provided, and is connected to the central controller 4230. Data communication interface 4280 is preferably connectable to remote external communication network 4282 and/or a local external communication network 4284. Preferably remote external communication network 4282 is connectable to remote external device 4286. Preferably local external communication network 4284 is connectable to local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

4.4.2.9 Output Devices Including Optional Display, Alarms

An output device 4290 in accordance with the respective technology may take the form of one or more of a visual, audio and haptic unit. A visual display may be a Liquid Crystal Display (LCD) or Light Emitting Diode (LED) display.

4.4.2.9.1 Display Driver 4292

A display driver 4292 receives as an input the characters, symbols, or images intended for display on the display 4294, and converts them to commands that cause the display 4294 to display those characters, symbols, or images.

4.4.2.9.2 Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

4.4.3 RPT Device Algorithms 4300

4.4.3.1 Pre-Processing Module 4310

A pre-processing module 4310 in accordance with one form of the respective technology receives as an input a signal from a transducer 4270, for example a flow transducer 4274 or pressure transducer 4272, and performs one or more process steps to calculate one or more output values that will be used as an input to another module, for example a therapy engine module 4320.

In one form of the respective technology, the output values include the interface or mask pressure Pm, the respiratory flow Qr, and the unintentional leak flow Ql.

In various forms of the respective technology, the pre-processing module 4310 comprises one or more of the following algorithms: pressure compensation 4312, vent flow 4314 (e.g. intentional leak), leak flow 4316 (e.g. unintentional leak), and respiratory flow 4318.

4.4.3.1.1 Pressure Compensation 4312

In one form of the respective technology, a pressure compensation algorithm 4312 receives as an input a signal indicative of the pressure in the pneumatic path proximal to an outlet of the pneumatic block. The pressure compensation algorithm 4312 estimates the pressure drop through the air circuit 4170 and provides as an output an estimated pressure, Pm, in the patient interface 3000.

4.4.3.1.2 Vent Flow 4314

In one form of the respective technology, a vent flow calculation algorithm 4314 receives as an input an estimated pressure, Pm, in the patient interface 3000 and estimates a vent flow of air, Qv, from a vent 3400 in a patient interface 3000.

4.4.3.1.3 Leak Flow 4316

In one form of the respective technology, a leak flow algorithm 4316 receives as an input a total flow, Qt, and a vent flow Qv, and provides as an output an estimate of the unintentional leak, i.e. leak flow, Ql, by calculating an average of the difference between total flow Qt and vent flow Qv over a period sufficiently long to include several breathing cycles, e.g. about 10 seconds.

In one form, the leak flow algorithm 4316 receives as an input a total flow Qt, a vent flow Qv, and an estimated pressure, Pm, in the patient interface 3000, and provides as an output a leak flow Ql, by calculating a leak conductance, and determining a leak flow Ql to be a function of leak conductance and pressure, Pm. Preferably leak conductance is calculated as the quotient of low pass filtered non-vent flow equal to the difference between total flow Qt and vent flow Qv, and low pass filtered square root of pressure Pm, where the low pass filter time constant has a value sufficiently long to include several breathing cycles, e.g. about 10 seconds.

4.4.3.1.4 Respiratory Flow 4318

In one form of the respective technology, a respiratory flow algorithm 4318 receives as an input a total flow, Qt, a vent flow, Qv, and a leak flow, Ql, and estimates a respiratory flow of air, Qr, to the patient, by subtracting the vent flow Qv and the leak flow Ql from the total flow Qt.

4.4.3.2 Therapy Engine Module 4320

In one form of the respective technology, a therapy engine module 4320 receives as inputs one or more of a pressure, Pm, in a patient interface 3000, and a respiratory flow of air to a patient, Qr, and provides as an output, one or more therapy parameters.

In one form of the respective technology, a therapy parameter is a CPAP treatment pressure Pt.

In one form of the respective technology, therapy parameters are one or more of a level of pressure support, and a target ventilation.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, and therapy parameter determination 4328.

4.4.3.2.1 Phase Determination 4321

In one form of the respective technology, the RPT device 4000 does not determine phase.

In one form of the respective technology, a phase determination algorithm 4321 receives as an input a signal indicative of respiratory flow, Qr, and provides as an output a phase $\Phi$ of a breathing cycle of a patient 1000.

In one form, the phase output is a discrete variable with values of either inhalation or exhalation. In one implementation of this form, the phase $\Phi$ is determined to have a discrete value of inhalation when a respiratory flow Qr has a positive value that exceeds a positive threshold, and the phase $\Phi$ is determined to have a discrete value of exhalation when a respiratory flow Qr has a value that is more negative than a negative threshold. By convention in this implementation, the phase value during inhalation may be set to 0, while the phase value during inhalation may be set to 1.

In one form, the phase output is a discrete variable with values of one of inhalation, mid-inspiratory pause, and exhalation.

In one form, the phase output is a continuous variable, for example varying from 0 to 1, or 0 to $2\pi$ radians.

4.4.3.2.2 Waveform Determination 4322

In one form of the respective technology, the therapy engine module 4320 provides an approximately constant treatment pressure throughout a respiratory cycle of a patient.

In one form of the respective technology, the therapy engine module 4320 provides a treatment pressure that varies over the respiratory cycle according to a waveform of pressure vs phase.

In one form of the respective technology, a waveform determination algorithm 4322 provides as an output the pressure-phase waveform $P(\Phi)$. The pressure-phase waveform $P(\Phi)$ is preferably valued between 0 and 1.

The predetermined waveform $P(\Phi)$ may be provided as a lookup table of values P as a function of phase values $\Phi$. The predetermined waveform $P(\Phi)$ may alternatively be provided as one or more parameters that characterise the waveform $P(\Phi)$ according to a predetermined parametric description.

In one form, the waveform is maintained at an approximately constant level for all values of phase.

In one form, the waveform is a square wave, having a constant higher value for some values of phase, and a constant lower level for other values of phase. In this form, the returned parameter may be a threshold value of phase above which the waveform rises from the lower level to the higher level.

In one form, the waveform $P(\Phi)$ has two exponential portions, an exponential rise according to one time constant for values of phase up to a threshold, and an exponential decay for values of phase above the threshold. In this form, the returned parameters may be the two time constants and the threshold.

4.4.3.2.3 Ventilation Determination 4323

In one form of the respective technology, a ventilation determination algorithm 4323 receives an input a respiratory flow Qr, and determines a measure indicative of patient ventilation, Vent.

In one form ventilation determination algorithm 4323 determines a current value of patient ventilation, Vent, as half the low-pass filtered absolute value of respiratory flow, Qr.

4.4.3.2.4 Determination of Inspiratory Flow Limitation 4324

In one form of the respective technology, the central controller 4230 executes one or more algorithms 4324 for the detection of inspiratory flow limitation.

In one form the algorithm 4324 receives as an input a respiratory flow signal Qr and provides as an output a metric of the extent to which the inspiratory portion of the breath exhibits inspiratory flow limitation.

In one form of the respective technology, the inspiratory portion of each breath is identified by a zero-crossing detector. A number of evenly spaced points (for example, sixty-five), representing points in time, are interpolated by an interpolator along the inspiratory flow-time curve for each breath. The curve described by the points is then scaled by a scaler to have unity length (duration/period) and unity area to remove the effects of changing respiratory rate and depth. The scaled breaths are then compared in a comparator with a pre-stored template representing a normal unobstructed breath, similar to the inspiratory portion of the breath shown in FIG. 6a. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by the central controller 4230 for the preceding several inspiratory events. This is repeated over the same inspiratory events for the second such point, and so on. Thus, for example, sixty five scaled data points are generated by the central controller 4230, and represent a moving average of the preceding several inspiratory events, e.g. three events. The moving average of continuously updated values of the (e.g. sixty five) points are hereinafter called the "scaled flow", designated as Qs(t). Alternatively, a single inspiratory event can be utilised rather than a moving average.

From the scaled flow, two shape factors relating to the determination of partial obstruction may be calculated.

Shape factor 1 is the ratio of the mean of the middle (e.g. thirty-two) scaled flow points to the mean overall (e.g. sixty-five) scaled flow points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical user.

Shape factor 2 is calculated as the RMS deviation from unit scaled flow, taken over the middle (e.g. thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the respective technology, the number of sampled points, breaths and middle points may differ from those described above. Furthermore, the threshold values can other than those described.

4.4.3.2.5 Determination of Apneas and Hypopneas 4325

In one form of the respective technology, the central controller 4230 executes one or more algorithms 4325 for the determination of the presence of apneas and/or hypopneas.

Preferably the one or more algorithms 4325 receive as an input a respiratory flow signal Qr and provide as an output a flag that indicates that an apnea or a hypopnea has been detected.

In one form, an apnea will be said to have been detected when a function of respiratory flow Qr falls below a flow threshold for a predetermined period of time. The function may determine a peak flow, a relatively short-term mean flow, or a flow intermediate of relatively short-term mean and peak flow, for example an RMS flow. The flow threshold may be a relatively long-term measure of flow.

In one form, a hypopnea will be said to have been detected when a function of respiratory flow Qr falls below a second flow threshold for a predetermined period of time. The function may determine a peak flow, a relatively short-term mean flow, or a flow intermediate of relatively short-term mean and peak flow, for example an RMS flow. The second flow threshold may be a relatively long-term measure of flow. The second flow threshold is greater than the flow threshold used to detect apneas.

4.4.3.2.6 Determination of Snore 4326

In one form of the respective technology, the central controller 4230 executes one or more snore algorithms 4326 for the detection of snore.

In one form the snore algorithm 4326 receives as an input a respiratory flow signal Qr and provides as an output a metric of the extent to which snoring is present.

Preferably the algorithm 4326 comprises the step of determining the intensity of the flow signal in the range of 30-300 Hz. Further preferably, algorithm 4326 comprises a step of filtering the respiratory flow signal Qr to reduce background noise, e.g. the sound of airflow in the system from the blower.

4.4.3.2.7 Determination of Airway Patency 4327

In one form of the respective technology, the central controller 4230 executes one or more algorithms 4327 for the determination of airway patency.

In one form, airway patency algorithm 4327 receives as an input a respiratory flow signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 $cmH_2O$.

In one form, airway patency algorithm 4327 receives as an input a respiratory flow signal Qr, and determines the presence or absence of a cardiogenic signal. The absence of a cardiogenic signal is taken to be an indication of a closed airway.

4.4.3.2.8 Determination of Therapy Parameters 4328

In one form of the respective technology, the central controller 4230 executes one or more algorithms 4328 for the determination of one or more therapy parameters using the values returned by one or more of the other algorithms in the therapy engine module 4320.

In one form of the respective technology, the therapy parameter is an instantaneous treatment pressure Pt. In one implementation of this form, the treatment pressure Pt is given by $$Pt = AP(\Phi) + P_0 \qquad (1)$$

where:
A is the pressure support,
P ($\Phi$) is the pressure-phase waveform value (in the range 0 to 1) at the current value $\Phi$ of phase, and
$P_0$ is a base pressure.

Various therapy modes may be defined depending on the values of the parameters A and $P_0$. In some implementations of this form of the respective technology, the pressure support A is identically zero, so the treatment pressure Pt is identically equal to the base pressure $P_0$ throughout the respiratory cycle. Such implementations are generally grouped under the heading of CPAP therapy.

The base pressure $P_0$ may be a constant value that is prescribed and/or manually entered to the PAP device 4000. This alternative is sometimes referred to as constant CPAP therapy. Alternatively, the base pressure $P_0$ may be continuously computed as a function of indices or measures of one or more of sleep disordered breathing events such as flow limitation, apnea, hypopnea, patency, and snore returned by the respective algorithms in the therapy engine module 4320. This alternative is sometimes referred to as APAP therapy.

In other implementations of this form, referred to as positive-pressure ventilation, the pressure support A is non-zero. In some such implementations, in which the RPT device 4000 acts as a servo-ventilator, the therapy parameter determination algorithm 4328 takes as input the current measure Vent of ventilation and a target ventilation value Vtgt and calculates a value of pressure support A to bring the current measure Vent of ventilation towards the target value Vtgt of ventilation. In such implementations, the pressure-phase waveform P ($\Phi$) is configured so as to attain a higher value during the inspiration portion of the respiratory cycle, and a lower value during the expiration portion of the respiratory cycle.

In such implementations, the therapy parameter determination algorithm 4328 may apply a continuous control methodology to compute the pressure support A. One such continuous control methodology is Proportional-Integral (PI) control, according to which the pressure support is computed as:

$$A = G \int (Vent - Vtgt) dt \quad (2)$$

where G is the gain of the PI control.

Other continuous control methodologies that may be applied by the therapy parameter determination algorithm 4328 include proportional (P), proportional-differential (PD), and proportional-integral-differential (PID).

Other control methodologies, referred to as discrete control methodologies, return a pressure support A that is one of a discrete set of predetermined values.

FIG. 4E is a flow chart illustrating a method 4500 carried out by the central controller 4230 as one implementation of the algorithm 4328. The method 4500 starts at step 4520, at which the central controller 4230 compares the measure of the presence of apnea/hypopnea with a first threshold, and determines whether the measure of the presence of apnea/hypopnea has exceeded the first threshold for a predetermined period of time, indicating an apnea/hypopnea is occurring. If so, the method 4500 proceeds to step 4540; otherwise, the method 4500 proceeds to step 4530. At step 4540, the central controller 4230 compares the measure of airway patency with a second threshold. If the measure of airway patency exceeds the second threshold, indicating the airway is patent, the detected apnea/hypopnea is deemed central, and the method 4500 proceeds to step 4560; otherwise, the apnea/hypopnea is deemed obstructive, and the method 4500 proceeds to step 4550.

At step 4530, the central controller 4230 compares the measure of flow limitation with a third threshold. If the measure of flow limitation exceeds the third threshold, indicating inspiratory flow is limited, the method 4500 proceeds to step 4550; otherwise, the method 4500 proceeds to step 4560.

At step 4550, the central controller 4230 increases the treatment pressure Pt by a predetermined pressure increment ΔP, provided the increased treatment pressure Pt would not exceed an upper limit Pmax. In one implementation, the predetermined pressure increment ΔP and upper limit Pmax are 1 cmH$_2$O and 20 cmH$_2$O respectively. The method 4500 then returns to step 4520.

At step 4560, the central controller 4230 decreases the treatment pressure Pt by a decrement, provided the decreased treatment pressure Pt would not fall below a lower limit Pmin. The method 4500 then returns to step 4520. In one implementation, the decrement is proportional to the value of Pt−Pmin, so that the decrease in Pt to the lower limit Pmin in the absence of any detected events is exponential. In one implementation, the constant of proportionality is set such that the time constant τ of the exponential decrease of Pt is 60 minutes, and the lower limit Pmin is 4 cmH$_2$O. In other implementations, the time constant τ could be as low as 1 minute and as high as 300 minutes, or as low as 5 minutes and as high as 180 minutes. Alternatively, the decrement in Pt could be predetermined, so the decrease in Pt to the lower limit Pmin in the absence of any detected events is linear.

4.4.3.3 Control Module 4330

Therapy control module 4330 in accordance with one aspect of the respective technology receives as inputs the therapy parameters from the therapy engine module 4320, and controls the pressure generator 4140 to deliver a flow of gas in accordance with the therapy parameters.

In one form of the respective technology, the therapy parameter is a treatment pressure Pt, and the therapy control module 4330 controls the therapy device 4245 to deliver a flow of gas whose mask pressure Pm at the patient interface 3000 is equal to the treatment pressure Pt.

4.4.3.4 Detection of Fault Conditions 4340

In one form of the respective technology, the central controller 4230 executes one or more methods for the detection of fault conditions. Preferably the fault conditions detected by the one or more methods includes at least one of the following:

Power failure (no power, or insufficient power)
Transducer fault detection
Failure to detect the presence of a component
Operating parameters outside recommended ranges (e.g. pressure, flow, temperature, PaO$_2$)
Failure of a test alarm to generate a detectable alarm signal.

Upon detection of the fault condition, the corresponding algorithm signals the presence of the fault by one or more of the following:

Initiation of an audible, visual &/or kinetic (e.g. vibrating) alarm
Sending a message to an external device
Logging of the incident 4.5 Humidifier 5000

4.5.1 Humidifier Overview

In one form of the respective technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5a and FIG. 5b, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

Breathing Waveforms 6000

FIG. 6A shows a model typical breath waveform of a person while sleeping. The horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

FIG. 6B shows a patient during Non-REM sleep breathing normally over a period of about ninety seconds, with about 34 breaths, being treated with Automatic PAP, and the mask pressure being about 11 cmH$_2$O. The top channel shows oximetry (SpO$_2$), the scale has a range of saturation from 90 to 99% in the vertical direction. The patient maintained a saturation of about 95% throughout the period shown. The second channel shows quantitative respiratory airflow, and the scale ranges from −1 to +1 LPS in a vertical direction, and with inspiration positive. Thoracic and abdominal movement are shown in the third and fourth channels.

FIG. 6C shows polysomnography of a patient before treatment. There are eleven signal channels from top to bottom with a 6 minute horizontal span. The top two channels are both EEG (electoencephalogram) from different scalp locations. Periodic spikes in the second EEG represent cortical arousal and related activity. The third channel down is submental EMG (electromyogram). Increasing activity around the time of arousals represents genioglossus recruitment. The fourth & fifth channels are EOG (electro-oculogram). The sixth channel is an electocardiogram. The seventh channel shows pulse oximetry ($SpO_2$) with repetitive desaturations to below 70% from about 90%. The eighth channel is respiratory airflow using nasal cannula connected to a differential pressure transducer. Repetitive apneas of 25 to 35 seconds alternate with 10 to 15 second bursts of recovery breathing coinciding with EEG arousal and increased EMG activity. The ninth channel shows movement of chest and the tenth shows movement of abdomen. The abdomen shows a crescendo of movement over the length of the apnea leading to the arousal. Both become untidy during the arousal due to gross body movement during recovery hyperpnea. The apneas are therefore obstructive, and the condition is severe. The lowest channel is posture, and in this example it does not show change.

FIG. 6D shows patient flow data where the patient is experiencing a series of total obstructive apneas. The duration of the recording is approximately 160 seconds. Flow ranges from about +1 L/s to about −1.5 L/s. Each apnea lasts approximately 10-15 s.

FIG. 6E shows a scaled inspiratory portion of a breath where the patient is experiencing low frequency inspiratory snore.

FIG. 6F shows a scaled inspiratory portion of a breath where the patient is experiencing an example of flattened inspiratory flow limitation.

FIG. 6G shows a scaled inspiratory portion of a breath where the patient is experiencing an example of "mesa" flattened inspiratory flow limitation.

FIG. 6H shows a scaled inspiratory portion of a breath where the patient is experiencing an example of "panda ears" inspiratory flow limitation.

FIG. 6I shows a scaled inspiratory portion of a breath where the patient is experiencing an example of "chair" inspiratory flow limitation.

FIG. 6J shows a scaled inspiratory portion of a breath where the patient is experiencing an example of "reverse chair" inspiratory flow limitation.

FIG. 6K shows a scaled inspiratory portion of a breath where the patient is experiencing an example of "M-shaped" inspiratory flow limitation.

FIG. 6L shows a scaled inspiratory portion of a breath where the patient is experiencing an example of severely "M-shaped" inspiratory flow limitation.

FIG. 6M shows patient data from a patient with Cheyne-Stokes respiration. There are three channels: oxygen saturation ($SpO_2$); a signal indicative of flow; and thoracic movement. The data span six minutes. The signal representative of flow was measured using a pressure sensor connected to nasal cannula. The patient exhibits apneas of about 22 seconds and hyperpneas of about 38 seconds. The higher frequency low amplitude oscillation during apnea is cardiogenic.

FIG. 6N shows patient data from a patient with another example of Cheyne-Stokes respiration, using the same three channels as in FIG. 6M. The data span ten minutes. The patient exhibits hyperpneas of about 30 seconds and hypopneas of about 30 seconds.

Cardiac Waveforms

FIG. 6O is an example of the typical electrical waveform associated with an electrocardiogram signal, and the various conventional labels associated with it. The exact shape of the QRS complex can vary depending on lead position; this diagram shows the typical shape for a Lead II configuration. The QRS amplitude is the amplitude of the signal above a nominal baseline. The RR interval is the time between sequential heart beats.

4.6 Detection of Periodic Breathing from Electrocardiogram

The present technology may include a device, apparatus, system, or the like configured to determine whether a patient suffers from periodic breathing. One example of periodic breathing may be CSR. To detect periodic breathing, such as with one or more processors, the present technology may analyze signals from one or more sensors such as an electrocardiogram (ECG) signal. In some instances, the present technology may analyze an accelerometer signal in conjunction with the ECG signal. The present technology may perform a time-domain and spectral-domain analysis of one or more signals. The present technology may identify one or more time segments of the ECG signal as periodic breathing time segments. The present technology may determine an overall likelihood of the patient having periodic breathing.

The device, apparatus or system according to the present technology may include integrated chips, a memory, control instruction, data and information storage medium. By way of example, integrated chips may have coded therein programmed instructions encompassing periodic breathing detection methodologies. Such instructions may also or alternatively be loaded as software or firmware using an appropriate data storage medium.

Methodologies for periodic breathing detection described herein may be implemented by one or more processors. For instance, a processor may be implemented with classifiers, thresholds, functions, or algorithms. The processor of the present technology may process data from an ECG signal and, in some instances, an accelerometer signal in conjunction with the ECG signal. By processing the ECG signal, and in some instances, by processing the ECG signal and the accelerometer signal, the processor may detect an instance of periodic breathing, and its probability as discussed in more detail herein. The processor(s) may make such a determination with stored data from previously recorded sensor signals and/or control a measurement and detection with data of the sensor signals in near real or real time. In some cases, the detection processor may be in a stand-alone device, such as a processor within a sensor patch described in more detail herein. In some cases, the processor may be a processor in a controller of an RPT apparatus, such as any of the RPT processors described herein. In some cases, the processor may be a programmed processor of a general purpose computer serving the specific purposes described herein upon receiving of sensor input (e.g., ECG data etc.).

For example, FIG. 7 illustrates a surface ECG patch 700 according to one aspect of the present technology. As illustrated in FIG. 7, the patch 700 may be well adhered to a patient's chest. The patch 700 may include one or more sensors or electrodes. For instance, the patch 700 may include a sensor configured to acquire a single lead of ECG. Alternatively, in addition to ECG, the patch 700 may contain an accelerometer configured to detect additional information, such as movement and/or a relative orientation of the patient, such as if the patient is in a supine position or a side position. In another embodiment, the patch 700 may also include an oximeter configured to acquire oximetry data. The patch 700 may detect a respiratory effort signal. The patch 700 may have a high sensitivity, for example, 0.01 g rating, In one embodiment, the patch 700 may have one or more processors implemented therein configured to detect periodic breathing based on one or more sensor measurements. In the alternative, the patch 700 may transmit one or more sensor measurements to a stand-alone monitoring device or a treatment device such as a flow generator controller for detection of periodic breathing. The patch 700 may communicate with these devices or processors via either a wire or wireless communications.

Example implementation details for detecting an instance of periodic breathing are described herein.

4.6.1 ECG Based Implementation

FIG. 8 illustrates an example implementation of a system 800 configured to detect periodic breathing based on an ECG signal and may optionally do so without an accelerometer signal. As shown in FIG. 8, the system 800 may include one or more of the following: an ECG input 810, an ECG preprocessing component 820, a feature extraction component 840, a posterior probability calculation component 860, and a classification component 880. Details with regard to each component are described herein.

4.6.1.1 ECG Input

The ECG input 810 may provide an input signal indicative of a surface ECG measurement of a patient. The surface ECG measurement may represent the patient's cardiac activity. The input 810 may include an ECG measurement device that measures ECG signals. For example, the input 810 may include a traditional Holter monitor, a 12-lead ECG device, or a patch-type ECG device such as the patch 700 of FIG. 7, among other possibilities. In some embodiments, the input 810 may include a device from which an ECG signal may be derived or accessed. For instance, the input 810 may be a pacemaker, a defibrillator, or a logging device that records ECG signals or other bio-potential signals from one or more electrodes, among other possibilities.

Thus, in some versions of the technology, an electrocardiogram may be taken from an invasive device that records an electrogram such as from one or more sensing leads (so called internal electrograms—IEGM). For example, an implanted device such as a pacemaker, cardiac resynchronization device (CRD), or implantable cardioverter defibrillator (ICD) may provide a suitable signal for the processing as described in more detail herein. In such cases, one or more lead wires of such a device may be used to provide electrical impulses from which QRS signals may be evaluated/processed.

Additionally, an ECG signal can be acquired using a surface-mounted ECG system. This could be a conventional Holter ECG system (e.g., the Spacelabs Lifescreen system), or more usefully, a wearable patch ECG system (such as the iRhythm Zio patch). A wearable adhesive ECG acquisition system has the convenience of comfort and simplicity for patients, and hence can be used to acquire signals over longer periods of time.

In such ECG acquisition systems, there can be two features of prime interest for measurement of CSR. Firstly, the typical ECG has several characteristics electrical deviations which have a conventional labelling system as illustrated in FIG. 7*b*. The P-wave is the depolarization of the atria which initiates the contraction of the heart. The main QRS complex is associated with the depolarization of the ventricles. The T-wave is associated with the repolarization of the heart to prepare for the next beat. Significant parameters to measure with an ECG are (a) the RR interval—this is the time between heart beats, and (b) the amplitude of the QRS complex. The RR interval gets shorter as the heart beats faster. The RR interval will also vary in particular patterns when a cardiac arrhythmia occurs.

According to one aspect of the disclosed technology, an ECG signal may be split into time segments. A time segment may be as long as the entire record of the ECG signal or as short as the length of a representative hypopnea-hyperpnoea sequence. Time segments may be of equal length. In one example, each time segment may have a time length of 30 minutes. In another example, each time segment may have a time length of 10 minutes.

4.6.1.2 ECG Preprocessing

The preprocessing component 820 may perform a series of pre-processing steps on the ECG signal provided by the input 810. As shown in FIG. 8, the preprocessing component 820 may include one or more of the following units: a baseline correction and QRS detection unit 822, an RR-interval correction unit 824, and an ECG-derived respiration (EDR) calculation unit 826.

The baseline correction and QRS detection unit 822 may filter the ECG signal to remove any unwanted noise. For example, the baseline correction and QRS detection unit 822 may remove from the ECG signal baseline problems, such as a baseline drift. To remove baseline problems, the unit 822 may implement a linear low-pass filter in analog or digital domain, or a digital median filter.

The unit 822 may detect one or more QRS points in the ECG signal. The unit 822 may extract QRS complex from the ECG signal. A QRS peak may correspond to a ventricular contraction associated with a heartbeat. The QRS peak may represent a fiducial point in a heartbeat. The unit 822 may implement any known techniques to detect QRS peaks. The unit 822 may yield a sequence of timestamps indicative of occurrences of QRS peaks detected in an ECG time segment. An example of such sequence may be [0.1 s, 1.2 s, 1.9 s, 2.8 s, 3.8 s].

With continued reference to FIG. 8, the RR-interval correction unit 824 may determine one or more RR intervals, namely, inter-beat intervals based on the QRS detection. An RR interval may be a time length between two consecutive QRS peaks. The unit 824 may generate a sequence of RR intervals based on the detection of QRS peaks. For instance, based on the QRS sequence example provided immediately above, the unit 824 may generate a sequence of RR intervals [1.1, 0.7, 0.9, 1]. By way of another example, if a patient has a heart rate of 60 beats/minute, an ECG time segment taken from the patient over a period of 10 minutes may have about a sequence of 600 RR intervals, such as RR [0.8, 0.9, 1.0, 0.9, 1.2, . . . 0.89, 0.9]. The sequence of RR intervals may be stored in a vector. The vector may be referred to as an RR-interval vector.

The EDR calculation unit 826 may calculate an ECG derived respiration signal. For example, respiration may have an impact on measured ECG. Information concerning respiration (e.g., thoracic movement, respiratory effort, periodic breathing, etc.) may be present, to a detectable degree depending on further processing, in the ECG data. Thus, by way of example, the unit 826 may determine a magnitude of each QRS detection point in an ECG time segment. Alternatively, the EDR calculation unit 826 may determine an integral of a small area of time around each QRS detection point. The magnitude or integral determined as such may be regarded as an EDR number. For an ECG time segment, the EDR calculation unit 826 may yield a sequence of EDR numbers, such as [200.2, 210.3, 220.1, 215.2, 208.9, . . . 234.1, 223.2]. The sequence of EDR numbers may be stored in a vector. The vector may be referred to as an EDR vector.

4.6.1.3 Feature Extraction

With continued reference to FIG. 8, the feature extraction component 840 may extract or derive one or more features from an ECG time segment. Each feature may act as a compressed representation of the ECG time segment. The feature extraction component 840 may include one or more of the following units: an RR-interval feature extraction unit 842, an EDR feature extraction unit 844, and a feature combiner unit 846.

As shown in FIG. 8, the RR-interval feature extraction unit 842 may receive the RR-interval vector generated by the RR-interval correction unit 824. The unit 842 may calculate a power spectral density estimate of the RR intervals. The unit 842 may perform a frequency domain analysis of the RR intervals to determine spectral variations due to periodic breathing. FIG. 9 illustrates a graph of a power spectral density of the RR intervals, where the y-axis represents the value of the power spectral density as a function of frequency. In general, an RR feature refers to a numerical value calculated by processing of the RR intervals in the time segment. Representative examples of such values might be the mean value of the RR intervals, the standard deviation of the RR intervals, the number of RR intervals which differ by more than 50 ms from the subsequent interval, etc.

With continued reference to FIG. 8, the EDR feature extraction unit 844 may receive the EDR vector generated by the EDR calculation unit 826. The EDR feature extraction unit 844 may calculate a power spectral density estimate of the EDR vector. In general, an EDR feature refers to a numerical value calculated by processing of the EDR intervals in the time segment. Representative examples of such values might be the mean value of the EDR signal, the standard deviation of the EDR signal, the autocorrelation of the EDR signal, etc.

The feature combiner unit 846 may combine the features extracted by the RR-interval feature extraction unit 842 and the EDR feature extraction unit 844. The unit 846 may group one or more features to form a pattern. The pattern may be manipulated with a suitable classifier algorithm to produce a probability for each possible class for which the ECG time segment may represent as illustrated in the calculation unit 862 (e.g., linear discriminant classifier).

4.6.1.4 Posterior Probability Calculation

With continued reference to FIG. 8, the posterior probability calculation component 860 may assign a probability of periodic breathing to each ECG time segment. The component 860 may produce a probability value between zero and one for each ECG time segment. The posterior probability may reflect an uncertainty of classifying an extracted feature as indicative of periodic breathing. For example, a posterior probability of 0.7 may be interpreted as meaning that the particular time segment has a 70% chance of coming from a time segment where the subject had periodic breathing.

The component 860 may be programmed to iterate through an entire length of an ECG signal, and calculate a probability value for each ECG time segment contained therein. The iteration may proceed until all ECG time segments have been processed. The component 860 may result in a vector of probability values, each corresponding to a respective ECG time segment. An overall probability of periodic breathing for an ECG signal may be set to a maximum probability found in all ECG time segments of the ECG signal.

As shown in FIG. 8, the component 860 may include a linear discriminant (LD) classifier-posterior probability calculation unit 862. The unit 862 may include parameters adjusted during training. These parameters are the weights associated with the influence of each individual feature on the overall classification. The features are assembled together in the feature combiner 846, before being passed into the classifier. In a linear classifier, the discriminant value is a linear combination of the features, i.e., the discriminant value will be $(a_1 x_1 + a_2 x_2 + \ldots + a_i x_i + \ldots a_N x_N)$ where $x_i$ is a feature, and $a_i$ are "weighting". parameters. For each feature extracted from an ECG time segment, the unit 862 may calculate a distance normal from the data point in the feature space to a decision boundary. The decision boundary is determined by a threshold value of the discriminant function implemented to characterize the ECG time segment for periodic breathing. A perpendicular distance may be mapped to a probability value where the probability value is a function of the distance from the decision boundary. If the distance is zero, the feature value would coincide with the boundary line, and the probability associated with the class membership is 0.5. As the distance increases to positive infinity, the probability may asymptotically approach towards to 1.0. As the distance increase to negative infinity, the probability may asymptotically approach towards 0.0. By defining the region feature space corresponding to periodic breathing as positive distance from the decision boundary, periodic breathing may be defined as any resulting probability value of greater than 0.5, or any other suitable value.

While we have described a linear discriminant classifier as one embodiment for 862, a number of classifier types are available including: a Bayesian classification system, Bayesian maximum likelihood linear and quadratic discriminants, neural networks, clustering methods, can be used in 862.

The component 860 may also include a temporal posterior probability averaging unit 864. The temporal posterior probability averaging unit takes the probabilities from nearby time segments and uses them to update the probability of the current time segment. For example, if the probability of a current time segment representing periodic breathing is 0.8, and the surrounding time segments have probability values of [0.3 0.3] (i.e., the sequence of time segment probabilities is [0.3 0.3 0.8 0.3 0.3] where 0.8 is the current time segment and the other values represent the probabilities of the preceding and following two time segments), then we could apply a weighing function of [0.05 0.05 0.8 0.05 0.05] to the probabilities and update the probability to 0.3×0.05+0.03×0.05+0.8×0.8+0.3×0.05+0.3×0.05=0.7. In this way, the estimate for the current time segment is somewhat influenced by surrounding time segment classifications. Temporal averaging may reduce the amount of calculation, while also potentially increasing statistical power. In general, the unit 864 will have determined the weightings by training on a data set with known annotations, in order to maximize the accuracy of the classifications. However, in an alternative embodiment the unit 864 may adjust parameters during operation according to some target function (e.g., a target function which states that the overall degree of detected periodic breathing should be 10%).

4.6.1.5 Classification

The classification component 880 may implement the concept of a classifier to determine whether the patient suffers from periodic breathing, or more particularly, whether the patient suffers from CSR. The concept of a classifier is common to many fields where it is desirable to assign an object or an underlying state of an object to one of a number of classes. This concept is used, for example, in the fields of voice recognition (where sound bites are classified as different words or syllables), radar detection (where visual signals are classified as enemy/friendly targets) and medical diagnosis (where test results are used to classify a patient's disease state). The design of a classifier falls under the field of pattern recognition. A classifier can be of a supervised type, that is, the classifier is built from training data which has been pre-classed by a supervisor or "expert." Alternatively, a classifier may be of an unsupervised type, where the natural ordering or clustering of the data determines the different classes. Time-domain signal classification usually relies on representing the signal at particular time points with "features." Features are simply numbers that distill the essence of the signal at a point in time, a form of compression. A set (or vector) of features may be called a "pattern."

For example, the classification component 880 may classify each ECG time segment to one of a number of classes. Such classes may include periodic breathing, Cheyne-Stokes, Obstructive sleep Apnea, and Mixed Apnea, normal breathing, among other possibilities. The classification component 880 may perform classification by analyzing one or more features extracted from an ECG time segment, or by analyzing a pattern of the features. The component 880 may manipulate the features or patterns mathematically with a suitable algorithm to determine classification.

Different methodologies may be used to classify features of an ECG time segment to detect periodic breathing. For instance, in a simple classifier model, an ECG time segment may be classified based on a single feature, such as a power spectral density of integrated RR intervals or a power spectral density of integrated EDR numbers. As illustrated in FIG. 9, the classifier may compare the power spectral density of the RR interval series between 0.01 and 0.03 Hz to a threshold. In the case that the power spectral density exceeds the threshold, periodic breathing may be deemed to have occurred. The probability or confidence associated with the occurrence of periodic breathing may depend on the extent that the power spectral density exceeds the threshold, for example by determining the difference between the density and the threshold. The threshold may be normalized with respect to the overall power in the power spectral density, to account for signal amplitude variations. The frequency boundaries may also be adjusted to be wider or narrower than [0.01 to 0.03 Hz] based on prior measurements from the individual or population. Both parametric and non-parametric approaches to power spectral density estimation may be used, or alternately an algorithm designed to recognize the frequency of a single dominant sine wave (e.g., the MUSIC algorithm as described in "Statistical Digital Signal Processing and Modeling" M. Hayes, 1996 (Pub: Wiley & Sons Inc.)) could be used. According to one form of the present technology, the component 880 may include one or more of the following units: a time segment classification unit 882, a periodic breathing calculation process 884, and a subject classification unit 886.

The time segment classification unit 882 will assign a label to the time segment (which will be either "periodic breathing (PB)" or "not periodic breathing" depending on the probability value from 864. In general, a threshold of 50% would be sufficient to label the time segment as PB, but the threshold for classification can be altered to different values. The unit 882 may produce a probability for each possible class that the time segment may be representative of (e.g., a value between 0 and 1). Following this, statistical analysis methods may be applied by the periodic breathing calculation process 884 to combine the classifications from each time segment to form an overall estimate for the complete record (e.g., if 10 time segments out of 100 are classified as PB, then the overall record could be classed as 10% periodic breathing).

Based on the output from the periodic breathing calculation process 884, the system may determine an overall subject classification using the subject classification unit 886. For example, the previous stage at process 884 may indicate a likelihood of 10% periodic breathing this could be combined with knowledge of the patient's weight and age to determine an overall probability that they have heart failure with periodic breathing present.

4.6.1.6 Output

Following classification, the present technology may output the result of classification. For instance, the present technology may output whether the patient suffers from periodic breathing or a more complex condition such as heart failure with periodic breathing. The present technology may provide detailed characteristics of the periodic breathing such as the associated periodicity, and the severity. The associated periodicity may be related to the circulation delay. In one example, the present technology may output a message, such as, "the average periodic breathing cycle is 56.1 seconds."

The present technology may output the degree of periodic breathing in a patient. For example, if each ECG time segment has an equal length of 10 minutes, the present technology may output a message, such as, "Subject A displayed 50 minutes (5 time segments) of periodic breathing during the last sleep period." In some cases, the output may trigger a treatment or treatment change, such as if the output is provided to a processor that controls a respiratory treatment apparatus, such as an RPT device described herein. For example, such a change may involve a change to a target ventilation setting or for a parameter for providing Pressure Support (e.g., an increase in Pressure Support).

4.6.2 Accelerometer Based Implementation

FIG. 8A illustrates an example implementation of a system 8000 configured to detect periodic breathing based on an accelerometer signal and may optionally do so without an ECG signal. As shown in FIG. 8A, the system 8000 may include one or more of the following: an Accelerometer input 8100, an accelerometer preprocessing component 8200, a feature extraction component 8400, and a classification component 8600. Details with regard to each component are described herein. Each component of the system may be comparable in some manner to the components described with reference to FIG. 8.

4.6.2.1 Accelerometer Input

The accelerometer input 8100 may provide an input signal indicative of a accelerometer measurement of a patient. Typically an accelerometer may be of the 3D type, which measures movements in three directions (x, y, and z). The accelerometer measurement may include body motion such that it may include motion representing patient's respiration activity. The input 8100 may include one or more accelerometers that provide accelerometer signals. In some embodiments, the input 8100 may include a device from which an accelerometer signal may be derived or accessed.

An accelerometer signal can be acquired using a surface-mounted accelerometer system. This could be a conventional wearable accelerometer that has the convenience of comfort and simplicity for patients, and hence can be used to acquire signals over longer periods of time. The accelerometer could be contained within a self-adhesive patch worn by the patient.

In such accelerometer acquisition systems, respiratory motion and/or a ballistocardiogram signal may be discretely derived from the raw motion signal provided by the accelerometer signals. Either may serve as a basis for detection of periodic breathing. In practice, the respiratory motion is likely to be larger in amplitude, and more amenable to processing for the detection of periodic breathing.

According to one aspect of the disclosed technology, an accelerometer signal may be split into time segments. A time segment may be as long as the entire record of the accelerometer signal or as short as the length of a representative hypopnea-hyperpnoea sequence. Time segments may be of equal length. In one example, each time segment may have a time length of 30 minutes. In another example, each time segment may have a time length of 10 minutes.

4.6.2.2 Accelerometer Preprocessing

The preprocessing component 8200 may perform a series of pre-processing steps on the accelerometer signal provided by the input 8100. As shown in FIG. 8A, the preprocessing component 8200 may include one or more of the following units: a signal combiner 8220, a pre-processing stage 8240, and a movement artefact rejection stage 8260.

The signal combiner 8220 forms a single respiratory-movement signal from the possible three axes of movement x, y, and z. The combiner may be of the type "maximum signal select" in which the signal component with the largest strength is chosen, or it could be a maximum ratio combining type. The net output will be a single signal for further processing.

The pre-processing stage 8240 may filter the accelerometer signal to remove any unwanted noise or low-frequency drift. For example, the pre-processing unit 8240 may remove from the accelerometer signal baseline problems, such as a baseline drift. To remove baseline problems, the unit 8240 may implement a linear low-pass filter in analog or digital domain, or a digital median filter. The pre-processing unit may also remove unwanted noise by either a low-pass or bandpass filter with appropriate settings (e.g., bandpass filter with passband from 0.05 to 2 Hz).

With continued reference to FIG. 8A, the movement artefact rejection unit 8260 may determine periods of high bodily movement, during which respiratory movement will be hard to determine, and for which accelerometer derived respiration will be unreliable. A means for detecting movement artefacts is to look at the residual high-frequency energy in the signal (e.g., take the difference of the signal and its median filtered version, and look for sections where there is high energy in this residual signal). The unit 8260 may replace the periods of high body movement with a blanked out signal or an average DC value.

4.6.2.3 Feature Extraction

With continued reference to FIG. 8A, the feature extraction component 8400 may extract or derive one or more features from an accelerometer time segment. Each feature may act as a compressed representation of the accelerometer time segment. The feature extraction component 8400 may include one or more of the following units: an accelerometer derived respiration unit 8420, a time segmentation unit 8440, and an ADR feature calculation unit 8460.

The ADR calculation unit 8420, will contain a processed accelerometer signal, with sections of high movement blanked out, and which reflects primarily the respiration related movement of the person. This signal will be continuous over the duration of the recording.

The time segmentation unit 8440 may break the ADR into distinct time segments (either overlapping or non-overlapping). For example, a time segment may be composed of 10 minutes of recording. The next segment could be the following ten minutes, or could be a ten-minute segment chosen 1 minute later than the original segment (overlapping case), for example.

The ADR feature calculation unit 8460 will calculate features based on the time segment presented to it. The features calculated will be representative of the respiration of the person during that segment. Features calculated may include a) the average respiration rate, b) the variability of the respiration rate, c) the variability of the respiration amplitude, d) the power spectral density of the ADR, e) the power under the respiratory peak of the PSD, f) the power within a frequency band corresponding to periodic breathing such as 0.01 Hz to 0.04 Hz, g) the envelope of the respiration signal, h) the variability of the envelope of the respiratory signal, i) a measure of the time-domain modulation depth of the respiration signal, j) the autocorrelation of the ADR signal, and k) the average cycle length of any modulation pattern present in the signal.

4.6.2.4 Classification and Posterior Probability Calculation

With continued reference to FIG. 8A, the classifier component 8600 may then assign a probability of periodic breathing to each accelerometer time segment, and hence ultimately a classification to each subject as to whether they have periodic breathing. The component 8620 may produce a probability value between zero and one for each accelerometer time segment. The posterior probability may reflect an uncertainty of classifying a particular epoch as having features indicative of periodic breathing. For example, a posterior probability of 0.7 may be interpreted as meaning that the particular time segment has a 70% chance of coming from a time segment where the subject had periodic breathing.

The classification component 8600 may implement the concept of a classifier to determine whether the patient suffers from periodic breathing, or more particularly, whether the patient suffers from CSR. The design of a classifier falls under the field of pattern recognition. A classifier can be of a supervised type, that is, the classifier is built from training data which has been pre-classed by a supervisor or "expert." Alternatively, a classifier may be of an unsupervised type, where the natural ordering or clustering of the data determines the different classes. Time-domain signal classification usually relies on representing the signal at particular time points with "features." Features are simply numbers that distill the essence of the signal at a point in time, a form of compression. A set (or vector) of features may be called a "pattern."

For example, the classification component 8600 may classify each accelerometer time segment to one of a number of classes. Such classes may include periodic breathing, Cheyne-Stokes, Obstructive sleep Apnea, and Mixed Apnea, normal breathing, among other possibilities. The classification component 8600 may perform classification by analyzing one or more features extracted from an accelerometer time segment, or by analyzing a pattern of the features. The component 8600 may manipulate the features or patterns mathematically with a suitable algorithm to determine classification.

Different methodologies may be used to classify features of an accelerometer time segment to detect periodic breathing. For instance, in a simple classifier model, an accelerometer time segment may be classified based on a single feature, such as a power spectral density of ADR numbers. The classifier may compare the power spectral density of the RR interval series between 0.01 and 0.03 Hz to a threshold. In the case that the power spectral density exceeds the threshold, periodic breathing may be deemed to have occurred. The probability or confidence associated with the occurrence of periodic breathing may depend on the extent that the power spectral density exceeds the threshold, for example by determining the difference between the density and the threshold. The threshold may be normalized with respect to the overall power in the power spectral density, to account for signal amplitude variations. The frequency boundaries may also be adjusted to be wider or narrower than [0.01 to 0.03 Hz] based on prior measurements from the individual or population. Both parametric and non-parametric approaches to power spectral density estimation may be used, or alternately an algorithm designed to recognize the frequency of a single dominant sine wave.

The component 8600 may be programmed to iterate through an entire length of an accelerometer signal, and calculate a probability value for each accelerometer time segment contained therein. The iteration may proceed until all accelerometer time segments have been processed. The component 8600 may result in a vector of probability values, each corresponding to a respective accelerometer time segment. An overall probability of periodic breathing for an accelerometer signal may be set to a maximum probability found in all accelerometer time segments of the accelerometer signal.

As shown in FIG. 8A, the component 8600 may include a classifier-posterior probability calculation unit 8620. One embodiment of such a classifier would be a linear discriminant classifier. The unit 8620 may include parameters adjusted during training. These parameters are the weights associated with the influence of each individual feature on the overall classification. In a linear classifier, the discriminant value is a linear combination of the features, i.e., the discriminant value will be $(a_1x_1+a_2x_2+ \ldots +a_ix_i+ \ldots a_Nx_N)$ where $x_i$ is a feature, and $a_i$ are "weighting". parameters. For each feature extracted from an accelerometer time segment, the unit 8620 may calculate a distance normal from the data point in the feature space to a decision boundary. The decision boundary is determined by a threshold value of the discriminant function implemented to characterize the accelerometer time segment for periodic breathing. A perpendicular distance may be mapped to a probability value where the probability value is a function of the distance from the decision boundary. If the distance is zero, the feature value would coincide with the boundary line, and the probability associated with the class membership is 0.5. As the distance increases to positive infinity, the probability may asymptotically approach towards to 1.0. As the distance increase to negative infinity, the probability may asymptotically approach towards 0.0. By defining the region feature space corresponding to periodic breathing as positive distance from the decision boundary, periodic breathing may be defined as any resulting probability value of greater than 0.5, or any other suitable value.

While we have described a linear discriminant classifier as one embodiment for 8620, a number of classifier types are available including: a Bayesian classification system, Bayesian maximum likelihood linear and quadratic discriminants, neural networks, clustering methods, can be used in 8620.

The component 8600 may also include a temporal posterior probability averaging unit 8640. The temporal posterior probability averaging unit takes the probabilities from nearby time segments and uses them to update the probability of the current time segment. For example, if the probability of a current time segment representing periodic breathing is 0.8, and the surrounding time segments have probability values of [0.3 0.3] (i.e., the sequence of time segment probabilities is [0.3 0.3 0.8 0.3 0.3] where 0.8 is the current time segment and the other values represent the probabilities of the preceding and following two time segments), then we could apply a weighing function of [0.05 0.05 0.8 0.05 0.05] to the probabilities and update the probability to 0.3×0.05+0.03×0.05+0.8×0.8+0.3×0.05+0.3× 0.05=0.7. In this way, the estimate for the current time segment is somewhat influenced by surrounding time segment classifications. Temporal averaging may reduce the amount of mis-classification, while also potentially increasing statistical power. In general, the unit 8640 will have determined the weightings by training on a data set with known annotations, in order to maximize the accuracy of the classifications. However, in an alternative embodiment the unit 8640 may adjust parameters during operation according to some target function (e.g., a target function which states that the overall degree of detected periodic breathing should be 10%).

The time segment classification unit 8660 takes the series of probabilities arising from the temporal posterior averaging, and assigns a class label of "periodic breathing" or "not periodic breathing" to each time segment, based on a rules such as p>0.5 results in a PB classification, where p is the posterior probability for that segment from 8640.

The subject classification unit 8680 then determines an overall patient by using the outputs of the time-segment classification. For example, an overall estimate for the complete subject record could be formed as follows: if 10 time segments out of 100 are classified as PB, then the overall record is classed as 10% periodic breathing.

Based on the output from the time segment classification 8660, the system may determine an overall subject classification using the subject classification unit 8680 combined with knowledge of the patient's weight and age to determine an overall probability that they have heart failure with periodic breathing present.

4.6.2.5 Output

Following classification, the present technology may output the result of classification. For instance, the present technology may output whether the patient suffers from periodic breathing or a more complex condition such as heart failure with periodic breathing. The present technology may provide detailed characteristics of the periodic breathing such as the associated periodicity, and the severity. The associated periodicity may be related to the circulation delay. In one example, the present technology may output a message, such as, "the average periodic breathing cycle is 56.1 seconds."

The present technology may output the degree of periodic breathing in a patient. For example, if each accelerometer time segment has an equal length of 10 minutes, the present technology may output a message, such as, "Subject A displayed 50 minutes (5 time segments) of periodic breathing during the last sleep period." In some cases, the output may trigger a treatment or treatment change, such as if the output is provided to a processor that controls a respiratory treatment apparatus, such as an RPT device described herein. For example, such a change may involve a change to a target ventilation setting or for a parameter for providing Pressure Support (e.g., an increase in Pressure Support).

4.6.3 Accelerometer and ECG Based Implementation

According to some forms of the present technology, periodic breathing may be detected based on an ECG signal in conjunction with an accelerometer signal.

In one example version of the system, probability of periodic breathing may be combined (such as by averaging) from the ECG based probability determination of FIG. 8 and the accelerometer based probability determination of FIG.

8A. For example, classification of each time segment may be based on the combined probabilities from each discrete probability determination from unit 860 and unit(s) 8600. Other methods for combining the probabilities so as to classify each time segment may also be implemented.

FIG. 10 shows another example system 1001 which processes both an ECG signal 6111 and an accelerometer signal 1002 in order to detect presence of periodic breathing. As discussed in more detail herein, the system 1001 may include one or more of the following components: an input accelerometer signal 1002, an input ECG signal 6111, an accelerometer preprocessing component 1012, an ECG preprocessing component 1020, a feature extraction component 1040, a posterior probability calculation component 1060, and a classification component 1080. One or more components of the system 1001 may be similar or identical to the components of the system 800 or 8000. For instance, the input ECG signal 6111 and the ECG preprocessing component 1020 may be similar or identical to the ECG input 810 and the ECG preprocessing component 820 discussed with regard to FIG. 8. Detailed discussion with respect to some other components illustrated in FIG. 10 is provided herein.

4.6.3.1 Accelerometer Input

The input accelerometer signal 1002 may provide one or more accelerometer signals indicative of movements of a patient's chest as the patient breathes in and out. The accelerometer signal may indicate movements in 1 or 3 dimensions. If the patient experiences periodic breathing, increases and decreases of amplitude may be reflected in the accelerometer signal.

The input 1002 may provide one or more signals indicative of the patient's orientation or position. For instance, the accelerometer signal may indicate whether the subject is in a supine or side position. In other words, the accelerometer signal may indicate whether the subject is lying on his or her back or lying on his or her side. This can help in overall assessment of the patient's condition, and may also be used to change the parameters in the classifier 1062, as periodic breathing is more likely to happen when the subject is supine than when they are resting at an angle.

The input signal 1002 may originate from an accelerometer measurement device configured to be adhered to the patient's chest, which may also be part of the described system. The accelerometer may be a three dimensional (3D) accelerometer. Alternatively, the input signal 1002 may originate from an ECG sensor containing an accelerometer, which may itself be part of the described system. For example, the input signal 1002 may originate from the surface patch 700 illustrated in FIG. 7, and the surface patch 700 may contain an accelerometer therein, where both the accelerometer and the surface patch may be part to the described system.

4.6.3.2 Accelerometer Preprocessing

The accelerometer preprocessing component 1012 may perform a series of pre-processing steps on the input accelerometer signal 1002 provided by the accelerometer, which may be comparable to that previously described in reference to FIG. 8A. As shown in FIG. 10, the accelerometer preprocessing component 1012 may include one or more of the following units: a movement artefact rejection and band-pass filter unit 1014, and a respiratory effort calculation unit 1016.

The movement artefact rejection and band-pass filter unit 1014 may scan the accelerometer signal for movement artefacts. Movement artefacts may refer to periods of high body movement or abrupt body movement. The beginning of such a period may be marked by an initial sharp negative spike in the accelerometer signal followed by an abrupt positive spike.

The unit 1014 may remove the periods of high body movement from analysis. In the alternative, the unit 1014 may replace the periods of high body movement with a blanked out signal or an average DC value.

Once the movement artefacts have been removed from the accelerometer signal, the accelerometer signal may be filtered by a band-pass filter. The filter may be configured to pass the accelerometer signal associated with respiration. For instance, the filter may pass the signal within a respiration frequency range, such as between 0.1 and 0.5 Hz. The filter may eliminate signals outside of the respiration frequency range.

The respiratory effort calculation unit 1016 may perform an envelope detection algorithm over the accelerometer signal to modulate the breathing amplitude. For instance, the unit 1016 may perform a Hilbert transform on the accelerometer signal to detect the periodic breathing modulation. An alternative to the Hilbert transform is to detect the envelope of the respiration signal by convolving the accelerometer signal with a target respiration signal.

Feature Extraction

With continued reference to FIG. 10, the feature extraction component 1040 may extract one or more features from an ECG signal and accelerometer signal. The component 1040 may include one or more of the following units: a respiratory effort feature extraction unit 1041, an RR-interval feature extraction unit 1042, an EDR feature extraction unit 1044 and a feature combiner unit 1046.

The respiratory effort feature extraction unit 1041 may extract one or more features from the accelerometer signal. For instance, the unit 1041 may extract a respiratory effort feature. In one example, the unit 1041 may calculate a power spectral density of a demodulated envelope signal. The unit 1041 may calculate respiratory effort features based on power spectral density values in a range between 0.01 and 0.03 Hz.

The RR-interval feature extraction unit 1042 and the EDR feature extraction unit 1044 may be respectively similar or identical to the RR-interval feature extraction unit 842 and the EDR feature extraction unit 844 described with respect to FIG. 8. For instance, the unit 1042 may calculate a power spectral density of RR intervals obtained from an ECG time segment. The unit 1044 may calculate a power spectral density estimate of EDR vector obtained from an ECG time segment.

The feature combiner unit 1046 may combine features extracted by the respiratory effort feature extraction unit 1041, the RR-interval feature extraction unit 1042, and the EDR feature extraction unit 1044. The unit 1046 may group one or more features to form a pattern. The pattern may be manipulated with a suitable classifier algorithm to produce a probability for each possible class for which the ECG signal and the accelerometer signal may represent.

4.6.3.3 Posterior Probability Calculation

With continued reference to FIG. 10, the posterior probability calculation component 1060 may implement algorithms similar to that of the posterior probability calculation component 860 of FIG. 8. The component 1060 may determine a probability of periodic breathing or other respiratory related event based on one or more features extracted from the ECG signal and the accelerometer signal, The feature combining at unit 1046 takes the feature vectors from each individual input (RR, EDR and accelerometer) and arranges it into one combined vector for input to the classifier 1062.

4.6.3.4 Classification

With continued reference to FIG. 10, the classification component 1080 may implement algorithms similar to that of the classification component 880 of FIG. 8. The classification component 1080 may perform a classification to determine whether the patient suffers from periodic breathing by analyzing one or more features extracted from the ECG signal and the accelerometer signal. In one example, the classification component 1080 may determine whether the patient/subject suffers from CSR.

4.6.4 Further ECG Example Embodiments

FIG. 11 illustrates another example with processes similar to those previously described. In this processing, the QRS fiducial points and associated times and amplitudes are extracted from a cardiac signal 6111. For example, a single channel of raw ECG is fed into the processing system (e.g., one or more processors). Typically, there is a pre-processing stage 1101 which implements processing such as bandpass filtering to remove powerline noise, EMG jitter and low frequency wander due to electrical noise. The QRS detection stage 1102 may be implemented with a variety of methods such as template matching, detection of change points, peak detection etc., or any other known methodology. The resulting outputs from a QRS detection stage may then include amplitude values of each QRS (the R-peak), and, optionally, the times at which the R-peak occurs.

In this case, the peaks may contain small deviations in the R-peak amplitude value that are induced by respiration effort. Hence, the R-peak amplitude value may optionally be considered in relation to a baseline value of the ECG signal so as to promote evaluation of the existence of such deviations. One example methodology for establishing a baseline reference may involve implementation of a median filter 1105. This process may filter the input raw ECG signal with a long time constant (e.g., 10 seconds).

The resulting/output baseline signal may then be applied as input into processing block 1103 along with the R-peak amplitude values where the relative QRS amplitude is determined with respect to the estimate of the baseline ECG voltage. For example, the R-peak values may be added, subtracted or divided by the baseline signal to produce a relative QRS amplitude (designated in FIG. 11 as A1, A2, etc.).

A QRS time process 1104 may generate a sequence of times. This may include the times at which each R-peak occurs (i.e., "QRS times"), and lead to a sequence of discrete events at times B1, B2, etc. The interbeat interval (RR times) can be determined as be the difference between successive beats (e.g., $B_i - B_{i-1}$) and may optionally be produced as a sequence of RR times.

FIG. 12 shows the processing for determining whether Cheyne-Stokes respiration has occurred in individual segments of the ECG signal. The overnight signal recorded by the ECG (e.g., 8 hrs=480 minutes) may be divided into segments (the segments may optionally overlap or be disjoint) of a chosen time period (e.g., 10 minutes). Other time lengths for the segments may be chosen. Effectively, a desired segment time length could be chosen so that it is longer than at least one cycle of a CSR period. Such segments may then serve the basis for segments of any one or more of the RR interval times, beat times and/or relative QRS amplitude values, etc.

With the segments, the power spectrum may be determined such as in power spectrum processes 1202/1203. For example, the RR interbeat time sequence contained in a segment may be applied to power spectrum process 1202 to determine an RR time segment PSD. Each of the segments may be sequentially calculated by such a power spectrum process. Each power spectrum can be calculated with a number of different techniques such as the modified averaged periodogram and/or a parametric spectral estimate based on an autoregressive moving average model. Other methods for power spectral density PSD may be included. In this regard, a PSD estimate can be calculated on the raw interbeat interval series, or on a time series which has been resampled to real time by calculating an instantaneous heart rate (as described in de Boer R W, Karemaker J M, Strackee J. Spectrum of a series of point events, generated by the integral pulse frequency modulation model. Med Biol Eng Comput. 1985 March; 23(2):138-42.)

Optionally, the power spectral density estimate of the QRS amplitude signal (the sequence of values A1, A2, in FIG. 11) can also be determined in power spectrum process 1203. Such a process may, for example, use standard power spectral density estimate methodologies as discussed above. Each of the segments may be sequentially calculated by such a power spectrum process.

Since CSR occurs at time scales from approximately 40 to 100 seconds, the power spectral density estimates are included to estimate the power in a predetermined range (e.g., the band from 0.01 to 0.025 Hz). Thus, the produced estimates may be integrated in this range. Each integrated value for each segment, whether based on time values or amplitude values as previously discussed, may be considered a CSR-band power. These CSR-band power values may then be implemented for automated classification of periodic breathing.

FIG. 13 further illustrates examples of how the per-segment processing previously discussed can be applied as a useful metric for overall estimation of Cheyne-Stokes respiration or periodic breathing. In this example, an overnight ECG recording is analyzed with the processing discussed herein. It is divided into overlapping segments, each of ten minute length. In the illustration, there is a nine minute overlap, so that each segment is one minute advanced compared to the previous segments. The power spectral density processing is applied to each segment such as discussed in reference to FIG. 12, and this produces one or more PSD estimates for each segment. For example, the CSR band-power may be calculated for each segment, so that a plot of segment number versus CSR band power may be produced. The number of significant CSR band power values (e.g., a number that are above a pre-determined threshold) may be counted such as by a processor. This number may serve as a periodic breathing indicator (illustrated as "$N_{th}$" in FIG. 13). Optionally, the count may be part of a ratio, such as a ratio of the count of significant CSR band power values to a count of segments (e.g., overall number of segments N from an ECG recording session). For example, if the count of significant CSR band power values is forty (i.e., $N_{th}$=40) and a total number of processed segments considered is four hundred and eighty (i.e., N=480), an overall percentage of the recording session (e.g., a sleep session or night) with CSR may be presented as 40/480 or 8.3%.

A further useful feature for CSR indication concerns cycle length. An estimate of the cycle length of the CSR is often associated with the prognosis of the patient. In general, longer cycle lengths are associated with poor prognosis in patients with heart failure. There are several mechanisms that may be implemented in some versions of the technology herein for estimating the average cycle length. One such estimate may be calculated by combining the cycle length estimates that are represented by the determined CSR band power values from each segment. For example, as illustrated in FIG. 14A, segments, such as from one or more recording sessions, may be selected according to whether their CSR band power is above a certain threshold. These selected segments may then contribute to an estimate of CSR frequency. For example, from each segment, a peak power may be detected so as to determine the frequency of highest power. These determined frequencies from each segment may be averaged. Optionally, the frequency may be converted (by inverse function) to output the average frequency in the form of an estimate of average cycle length (i.e., time).

In the example shown in FIG. 14A, segment i has a significant CSR band power value (i.e., it is above a predetermined assessment threshold), and the frequency at which the highest power occurs is 0.015 Hz. In some versions, a table of significant segments with CSR present can be established (such as those chosen according to CSR band power values and a predetermined threshold). A global average can be taken over the segments of the table to calculate the average CSR frequency or an estimate of average cycle length.

In another alternative version shown in FIG. 14B, the entire night's recording can be taken and the power spectral density estimate may be calculated from it in a process without the segmentation previously described. A single peak may then be detected from the entire recording session. The frequency at which the peak power occurs may then be output as an indication of frequency of CSR. Its inverse may also be calculated as the estimated average cycle length. For example, if the CSR frequency is 0.018 Hz, then the cycle length is 55.6 seconds.

4.6.5 Other Embodiments

Implementations discussed herein regarding detection of periodic breathing are mere examples. More or less components may be included in the systems 800 and 1001, as desired.

By way of example, the present technology may detect periodic breathing based on an oximeter plethysmogram signal. For instance, the present technology may derive RR intervals from the oximeter plethysmogram signal, and detect periodic breathing based on the derived RR intervals.

In another example, the present technology may implement a control methodology to respond to detected periodic breathing. For example, methodologies described herein for detecting periodic breathing may be implemented with a respiratory treatment apparatus such as, a flow generator or a servo controlled blower. The treatment apparatus may deliver a respiratory treatment or pressure therapy regime, such as a therapeutic pressure level associated with Pressure Support treatment. The treatment apparatus may automatically adjust such therapeutic pressure levels in response to the detection of periodic breathing conditions. For example, pressure levels and/or a target ventilation may be increased by a specified amount, or varied otherwise, upon detection of periodic breathing. Optionally, the pressure levels or target ventilation may be increased proportionally as a function of a detected periodic breathing severity.

4.6.6 Advantages of the Present Technology

There may be advantages associated with the present technology. For instance, by detecting periodic breathing based on an ECG, or on a ECG and accelerometer, input, the present technology obviates any need for sensors required by traditional technologies for detecting periodic breathing. Such sensors include an airflow sensor and an explicit respiratory effort sensor such as an inductance plethysmogram.

Further, the present technology simplifies the test for detecting periodic breathing. As disclosed herein, the test may be performed in parallel with a cardiac arrhythmia test or as a stand-alone test. In a stand-alone test, a patient may simply wear a patch, such as the patch 700 of FIG. 7, which is less cumbersome than traditional systems that require an airflow sensor or a respiratory effort sensor. When the test is performed in parallel with a cardiac arrhythmia test, a physician such as a dentist or cardiologist may receive an indication of the level of periodic breathing at the same time as getting an assessment of cardiac arrhythmia. If periodic breathing is indicated, the physician can immediately prescribe an adaptive servo-ventilation (ASV) without recourse to a full lab test.

4.7 Glossary

For the purposes of the present technology disclosure, in certain forms of the present technology, one or more of the following definitions may apply. In other forms of the present technology, alternative definitions may apply.

4.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g. acoustic) noise may be considered to be the background noise level in the room where a patient is located, other than for example, noise generated by a RPT device or emanating from a mask or patient interface. Ambient noise may be generated by sources outside the room.

Continuous Positive Airway Pressure (CPAP): CPAP treatment will be taken to mean the application of a supply of air to the entrance to the airways at a pressure that is continuously positive with respect to atmosphere, and preferably approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

4.7.2 Aspects of the Respiratory Cycle

Apnea: Preferably, apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): Preferably breathing effort will be said to be the work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
  (i) Flattened: Having a rise followed by a relatively flat portion, followed by a fall.
  (ii) M-shaped: Having two local peaks, one at the leading edge, and one at the trailing edge, and a relatively flat portion between the two peaks.
  (iii) Chair-shaped: Having a single local peak, the peak being at the leading edge, followed by a relatively flat portion.
  (iv) Reverse-chair shaped: Having a relatively flat portion followed by single local peak, the peak being at the trailing edge.

Hypopnea: Preferably, a hypopnea will be taken to be a reduction in flow, but not a cessation of flow. In one form, a hypopnea may be said to have occurred when there is a reduction in flow below a threshold for a duration. A central hypopnea will be said to have occurred when a hypopnea is detected that is due to a reduction in breathing effort. In one form in adults, either of the following may be regarded as being hypopneas:
  (i) a 30% reduction in patient breathing for at least 10 seconds plus an associated 4% desaturation; or
  (ii) a reduction in patient breathing (but less than 50%) for at least 10 seconds, with an associated desaturation of at least 3% or an arousal.

Hyperpnea: An increase in flow to a level higher than normal flow.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow (Qpeak): The maximum value of flow during the inspiratory portion of the respiratory flow waveform.

Respiratory flow, airflow, patient airflow, respiratory airflow (Qr): These synonymous terms may be understood to refer to the RPT device's estimate of respiratory airflow, as opposed to "true respiratory flow" or "true respiratory airflow", which is the actual respiratory flow experienced by the patient, usually expressed in liters per minute.

Tidal volume (Vt): The volume of air inhaled or exhaled during normal breathing, when extra effort is not applied.

(inhalation) Time (Ti): The duration of the inspiratory portion of the respiratory flow waveform.

(exhalation) Time (Te): The duration of the expiratory portion of the respiratory flow waveform.

(total) Time (Ttot): The total duration between the start of the inspiratory portion of one respiratory flow waveform and the start of the inspiratory portion of the following respiratory flow waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

4.7.3 RPT Device Parameters

Flow rate (or flow): The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. Total flow, Qt, is the flow rate of air leaving the RPT device. Vent flow, Qv, is the flow rate of air leaving a vent to allow washout of exhaled gases. Leak flow, Ql, is the flow rate of unintentional leak from a patient interface system. Respiratory flow, Qr, is the flow rate of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face. In one example leak may occur in a swivel elbow.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes in the patient interface.

Pressure: Force per unit area. Pressure may be measured in a range of units, including $cmH_2O$, $g-f/cm^2$, hectopascal.

1 cmH$_2$O is equal to 1 g-f/cm$^2$ and is approximately 0.98 hectopascal. In this specification, unless otherwise stated, pressure is given in units of cmH$_2$O. The pressure in the patient interface is given the symbol Pm, while the treatment pressure, which represents a target value to be achieved by the mask pressure Pm at the current instant of time, is given the symbol Pt.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as 10$^{-12}$ watt.

Sound Pressure: The local deviation from ambient pressure at a given time instant as a result of a sound wave travelling through a medium. Sound pressure is usually given in decibels SPL, that is, decibels relative to a reference pressure, normally taken as 20×10$^{-6}$ Pascal (Pa), considered the threshold of human hearing.

4.7.4 Terms for Ventilators

Adaptive Servo-Ventilator: A ventilator that has a changeable, rather than fixed target ventilation. The changeable target ventilation may be learned from some characteristic of the patient, for example, a respiratory characteristic of the patient.

Backup rate: A parameter of a ventilator that establishes the minimum respiration rate (typically in number of breaths per minute) that the ventilator will deliver to the patient, if not otherwise triggered.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

EPAP (or EEP): a base pressure, to which a pressure varying within the breath is added to produce the desired mask pressure which the ventilator will attempt to achieve at a given time.

IPAP: desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the minimum value during expiration (e.g., PS=IPAP−EPAP). In some contexts pressure support means the difference which the ventilator aims to achieve, rather than what it actually achieves.

Servo-ventilator: A ventilator that measures patient ventilation has a target ventilation, and which adjusts the level of pressure support to bring the patient ventilation towards the target ventilation.

Spontaneous/Timed (S/T)—A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Ventilator: A mechanical device that provides pressure support to a patient to perform some or all of the work of breathing.

4.7.5 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

4.7.6 Periodic Breathing

QRS (also referred to as a QRS complex)—a reference to a periodic peak formation defined by the so called Q, R, and S waves in a typical electrocardiogram (ECG).

RR interval—the period between two QRS complexes (e.g., from a peak of one to a peak of the next one).

EDR—ECG-derived respiration.

LD (or LD classifier)—linear discriminant classifier

BPF—band pass filter 4.8 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

For example, in some versions, the technology may embody a system for detecting the presence of Cheyne-Stokes respiration (CSR), the system may include:
one or more sensors configured to measure an electrocardiogram;
a processor for analysing the recorded electrocardiogram signal, the processing steps consisting of:
calculating both the times and amplitudes of the QRS points in the electrocardiogram;
determining a spectral density estimate of the interbeat intervals and QRS amplitudes;
calculating the likelihood of CSR within a segment by comparison of features derived from the spectral density estimate with a threshold;
reporting the overall occurrence of CSR during the recording.

The system of the previous paragraph may further include an adhesive patch placeable on a subject for a period of time (e.g., more than four hours) having the sensors, in which the electrocardiogram signal may be obtained.

The system of any previous paragraph may further include a chronically implanted device in which the electrocardiogram signal is obtained.

The system of any previous paragraph in which a segment of electrocardiogram signal containing Cheyne-Stokes respiration is recognised by calculating the power in the interbeat interval spectrum over a very low frequency range, and comparing said power to a predetermined threshold.

The system of any previous paragraph in which the presence of Cheyne-Stokes respiration in a subject is determined by assessing the presence or absence of Cheyne-Stokes respiration in segments shorter than the overall electrocardiogram recording and then combining the per-segment assessments into an overall estimate.

The system of any previous paragraph in which the average cycle length associated with the Cheyne-Stokes respiration is determined by forming a spectral density estimate of the interbeat interval spectrum, and determining the frequency at which the spectral peak occurs in a range where CSR is physiologically likely to occur.

The invention claimed is:

1. An apparatus for detecting periodic breathing in a patient, the apparatus comprising:
a processor configured to:
receive an electrocardiogram (ECG) signal of the patient;
derive a feature from the ECG signal; and
analyze the feature derived from the ECG signal to determine an occurrence of periodic breathing,
wherein the processor is further configured to:
receive an accelerometer signal indicative of the patient's position,
derive a feature from the accelerometer signal, and
analyze the feature derived from the accelerometer signal to determine an occurrence of periodic breathing,
wherein the feature derived from the accelerometer signal is a power spectral density of a demodulated envelope signal of the accelerometer signal.

2. The apparatus of claim 1, further comprising a memory for storing the ECG signal.

3. The apparatus of claim 1, further comprising a sensor to measure the ECG signal from the patient.

4. The apparatus of claim 3, wherein the sensor is a Holter monitor.

5. The apparatus of claim 3, wherein the sensor is a 12-lead ECG.

6. The apparatus of claim 3, wherein the sensor is a patch type ECG.

7. The apparatus of claim 1, wherein the processor is configured to perform a time-domain analysis of the ECG signal.

8. The apparatus of claim 1, wherein the processor is configured to perform a frequency-domain analysis of the ECG signal.

9. The apparatus of claim 1, wherein the processor is configured to divide the ECG signal into a plurality of time segments of equal time length.

10. The apparatus of claim 9, wherein the processor is configured to determine whether each time segment of the plurality of time segments exhibits a characteristic of periodic breathing.

11. The apparatus of claim 1, wherein the processor determines a likelihood of the patient having periodic breathing.

12. The apparatus of claim 1, wherein the processor is configured to derive a respiratory signal from the ECG signal.

13. The apparatus of claim 12, wherein the processor is configured to analyze an envelope of the derived respiratory signal.

14. The apparatus of claim 1, wherein the feature derived from the ECG signal is a power spectral density of RR intervals in the ECG signal.

15. The apparatus of claim 1, wherein the feature derived from the ECG signal is a power spectral density of ECG-derived respiration (EDR) numbers.

16. The apparatus of claim 15, wherein an EDR number is a magnitude of a QRS peak in the ECG signal.

17. The apparatus of claim 15, wherein an EDR number is an integral of an area around a QRS peak in the ECG signal.

18. The apparatus of claim 1, wherein the processor determines the occurrence of periodic breathing by comparing the feature in a respiration frequency range to a predetermined threshold.

19. The apparatus of claim 1, wherein the processor is configured to perform baseline correction on the ECG signal.

20. The apparatus of claim 1, further comprising a sensor to measure the accelerometer signal.

21. The apparatus of claim 1, further comprising a sensing device configured to measure the accelerometer signal and the ECG signal.

22. The apparatus of claim 21, wherein the sensing device is a patch type ECG.

23. The apparatus of claim 1, wherein the processor is further configured to derive an additional feature from the accelerometer signal, and wherein the additional feature derived from the accelerometer signal is a respiratory effort feature.

24. The apparatus of claim 1, wherein the processor is configured to remove a movement artefact from the accelerometer signal.

25. The apparatus of claim 1, wherein the periodic breathing is Cheyne-Stokes respiration.

26. The apparatus of claim 1, wherein the processor is configured to combine features from the accelerometer signal and the ECG signal, in order to determine an occurrence of periodic breathing.

27. The apparatus of claim 26, wherein the combined features comprise RR-interval, EDR and Respiratory Effort extracted features.

28. The apparatus of claim 1 wherein to analyze the feature derived from the ECG signal, the processor determines power spectrum of RR interval times or relative QRS amplitude values on a segment-by-segment basis.

29. The apparatus of claim 28 wherein the processor is configured to integrate the power spectrum in a predetermined range to output a CSR band power value.

30. The apparatus of claim 1 wherein the processor is configured to compare CSR band power values to a predetermined threshold to detect significant CSR band power values.

31. The apparatus of claim 1 wherein the processor is configured to count significant CSR band power values.

32. The apparatus of claim 31 wherein the processor is configured to present a ratio of the count of significant CSR band power values to a total number of time segments.

33. The apparatus of claim 1 wherein the processor is configured to determine an average CSR frequency or average cycle length from time segments selected according to significant CSR band power values.

34. The apparatus of claim 1 wherein the analysis of the feature derived from the accelerometer signal and the analysis of the feature derived from the ECG signal comprises classifying periodic breathing, in a classifier, with the derived feature from the accelerometer signal and the derived feature from the ECG signal.

35. The apparatus of claim 1 wherein the analysis of the feature derived from the accelerometer signal and the analysis of the feature derived from the ECG signal comprises classifying Cheyne-Stokes respiration, in a classifier, with the derived feature from the accelerometer signal and the derived feature from the ECG signal.

36. A method for detecting periodic breathing in a patient, the method comprising:
receiving, by a processor, an electrocardiogram (ECG) signal of the patient;
deriving, by the processor, a feature from the ECG signal;
analyzing, by the processor, the feature derived from the ECG signal to determine an occurrence of periodic breathing,
receiving an accelerometer signal indicative of the patient's position,
deriving a feature from the accelerometer signal, and
analyzing the feature derived from the accelerometer signal to determine an occurrence of periodic breathing,
wherein the feature derived from the accelerometer signal is a power spectral density of a demodulated envelope signal of the accelerometer signal.

37. The method of claim 36, further comprising retrieving the ECG signal from a memory.

38. The method of claim 36, wherein the ECG signal is provided by a sensor.

39. The method of claim 36, further comprising performing a time-domain analysis of the ECG signal.

40. The method of claim 36, further comprising performing a frequency-domain analysis of the ECG signal.

41. The method of claim 36, further comprising dividing the ECG signal into a plurality of time segments of equal time length.

42. The method of claim 41, further comprising determining whether each time segment of the plurality of time segments exhibits a characteristic of periodic breathing.

43. The method of claim 36, further comprising determining a likelihood of the patient having periodic breathing.

44. The method of claim 36, further comprising deriving a respiratory signal from the ECG signal.

45. The method of claim 44, further comprising analyzing an envelope of the derived respiratory signal.

46. The method of claim 36, wherein the feature derived from the ECG signal is a power spectral density of RR intervals in the ECG signal.

47. The method of claim 36, wherein the feature derived from the ECG signal is a power spectral density of ECG-derived respiration (EDR) numbers.

48. The method of claim 47, wherein an EDR number is a magnitude of a QRS peak in the ECG signal.

49. The method of claim 47, wherein an EDR number is an integral of an area around a QRS peak in the ECG signal.

50. The method of claim 36, wherein the processor determines an occurrence of periodic breathing by comparing the feature in a respiration frequency range to a predetermined threshold.

51. The method of claim 36, further comprising performing baseline correction on the ECG signal.

52. The method of claim 36, further comprising deriving, by the processor, an additional feature from the ECG signal, wherein the additional feature derived from the accelerometer signal is a respiratory effort feature.

53. The method of claim 36, further comprising removing a movement artefact from the accelerometer signal.

54. A method for detecting periodic breathing in a patient, the method comprising:
receiving, by a processor, an electrocardiogram (ECG) signal of the patient;
deriving, by the processor, a feature from the ECG signal;
analyzing, by the processor, the feature to determine an occurrence of periodic breathing,
receiving an accelerometer signal indicative of the patient's position,
deriving a feature from the accelerometer signal,
analyzing the feature derived from the accelerometer signal to determine an occurrence of periodic breathing, and
filtering the accelerometer signal by a band-pass filter.

55. The method of claim 36, wherein the periodic breathing is Cheyne-Stokes respiration.

56. The method of claim 36, further comprising combining features from the accelerometer signal and the ECG signal, in order to determine an occurrence of periodic breathing.

57. The method of claim 56, wherein the combined features comprise RR-interval, EDR and Respiratory Effort extracted features.

58. The method of claim 36 wherein the analyzing of the feature derived from the ECG signal comprises determining power spectrum of RR interval times or relative QRS amplitude values on a segment-by-segment basis.

59. The method of claim 58 further comprising integrating the power spectrum in a predetermined range to output a CSR band power value.

60. The method of claim 36 further comprising comparing CSR band power values to a predetermined threshold to detect significant CSR band power values.

61. The method of claim 36 further comprising counting significant CSR band power values.

62. The method of claim 61 further comprising presenting a ratio of a count of significant CSR band power values to a total number of time segments.

63. The method of claim 62 further comprising determining an average CSR frequency or average cycle length from segments selected according to significant CSR band power values.

64. An apparatus for detecting periodic breathing in a patient, the apparatus comprising:
a processor configured to:
receive an accelerometer signal and an electrocardiogram (ECG) signal of the patient;
derive features from the accelerometer signal and the electrocardiogram (ECG) signal; and
analyze the features to determine an occurrence of periodic breathing, wherein the features include a power spectral density of a demodulated envelope signal of the accelerometer signal.

65. A method for detecting periodic breathing in a patient, the method comprising:
receiving, by a processor, an accelerometer signal and an electrocardiogram (ECG) signal of the patient;
deriving, by the processor, features from the accelerometer signal and the electrocardiogram (ECG) signal; and
analyzing, by the processor, the features to determine an occurrence of periodic breathing, wherein the features include a power spectral density of a demodulated envelope signal of the accelerometer signal.

66. An apparatus for detecting periodic breathing in a patient, the apparatus comprising:
a processor configured to:
receive an electrocardiogram (ECG) signal of the patient;
derive a feature from the ECG signal; and
analyze the feature to determine an occurrence of periodic breathing,
wherein the processor is configured to:
receive an accelerometer signal indicative of the patient's position,
derive a feature from the accelerometer signal, and
analyze the feature derived from the accelerometer signal to determine an occurrence of periodic breathing,
the apparatus further comprising a band-pass filter to filter the accelerometer signal.

* * * * *